US010335116B2

(12) United States Patent
Boctor et al.

(10) Patent No.: US 10,335,116 B2
(45) Date of Patent: Jul. 2, 2019

(54) ROBOT ASSISTED ULTRASOUND SYSTEM

(71) Applicant: The Johns Hopkins University, Baltimore, MD (US)

(72) Inventors: Emad M. Boctor, Baltimore, MD (US); Iulian I. Iordachita, Lutherville, MD (US); Xiaoyu Guo, Baltimore, MD (US); Alexis Cheng, Baltimore, MD (US); Haichong Zhang, Baltimore, MD (US); Fereshteh Aalamifar, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 856 days.

(21) Appl. No.: 14/690,232

(22) Filed: Apr. 17, 2015

(65) Prior Publication Data
US 2015/0297177 A1    Oct. 22, 2015

Related U.S. Application Data

(60) Provisional application No. 61/981,069, filed on Apr. 17, 2014.

(51) Int. Cl.
A61B 8/00    (2006.01)
A61B 8/14    (2006.01)
(Continued)

(52) U.S. Cl.
CPC ............ *A61B 8/4209* (2013.01); *A61B 8/145* (2013.01); *A61B 8/15* (2013.01); *A61B 8/4218* (2013.01);
(Continued)

(58) Field of Classification Search
CPC ..... Y10S 901/47; Y10S 901/02; A61B 90/50; A61B 34/30; A61B 2034/2055;
(Continued)

(56) References Cited

U.S. PATENT DOCUMENTS 4,434,661 A * 3/1984 Miwa ................. A61B 8/13
73/625
6,019,724 A * 2/2000 Gronningsaeter ... A61B 8/0833
600/439

(Continued)

OTHER PUBLICATIONS

Abolmaesumi et al., "Image-guided control of a robot for percutaneous Cholecystostomy", Phys. Med. Biol. 49(3), 2004, pp. 441-445.
(Continued)

*Primary Examiner* — Thomas J Hong
*Assistant Examiner* — Helene Bor
(74) *Attorney, Agent, or Firm* — Harrity & Harrity, LLP

(57) ABSTRACT

According to some embodiments of the invention, a robot-assisted ultrasound system includes a first ultrasound probe, a robot comprising a manipulator arm having a tool end, and a second ultrasound probe attached to the tool end of the manipulator arm. The robot-assisted ultrasound system further includes a robot control system configured to control at least one of a position or a pose of the second ultrasound probe based on a contemporaneous position and pose of the first ultrasound probe, and an ultrasound processing and display system configured to communicate with at least one of the first and second ultrasound probes to receive and display an ultrasound image based on the first and second ultrasound probes acting in conjunction with each other.

21 Claims, 42 Drawing Sheets

(51) Int. Cl.
*A61B 8/15* (2006.01)
*A61B 34/20* (2016.01)
*A61B 34/30* (2016.01)
*A61B 90/50* (2016.01)

(52) U.S. Cl.
CPC .......... *A61B 8/4263* (2013.01); *A61B 8/4477* (2013.01); *A61B 34/30* (2016.02); *A61B 90/50* (2016.02); *A61B 2034/2055* (2016.02); *Y10S 901/47* (2013.01)

(58) Field of Classification Search
CPC ... A61B 8/4477; A61B 8/4263; A61B 8/4218; A61B 8/15; A61B 8/145; A61B 34/37; A61B 8/4209
See application file for complete search history.

(56) References Cited

U.S. PATENT DOCUMENTS

| | | | |
|---|---|---|---|
| 6,425,865 | B1 | 7/2002 | Salcudean et al. |
| 7,571,025 | B2* | 8/2009 | Bischoff ............. B25J 9/1682 219/121.6 |
| 2005/0183532 | A1* | 8/2005 | Najafi ..................... A61B 8/00 74/490.01 |
| 2007/0021738 | A1 | 1/2007 | Hasser et al. |
| 2008/0021317 | A1 | 1/2008 | Sumanaweera |
| 2011/0125022 | A1* | 5/2011 | Lazebnik ............ A61B 8/4461 600/444 |
| 2012/0022552 | A1* | 1/2012 | Neff ......................... A61N 7/02 606/130 |
| 2013/0338490 | A1 | 12/2013 | Wendler |
| 2013/0338505 | A1 | 12/2013 | Schneider et al. |
| 2014/0350571 | A1* | 11/2014 | Maillet ................. B25J 19/026 606/130 |

OTHER PUBLICATIONS

Burgin et al., "Using depth information to improve face detection", Proceedings of the 6th International Conference on Human-Robot Interaction, Lausanne, Switzerland, 2011, pp. 6-9.
Guo et al., "Photoacoustic Active Ultrasound Element for Catheter Tracking", SPIE Photonics West 2014.
Guo et al., "Active echo: a new paradigm for ultrasound calibration." Medical Image Computing and Computer Assisted Intervention 2014.
Hansen et al., "Ultrasound breast imaging using full angle spatial compounding: in-vivo results," IEEE Ultrasonics Symposium, 54-57 (2008) [doi:10.1109/ULTSYM.2008.0014].
Ho et al., "Robotic ultrasound guided prostate intervention device: system description and results from phantom studies," The International Journal of Medical Robotics and Computer Assisted Surgery 5(1), 51-58 (2009) [doi:10.1002/rcs.232].
Hong et al., "An ultrasound driven needle insertion robot for percutaneous cholecystostomy", Phys. Med. Biol. 49(3), 2004. pp. 441-455.
Izadi et al., "KinectFusion: real-time 3D reconstruction and interaction using a moving depth camera", UIST'11 Proceedings of the 24th Annual ACM Symposium on User Interface Software and Technoloqy , ACM New York, NY, USA, 2011, pp. 559-568.
Jago et al., "XRES©: adaptive enhancement of ultrasound images," Medicamundi 46(3), 36-41 (2002).
Jago et al., "Experimental studies in transmission ultrasound computed tomography." Physics in medicine and biology 36.11 (1991): 1515.
Kang et al., "Software framework for spatially tracked prebeamformed RF data acquisition with a freehand clinical ultrasound transducer," In SPIE Medical Imaging (pp. 90401W-90401W). International Society for Optics and Photonics. 2014.
Khoei, "Quantitative ultrasound computed tomography imaging of PAGAT radiation dosimetry gel," Ph.D. dissertation, School of Chemistry, Physics & Mechanical Eng., Queensland Univ. of Tech., Australia (2013).
Kim et al., "Multiband tissue differentiation in ultrasonic transmission tomography," in Medical Imaging, Proc. SPIE 5035, 41-48 (2003) [doi:10.1117/12.479887].
Lasaygues et al., "Ultrasonic computer tomography," in Bone Quantitative Ultarsound Book, Springer, 441-459 (2011) [doi:10.1007/978-94-007-0017-8_17].
Lessard et al, "Parallel Robot for medical 3D-Ultrasound Imaging", IEEE International Symposium on Industrial Electronics (2006).
Li et al., "In vivo Breast Sound-Speed Imaging with Ultrasound Tomography." Ultrasound in medicine & biology 35.10 (2009): 1615-1628.
Li et al., "An improved automatic time-of-flight picker for medical ultrasound tomography," Ultrasonics 49(1), 61-72 (2009) [doi:10.1016/j.ultras.2008.05.005].
Littrup et al., "Computerized ultrasound risk evaluation (CURE) system: development of combined transmission and reflection ultrasound with new reconstruction algorithms for breast imaging," Acoustical Imaging, 175-182. (2001).
Ma et al., "Multispectral optoacoustic tomography (MSOT) scanner for whole-body small animal imaging," Opt. Express 17(24) , 21414-21426 (2009).
Marmarelis et al., "High-resolution ultrasound transmission tomography," in Medical Imaging, Proc. SPIE 5035, 33-40 (2003) [doi:10.1117/12.479887].
Melvær et al., "A motion constrained cross-wire phantom for tracked 2D ultrasound calibration," CARS , 7(4), 611-620, 2012.
Mercier et. al., "A review of calibration techniques for freehand 3-D ultrasound systems."Ultrasound in medicine & biology 31, No. 2, 143-165 (2005).
Morris et. al, "A Fabry-Perot fiber-optic ultrasonic hydrophone for the simultaneous measurement of temperature and acoustic pressure", J. Acoust. Soc. Am, vol. 125, No. 6, p. 3611, 2009.
Najafi et al., "A robotic wrist for remote ultrasound imaging," Mechanism and Machine Theory, 46(8), 1153-1170 (2011).
Pagoulatos et al., "A Fast Calibration Method for 3-D Tracking of Ultrasound Images using a Spatial Localizer," Ultrasound in Medicine and Biology, 27(9), 1219-1229, 2001.
Patel et al., "An analysis of deep vein thrombosis in 1277 consecutive neurosurgical patients undergoing routine weekly ultrasonography", Journal of Neurosurg, vol. 118, Mar. 2013, pp. 505-509.
Pierrot et al., "Hippocrate: a safe robot arm for medical applications with force feedback", Medical Image Analysis, 3(3), 1999, pp. 285-300.
Poon, T., Rohling, R., "Comparison of calibration methods for spatial tracking of a 3-D ultrasoundprobe." Ultrasound in Medicine and Biology, 31(8),1095-1108, 2005.
Prager et al., "Rapid Calibration for 3-D freehand Ultrasound," Ultrasound in Medicine and Biology, 24 (6), 855-869, 1998.
Prager et al., "Stradx: real-time acquisition and visualization of freehand three-dimensional ultrasound," Medical Image Analysis 3(2), 129-140 (1998) [doi:10.1016/S1361-8415(99)80003-6].
Prager et al., "Automatic Calibration for 3-D Free-Hand Ultrasound," Dep. Eng., Cambridge Univ., 1997.
Prager et al., "Three-dimensional US imaging," Proc. of the Institution of Mechanical Engineers, Part H: J. of Engineering in Medicine 224(2), 193-223 (2010) [doi:10.1243/09544119JEIM586].
Siddon. "Fast calculation of the exact radiological path for a three-dimensional CT array." Medical physics 12.2 (1985): 252-255.
Stotzka et al., "Medical imaging by ultrasound computer tomography," in Medical Imaging, Proc. of SPIE, 4687, 110-119 (2002) [doi:10.1117/12.462144].
Talbot S, "Use of real-time imaging in identifying deep venous obstruction: a preliminary report", Bruit, 1982,7, pp. 41-42.
Treece et al., "High-definition freehand 3-D ultrasound", Ultrasound in Medicine and Biology, 29(4), pp. 529-546, 2003.

(56) References Cited

OTHER PUBLICATIONS

Vanderpool et al., "Prevalence of carpal tunnel syndrome and other work-related musculoskeletal problems in cardiac sonographers", JOEM: Journal of Occupational and Environmental Medicine, vol. 35, Jun. 1993, pp. 97-113.
Vilhchis et al., "A new robot architecture for Tele-Echography", IEEE Transaction on Robotics and Automation, 19(5), 2003, pp. 922-926.
Wang et al., "Photoacoustic tomography: in vivo imaging from organelles to organs," Science 335, 1458-1462 (2012).
Xu et al., "Universal back-projection algorithm for photoacoustic computed tomography," Phys. Rev. E. 71(1), 016706 (2005).
International Search Report and Written Opinion issued in PCT International Application No. PCT/US2015/026538 dated Jul. 1, 2015.
"Cisst libraries and Surgical Assistant Workstation (SAW)," Johns Hopkins University, MD, USA, Available online: https://trac.lcsr.jhu.edu/cisst/wiki/WikiStart (accessed Jul. 2014).
"Deep Vein Thrombosis overview", Society of Interventional , available online: http://www.sirweb.org/patients/deep-vein-thrombosis/.
"DVT overview", WebMD, available online: http://www.webmd.com/dvt/ss/slideshow-deep-vein-thrombosis-overview.
"MTC documentation," Claron Technology, Canada, Available online: http://www.clarontech.com/API/index.html (accessed Jul. 2014).
"Softvue system," Delphinus Medical technologies, MI, USA, Available online: http://www.delphinusmt.com/our-technology/softvue-system (accessed Jul. 2014).
"The URScript programming language," Universal Robots, Denmark, Available online: http://www.wmv-robotics.de/home_htm_files/scriptmanual_en_1.5.pdf (accessed Jul. 2014).
Billings et al., "A hybrid surface/image based approach to facilitate ultrasound/CT registration," Medical Imaging 2011: Ultrasonic Imaging, Tomography, and Therapy, Proc. of SPIE vol. 7968, pp. 79680V-1-79680V-12.
Billings et al., "System for robot-assisted real-time laparoscopic ultrasound elastography," Medical Imaging 2012: Image-Guided Procedures, Robotic Interventions, and Modeling, Proc. of SPIE vol. 8316, pp. 83161W-1-83161W-8.
Edwards, S., et. al., <http://wiki.ros.org/universal_robot>, reached at Jan. 11, 2014.
Kang et al., "Freehand Spatial-Angular Compounding of Photoacoustic Images," Photons Plus Ultrasound: Imaging and Sensing, 2014, Proc. of SPIE vol. 8943, pp. 894361-1-894361-9.
Lusting, SparseMRI Toolbox downloaded from http://www.eecs.berkeley.edu/~mlustig/Software.html. Downloaded: Aug. 1, 2014.
Microsoft. Kinect for Windows. Available online: http://www.microsoft.com/en-us/Kinectforwindows/.
Stolka et al., "Navigation with Local Sensors in Handheld 3D Ultrasound—Initial in-vivo Experience," Medical Imaging 2011: Ultrasonic Imaging, Tomography, and Therapy, Proc. of SPIE vol. 7968, pp. 79681J-1-79681J-9.
Taylor R., Jensen P., Whitcomb L., Barnes A., Stoianovici D., Gupta P., Wang Z., de Juan E., and Kavoussi L., 1999, "A Steady-Hand robotic system for microsurgical augmentation," The International Journal of Robotics Research, 18(12), pp. 1201-1210.
Wang et al., "The Kinect as an interventional tracking system," Medical Imaging 2012: Image-Guided Procedures, Robotics Interventions and Modeling, Proc SPIE vol. 8316; pp. 83160U-1-83160U-6.
Aalamifar et al., "Enabling technologies for robot assisted ultrasound tomography: system setup and calibration." SPIE Medical Imaging. International Society for Optics and Photonics, 2014.
Abolmaesumi et al., "Image-guided control of a robot for medical ultrasound." Robotics and Automation, IEEE Transactions on 18.1, 11-23 (2013).
Ackerman et al., "Online Ultrasound Sensor Calibration Using Gradient Descent on the Euclidean Group," Accepted to International Conference on Robotics and Automation, 2014.
Ackerman et al., "Sensor calibration with unknown correspondence: solving AX=XB using Euclidean-group invariants," in Intelligent Robots and Systems, IEEE/RSJ International Conference, 1308-1313 (2013) [doi:10.1109/IROS.2013.6696518].
Ashfaq, Mohammad. Measuring and Signal Processing Techniques for Ultrasound Computed Tomography. Diss. PhD thesis. Bochum, Germany: Ruhr University, 2007.
Bauer et al., "Multi-modal suface registration for markerless initial patient setup in radiation therapy using Microsoft's Kinect sensor", IEEE International Conference on Computer Vision Workshops (ICCV), Barcelona, Spain, 2011, pp. 1175-1181.
Benavidez et al., "Mobile robot navigation and target tracking system", Proceedings of the 6th International Conference on system of Systems Engineering: SoSE in Cloud Computign, Smart Grid, and Cyber Security, SoSE 2011, Albuquerque, NM, USA, 2011; pp. 299-304.
Besl et al., "A method for registration of 3-d shapes", IEEE Transactions on Pattern Analysis and Machine Intelligence, vol. 14, No. 2,1992, pp. 239-256.
Boctor et al., "A Novel Closed Form Solution for Ultrasound Calibration," IEEE Int Symp. on Biomedical Imaging, 527-530, 2004.
Boctor et al., "A dual-armed robotic system for intraoperative ultrasound guided hepatic ablative therapy: a prospective study," in Robotics and Automation, Proc. ICRA 3, 2517-2522, (2004) [doi:10.1109/ROBOT.2004.1307440].
Brecht et al. Whole-body three-dimensional optoacoustic tomography system for small animals. J Biomed Opt 14, 064007 (2009).
Bronstein et al., "Reconstruction in diffraction ultrasound tomography using nonuniform FFT," IEEE Transactions on Medical Imaging 21(11), 1395-1401 (2002) [doi:10.1109/TMI.2002.806423].
Cleary et al., "Electromagnetic Tracking for Image-Guided Abdominal Procedures: Overall System and Technical Issues," IEEE EMBS, 6748-6753, 2005.
Conti et al., "Interface design and contral strategies for a robot assisted ultrasonic examination system", Experimental Robotics,Springer Tracts in Advanced Robotics, vol. 79, 2014, pp. 97-113.
De Martino et al., "Impact of screening versus symptomatic measurement of deep vein thrombosis in a nationalquality improvement registry", Journal of Vascular Surgery, 2012(10), pp. 1045-1051.
Detmer et al., "3D ultrasonic image feature localization based on magnetic scanhead tracking: in vitro calibration and validation," Ultrasound in Medicine and Biology, 20 (9), 923-936, 1994.
Drost et al., "Model Globally, match locally: efficient and robust 3D object recognition", IEEE Conference on Computer Vision and Pattern Recognition(CVPR), 2010, San Francisco, CA, USA, 2010, pp. 998-1005.
Duric et al., "Development of ultrasound tomography for breast imaging: Technical assessment." Medical Physics 32.5 (2005): 1375-1386.
Duric et al., "Detection of breast cancer with ultrasound tomography: First results with the Computed Ultrasound Risk Evaluation (CURE) prototype." Medical physics 34, No. 2 (2007): 773-785.
Fenster et al., "3D US imaging in image-guided intervention," in Advancements and Breakthroughs in US Imaging, Ch. 1, INTECH (2013) [doi:10.5772/55230].
Glide et al., "Novel approach to evaluating breast density utilizing ultrasound tomography." Medical physics 34.2 (2007): 744-753.
Gooding et al., "Temporal calibration of freehand three-dimensional ultrasound using image alignment," Ultrasound in medicine & biology 31(7), 919-927 (2005) [doi:10.1016/j.ultrasmedbio.2005.04.007].
Gornik et al., "Duplex ultrasound in the diagnosis of lower-extremity deep venous thrombosis", Circulation, Journal of the American Heart Association,2014; 129,pp. 917-921.
Greenleaf et al., "Computerized tomography with ultrasound." Proceedings of the IEEE 71.3 (1983): 330-337.
Guo et al., "Active Ultrasound Pattern Injection System (AUSPIS) for Interventional Tool Guidance," PloS one, vol. 9, e104262 (2014).

* cited by examiner

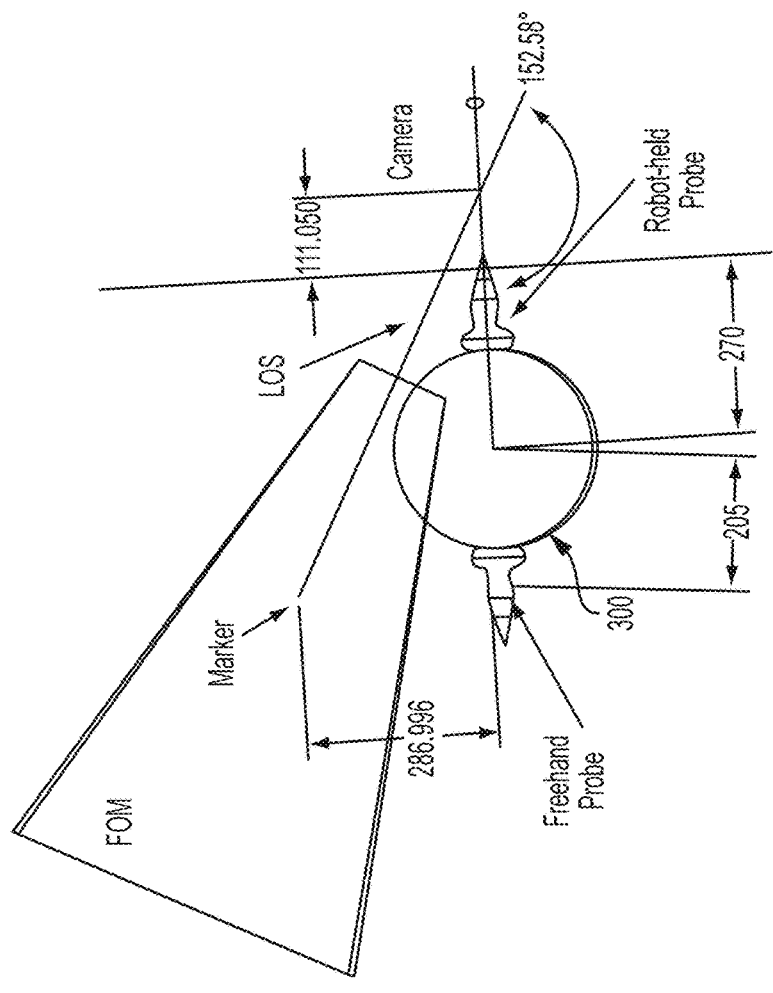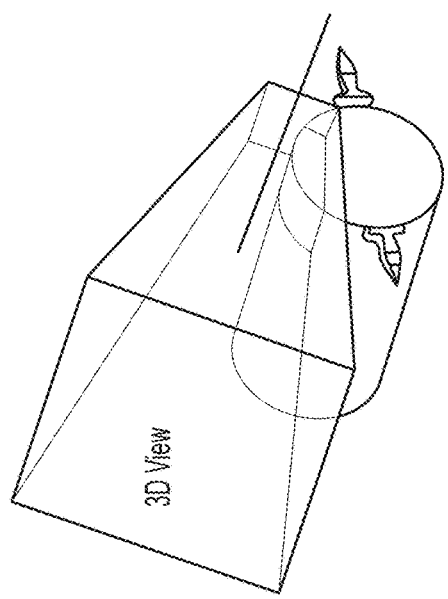
FIG. 4

|  | Calibration sets # | Evaluation sets # | Norm (mm) | X (mm) | Y (mm) | Z (mm) |
|---|---|---|---|---|---|---|
| Freehand US bor | 45 | 12 | 4.30 | 1.20 | 0.97 | 3.99 |
| Freehand US aor | 45 (36)* | 12 | 4.12 | 1.17 | 0.99 | 3.80 |
| Robot-side US bor | 44 | 12 | 1.79 | 0.69 | 1.25 | 1.05 |
| Robot-side US aor | 44 (35) | 12 | 1.73 | 0.67 | 1.21 | 0.99 |
| Hand-eye bor | 28 | 10 | 2.52 | 1.50 | 1.54 | 1.23 |
| Hand-eye aor | 28 (23) | 10 | 2.23 | 1.31 | 1.43 | 1.02 |

\* The number in parenthesis refers to the number of sets after the outlier removal step.

FIG. 19

|  | Corner A (mm) | Corner B (mm) | Corner C (mm) | Corner D (mm) |
|---|---|---|---|---|
| Freehand US bor | 2.93 | 3.37 | 3.28 | 2.99 |
| Freehand US aor | 2.79 | 2.94 | 2.86 | 2.98 |
| Robot-side US bor | 1.22 | 1.93 | 1.72 | 1.47 |
| Robot-side US aor | 1.07 | 2.00 | 1.66 | 1.40 |

FIG. 20

|  | *Corner A (mm)* | *Corner B (mm)* | *Corner C (mm)* | *Corner D (mm)* |
|---|---|---|---|---|
| Stationary – bor | 8.66 | 8.07 | 7.06 | 7.73 |
| Stationary – aor | 7.42 | 6.91 | 6.05 | 6.62 |
| Dynamic – bor | 6.89 | 6.68 | 5.85 | 6.08 |
| Dynamic – aor | 5.89 | 5.71 | 5.06 | 5.26 |

FIG. 21

|  | Correlation coefficient | RMSE (5 iterations) | RMSE (30 iterations) | Mean time of iteration (ms) |
|---|---|---|---|---|
| Phantom leg | 0.9493 | 0.0087 | 0.0047 | 13.87 |
| Human leg | 0.8809 | 0.0026 | 0.0035 | 15.73 |

| Phantom | Corners (Lateral, Axial) (mm) | Repeatability (mm) |
|---|---|---|
| AE | (0, 0), (0, 90), (58.5, 0), (58.5, 90) | 0.37, 0.60, 0.48, 0.71 |
| CW | (0, 0), (0, 90), (58.5, 0), (58.5, 90) | 1.66, 2.82, 1.55, 3.11 |

FIG. 36 A-F

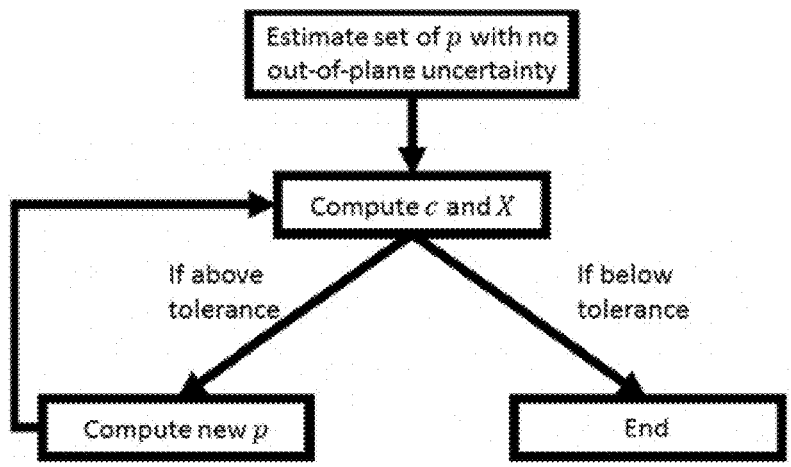
FIG. 40
| N=50 | Noise = 0mm | 0.1mm | 0.2mm | 0.3mm | 0.4mm | 0.5mm |
|---|---|---|---|---|---|---|
| Elevational = 0mm | 0±0 | 0.03±0 | 0.06±0.01 | 0.09±0.01 | 0.12±0.02 | 0.15±0.02 |
| 2mm | 0.14±0.07 | 0.16±0.11 | 0.19±0.10 | 0.20±0.08 | 0.27±0.11 | 0.27±0.07 |
| 4mm | 0.17±0.14 | 0.16±0.12 | 0.23±0.15 | 0.23±0.12 | 0.25±0.10 | 0.29±0.13 |
FIG. 41
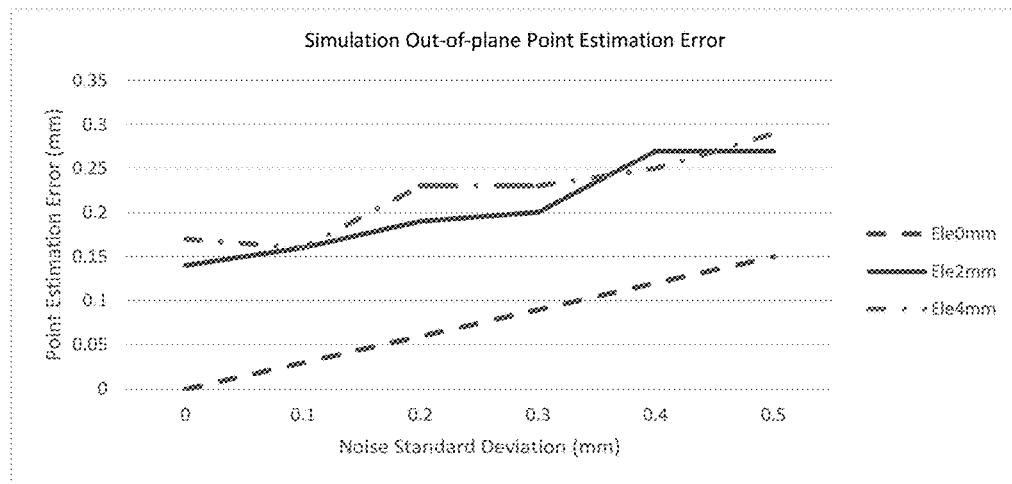
FIG. 42

| N=50 | Noise = 0mm | 0.1mm | 0.2mm | 0.3mm | 0.4mm | 0.5mm |
|---|---|---|---|---|---|---|
| Elevational = 0mm | 0±0, 0±0 | 0.02±0.01, 0.03±0.02 | 0.04±0.04, 0.06±0.04 | 0.05±0.04, 0.08±0.05 | 0.09±0.06, 0.11±0.07 | 0.09±0.07, 0.12±0.08 |
| 2mm | 0.57±0.29, 0.36±0.43 | 0.69±0.48, 0.65±0.62 | 0.70±0.45, 0.63±0.51 | 0.86±0.56, 0.56±0.55 | 1.20±0.59, 0.94±0.61 | 1.19±0.65, 0.80±0.61 |
| 4mm | 0.23±0.15, 0.15±0.09 | 0.29±0.18, 0.21±0.18 | 0.41±0.24, 0.32±0.24 | 0.57±0.29, 0.36±0.25 | 0.63±0.41, 0.45±0.26 | 0.83±0.51, 0.57±0.51 |

| N=50 | Noise = 0mm | 0.1mm | 0.2mm | 0.3mm | 0.4mm | 0.5mm |
|---|---|---|---|---|---|---|
| Elevational = 0mm | 0±0 | 0.01±0 | 0.02±0.01 | 0.03±0.01 | 0.04±0.02 | 0.04±0.02 |
| 2mm | 0.12±0.07 | 0.14±0.10 | 0.14±0.09 | 0.18±0.10 | 0.22±0.12 | 0.22±0.12 |
| 4mm | 0.10±0.08 | 0.10±0.07 | 0.14±0.09 | 0.14±0.09 | 0.16±0.08 | 0.20±0.11 |

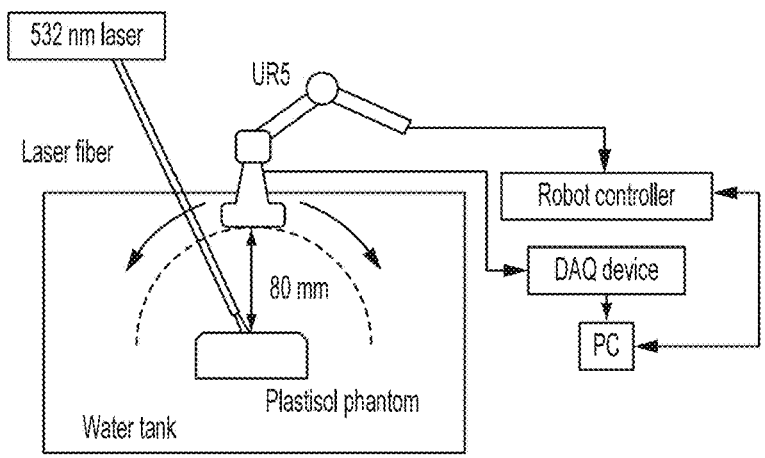
FIG. 63
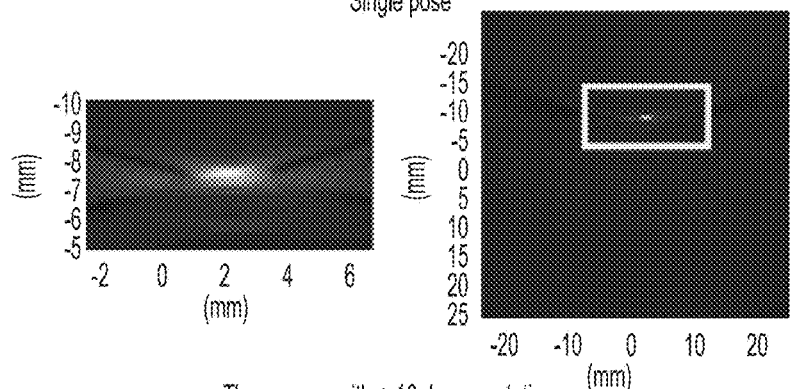
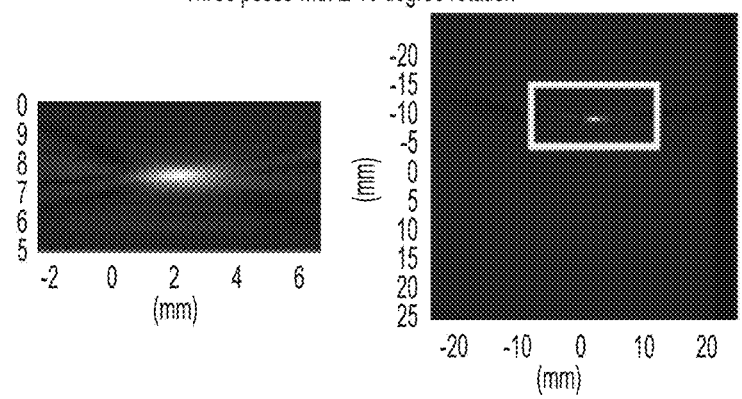
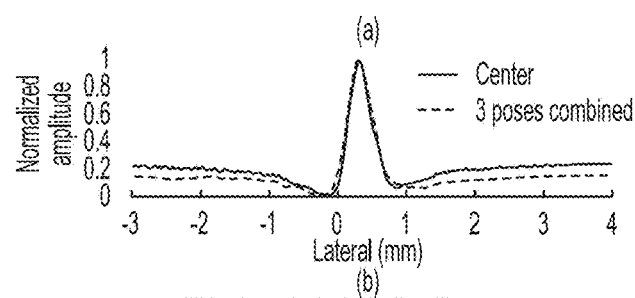
FIG. 64A, 64B

ROBOT ASSISTED ULTRASOUND SYSTEM

This application claims priority to U.S. Provisional Application No. 61/981,069 filed Apr. 17, 2014, the entire content of which is hereby incorporated by reference.

This invention was made with Government support of Grant No. IIS-1162095, awarded by the National Science Foundation. The U.S. Government has certain rights in this invention.

BACKGROUND

1. Technical Field

The field of the currently claimed embodiments of this invention relates to ultrasound systems, and more particularly to a robotic assisted ultrasound system.

2. Discussion of Related Art

Ultrasound machines are relatively inexpensive, are portable, and more importantly, do not produce ionizing radiation. The ultrasound penetration depth typically ranges up to 15 cm. The thicker the tissue, the more attenuation is caused, and consequently, the noisier are the images that are obtained. This is why ultrasound imaging cannot be used for thick tissues or obese patients. One of the techniques to overcome this limitation is called transmission ultrasound or ultrasound tomography. In this technique, unlike the conventional method in which both the transmitter and receiver are placed at the same location, one transducer is used as the transmitter and one is used as the receiver, with the imaged tissue placed in the middle. Therefore, the penetration depth is doubled. Reference [1], for instance, proposes an ultrasound computed tomography prototype where a tank of water with many identical transducers in the wall of the tank is considered for acquiring tomographic imaging. Reference [2] has covered many of such systems. Even though promising results have been reported using the ultrasound transmission tomography systems, more development is needed in this field to enhance the spatial resolution and speed up the process [2]. Furthermore, requiring the scanned area to be inside a water tank is inconvenient and limits the possible areas that can be scanned. In addition, using vast number of transducers instead of the existing ultrasonic imaging systems to enable this technology is another disadvantage. As a result, this technique has not gained significant attention so far. Accordingly, there remains a need for improved ultrasound systems, including, but not limited to, improved ultrasound tomography systems.

SUMMARY

According to some embodiments of the invention, a robot-assisted ultrasound system includes a first ultrasound probe, a robot comprising a manipulator arm having a tool end, and a second ultrasound probe attached to the tool end of the manipulator arm. The robot-assisted ultrasound system further includes a robot control system configured to control at least one of a position or a pose of the second ultrasound probe based on a contemporaneous position and pose of the first ultrasound probe, and an ultrasound processing and display system configured to communicate with at least one of the first and second ultrasound probes to receive and display an ultrasound image based on the first and second ultrasound probes acting in conjunction with each other.

According to some embodiments of the invention, the robot-assisted ultrasound system further includes a tracking system configured to track the relative position and pose of the first and second ultrasound probes. The tracking system is adapted to communicate with the robot control system. The tracking system can be an optical tracking system comprising an optical detection system attached to the manipulator arm of the robot.

According to some embodiments of the invention, the robot-assisted ultrasound system further includes a second manipulation arm of at least one of the robot or a second robot, wherein the first ultrasound probe is attached to a tool end of the second manipulator arm. The robot control system can be configured to control at least one of a position or a pose of the first ultrasound probe based on a contemporaneous position and pose of the second ultrasound probe. The robot control system can be configured to cooperatively control at least one of a position or a pose of the first ultrasound probe with a user.

BRIEF DESCRIPTION OF THE DRAWINGS

Further objectives and advantages will become apparent from a consideration of the description, drawings, and examples.

FIG. 4 shows a simulation study of the camera and rigid body positions;

FIG. 19 shows the calibration evaluation results before outlier removal (bor) and after outlier removal (aor);

FIG. 20 shows the US calibrations' repeatability evaluation results;

FIG. 21 shows overall system repeatability experiments' results;

FIG. 36A shows B-mode images of the CW phantom acquired at 4 cm depth, normal angle and in-focus condition;

FIG. 36B shows B-mode images of the CW phantom acquired at 8 cm depth, large incident angle and off-focus condition;

FIG. 36C shows B-mode images of the AE phantom acquired at 4 cm depth, normal angle and in-focus condition;

FIG. 36D shows B-mode images of the AE phantom acquired at 4 cm depth, normal angle and in-focus condition, wherein the AE is enabled;

FIG. 36E shows B-mode images of the AE phantom acquired at 8 cm depth, large incident angle and off-focus condition;

FIG. 36F shows B-mode images of the AE phantom acquired at 8 cm depth, large incident angle and off-focus condition, wherein the AE is enabled;

FIG. 40 shows the calibration algorithm workflow according to some embodiments of the invention;

FIG. 41 shows a table of the simulated out-of-plane point estimation error (mm);

FIG. 42 plots the simulated out-of-plane estimation error (mm);

FIG. 63 is a schematic illustration of the experimental setup according to some embodiments of the invention;

FIG. 64A shows a reconstructed image of a single pose and three poses with consecutive 10 degree rotation angle; and FIG. 64 B shows the profile of the center pose and three poses combined result.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

An embodiment of the current invention is directed to a system which uses two conventional ultrasound (US) probes, a combination of a human operated probe and a robot operated one, which can be used to offer higher imaging depth, and to enable ultrasound tomography imaging. Advantages of having a robot in the system can include precise alignment and ease of operation.

Figure 1:
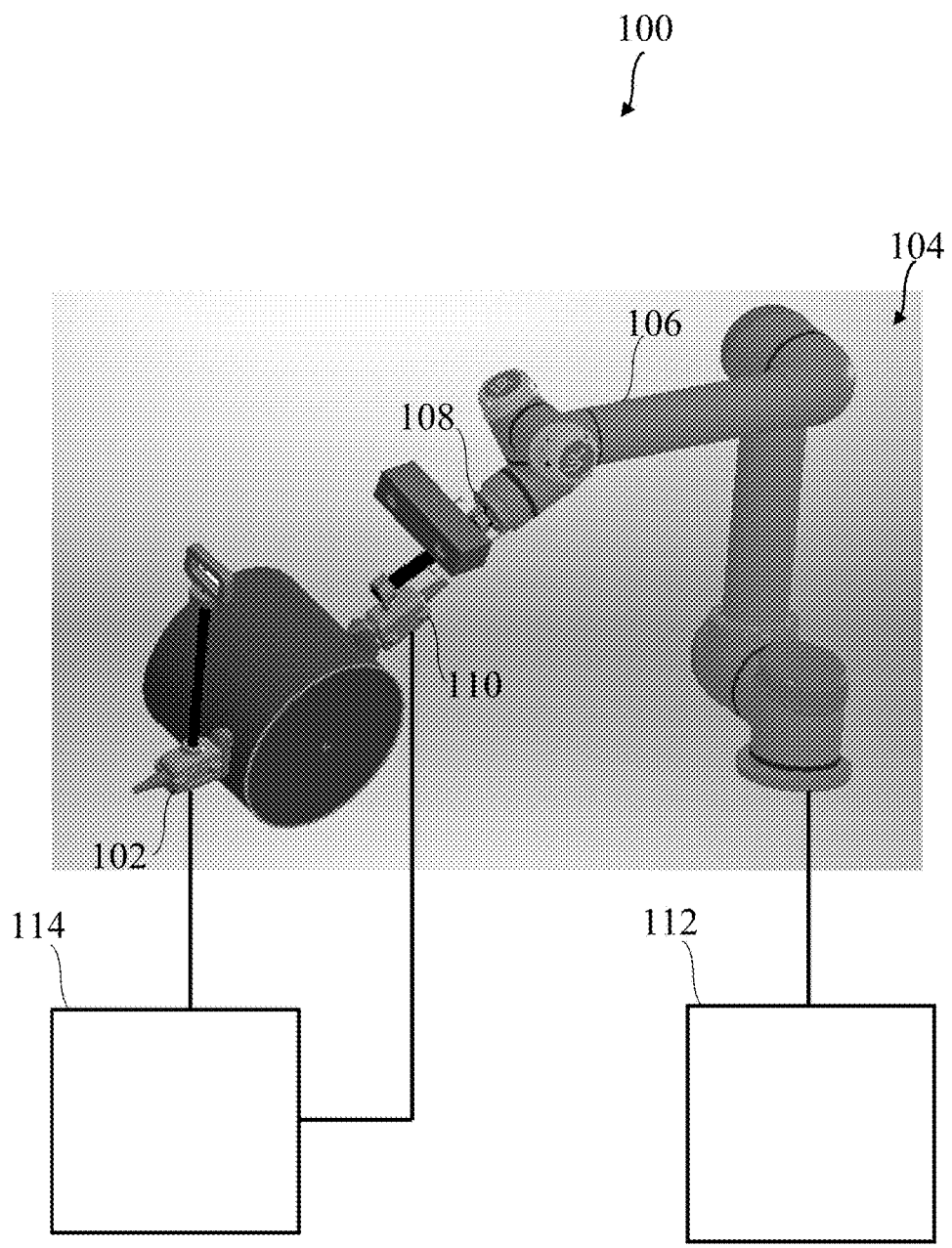
FIG. 1 is a schematic illustration of a robot-assisted ultrasound system according to some embodiments of the invention.

FIG. 1 is a schematic illustration of a robot-assisted ultrasound system 100 according to some embodiments of the invention. The robot-assisted ultrasound system 100 includes a first ultrasound probe 102, a robot 104 comprising a manipulator arm 106 having a tool end 108, and a second ultrasound probe 110 attached to the tool end 108 of the manipulator arm 106. The system also includes a robot control system 112 configured to control at least one of a position or a pose of the second ultrasound probe 110 based on a contemporaneous position and pose of the first ultrasound probe 102. An ultrasound processing and display system 114 is configured to communicate with at least one of the first and second ultrasound probes 102, 110 to receive and display an ultrasound image based on the first and second ultrasound probes 102, 110 acting in conjunction with each other.

Figure 2:
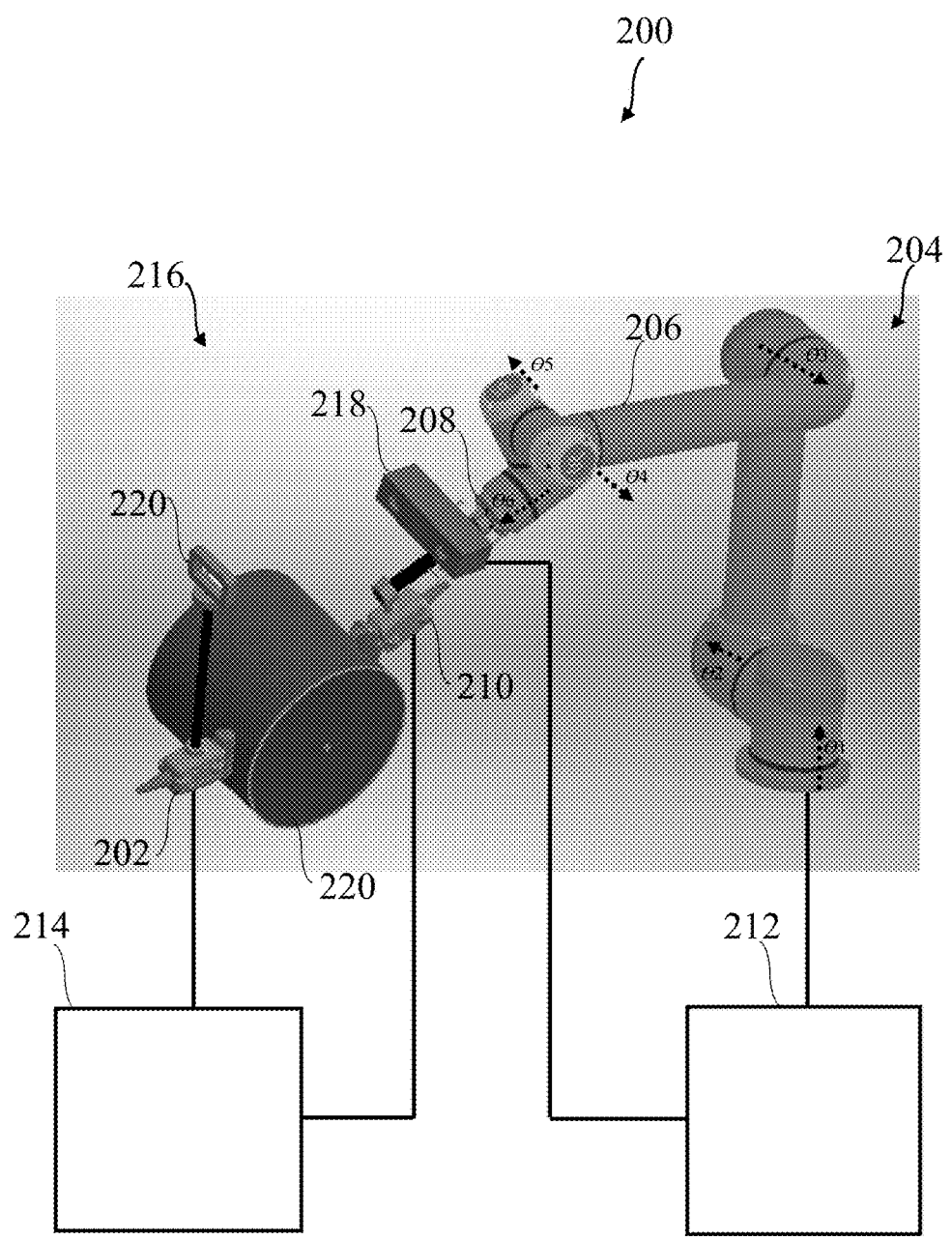
FIG. 2 is a schematic illustration of a robot-assisted ultrasound system according to some additional embodiments of the invention.

FIG. 2 is a schematic illustration of a robot-assisted ultrasound system 200 according to some additional embodiments of the invention, wherein like reference numerals as in FIG. 1 indicate like features. In addition to the features described above, the robot-assisted ultrasound system 200 includes a tracking system 216 configured to track the relative position and pose of the first and second ultrasound probes 202, 210. The tracking system 216 is adapted to communicate with the robot control system 212. The tracking system 216 can be an optical tracking system comprising an optical detection system 218 attached to the manipulator arm 206 of the robot 204, as shown in FIG. 2. The tracking system can comprise an optical marker 220 attached to the first ultrasound probe.

According to some embodiments of the current invention, the robot control system 212 is configured to provide a mirror mode such that motion of the second ultrasound probe 210 mirrors motion of the first ultrasound probe 202. Each of the first and second ultrasound probes 202, 210 is configured to operate in both transmit and receive mode to detect reflected ultrasound signals transmitted from the same ultrasound probe.

According to some embodiments of the invention, the robot control system is configured to align the first and second ultrasound probes 202, 210 with a body of interest 220 therebetween. The first and second ultrasound probes 202, 210 are adapted to operate in transmit mode such that the robot-assisted ultrasound system is an ultrasound tomography system.

According to some embodiments of the invention, one of the first and second ultrasound probes comprises a dedicated ultrasound transmitter and the other of the first and second ultrasound probes comprises a dedicated ultrasound receiver. The robot control system 212 can be further configured to align the first and second ultrasound probes 202, 210 based at least partially on a received ultrasound signal spatial profile. The term ultrasound probe is considered to include any probe used for ultrasound detection and/or imaging, including probes that initiate a photoaccoustic effect, for example, lasers.

Figure 3:
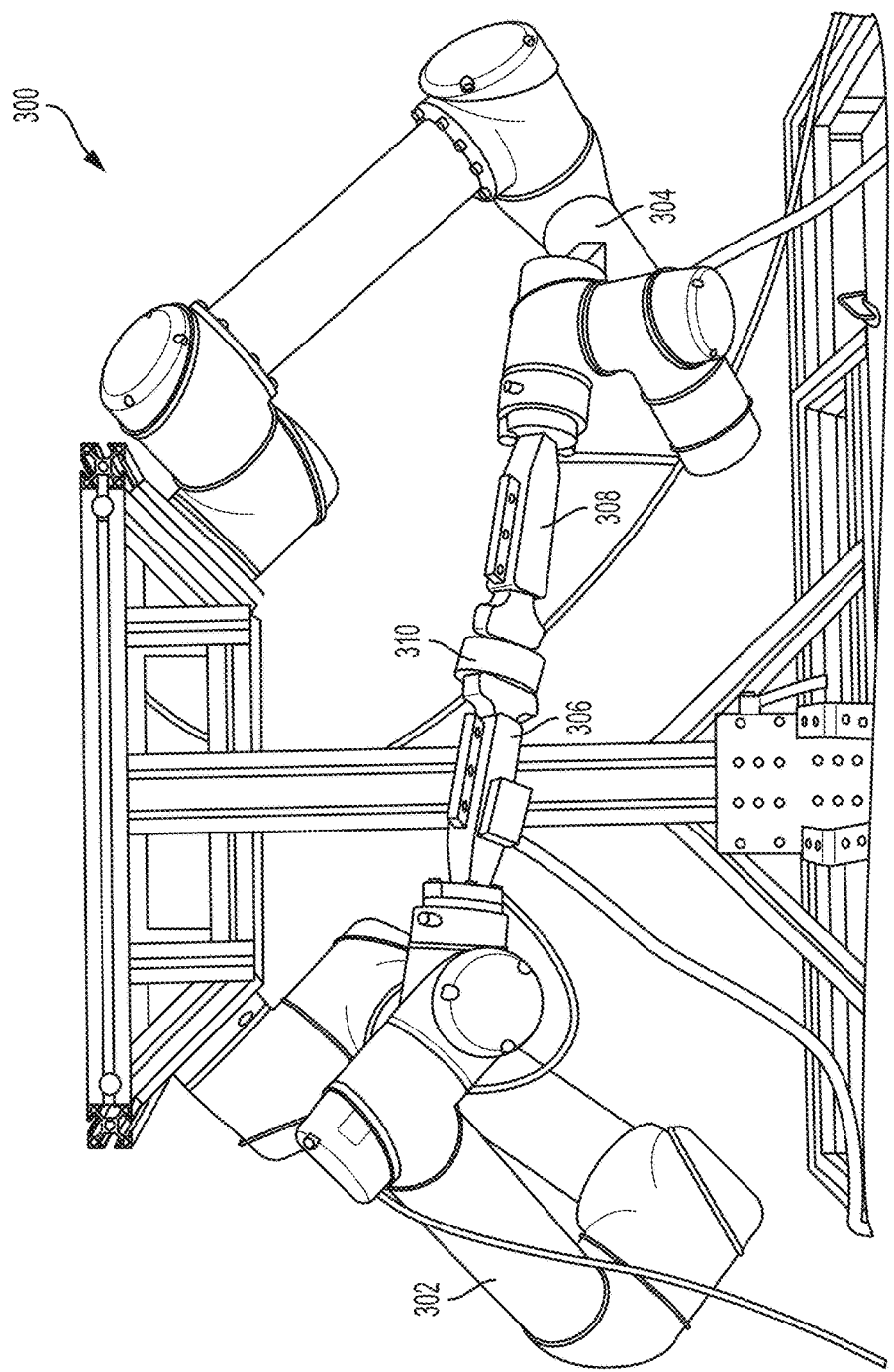
FIG. 3 shows a schematic illustration of a robot-assisted ultrasound system comprising two manipulation arms.

As shown in FIG. 3, according to some embodiments of the invention, the robot-assisted ultrasound system 300 includes a first manipulation arm 302 and a second manipulation arm 304. The second manipulation arm 304 may be part of the same robot as the first manipulation arm 302, or part of a different robot. A first ultrasound probe 306 may be attached to the first manipulation arm 302, and a second ultrasound probe 308 may be attached to the second manipulation arm 304. An acoustic coupling medium or region of interest 310 may be placed between the first ultrasound probe 306 and the second ultrasound probe 308. The first ultrasound probe 306 may be controlled by the robot, or it may be cooperatively or tele-operatively controlled by a user and the robot. In the cooperative control paradigm, the operator and the robot both hold the surgical instrument [3]. The force exerted by the operator guides the robot to comply with the operator's movement. Using various control modes, it can provide precise, tremor-free, smooth, and steady manipulation. The result will be a manipulation system with the precision and sensitivity of a machine, but with the manipulative transparency and immediacy of hand-held instruments that the surgeon uses comfortably every day.

Use of robotics in ultrasound image acquisition has been reported in the literature. For example, a robotic ultrasound system for the neck has been developed in which the operator, a developed image-guided software tool, and the robot controller share the control of one ultrasound probe [4]. A similar tele-operated system for abdominal ultrasonography has also been proposed [5]. However, none of the conventional systems provide the use of robotics for tomographic purposes. To the best of our knowledge, this is the first time a robotic ultrasound tomography system has been presented. In robotic ultrasound tomography, one of the major challenges is to have the two probes properly aligned. Two ultrasound calibrations and one hand-eye calibration may be required to enable tracking. The nature of this system has made the ultrasound calibration a challenging task.

Ultrasound calibration is the procedure through which the transformation from a (typically) tracked sensor, which is rigidly attached to an ultrasound probe, to the ultrasound image coordinate system is determined. Usually, a fiducial marker is imaged by the ultrasound probe from different angles and at the same time the position and orientation of the tracked sensor is measured. The relationship between these two data sets is used to find the unknown transformation. It is possible to use only a point as the fiducial, or a line, several points, a pointer, or more complicated calibration phantoms consisting of several points, lines or planes. Reference [6] provides an extensive summary and comparison of different methods of ultrasound calibration.

An overview of the system according to an embodiment of the current invention is provided and system components are described. FIG. 2 shows an overview of the robot assisted ultrasound tomography system according to some embodiments of the invention. The freehand probe is operated by a sonographer or a technician. It can be tracked by a tracking system installed on the robot side. The appropriate movement of the robot-held probe can be calculated and commanded to the robot such that the robot-held probe moves in compliance with the freehand one. Below, the components of such a system are explained in more details.

Two ultrasound machines may be utilized according to some embodiments of the current invention to enable simultaneous operation of both probes. In an embodiment, two Ultrasonix machines (Ultrasonix Inc., Richmond, British Columbia, Canada) are used. Two identical 60 mm linear array probes are used. One of the probes, referred to herein as the freehand probe, is operated by the technician and the other probe, referred to herein as the robot-held probe, is attached to the robotic arm to track and follow the motion of the freehand probe.

For tracking, an external tracking system is required for some embodiments. The first thing to consider for the external tracker is finding an appropriate place for it in the system's workspace. According to some embodiments of the invention, the tracker is placed on the robot arm. This has the following advantages: 1) there is no limitation on workspace due to the tracker's limited field of view (FOV), 2) it can provide tomographic images from the tracker to compensate for truncated tomography caused by the small FOV of the ultrasound image, and 3) the system will be more portable.

We selected a MicronTracker SX60 (Claron Technology Inc., Toronto, ON, Canada) which provides real-time images of the scene (visible light functionality), has a small footprint, is ultra-light (camera+case<500 grams), and has passive, easily printable markers and low cost stereo cameras. The camera's range of measurement is 115×70×55 cm and the maximum measurement rate is 48 Hz. The camera's calibration accuracy is 0.25 mm. The tracker is connected to a PC through IEEE1394b (Firewire) with a speed of 800 Mb/s. In its range of measurement, the MicronTracker can detect the 3D position of Xpoints that are at least 2.5 mm in diameter.

A robotic arm is used which can precisely reach every point in the workspace and can provide all of the orientations. In an embodiment, a low-noise, flexible, and lightweight robot is also preferred for this application. As shown in FIG. 3, we used a UR5 robotic arm (Universal Robots Inc., Odense, Denmark) which is a lightweight (18.4 kg) and noiseless robot with six degrees of freedom. All of the six joints have a range of rotation of ±360 degrees. The robot tooltip can reach 850 mm from the center of the base with a repeatability of ±0.1 mm and with a speed of up to 1 m/s [7].

The robot comes with a controller and a teach pendant (or control panel). The control panel has a software tool called Polyscope from which the robot can be controlled by the user. In general, the robot can be controlled in 3 modes: GUI, URscript, and C API. The GUI is available through the polyscope software on the control panel and gives direct access to the control of the joint angles or the tooltip position. It is also possible to save the positions as a program and run the program automatically. The URscript is the language provided by the company with built-in variables and functions. It is also possible to control the robot using the low level C-API. However, the user needs to provide their own robot controller and specify all of the parameters such as each joint's position, speed, and acceleration.

UR5 also comes with its own simulator called URsim. In addition, the experimental version of the Universal Robots ROS simulator has been recently implemented [8].

To enable the tracking and also robot-held probe operation, two mechanical interfaces are designed and manufactured. According to some embodiments, the marker is rigidly attached on top of the probe so that it is visible in the tracker's range of measurement. The camera is configured to view the same scene that the ultrasound probe is imaging; hence the camera is placed at the end-effector just before the robot-held probe. It may also be desirable that the area that is scanned not obstruct the camera's view of the marker on the freehand probe. Hence it may be placed at a distance with respect to the robot-held probe that is in contact with the tissue. When the approximate desired position of camera is determined, we then design the freehand rigid body such that 1) the marker is in the range of measurement of the camera, and 2) the marker is in the line of sight of camera.

At this stage, it is assumed that the area that is scanned is cylindrical with a maximum diameter of 30 cm. Based on this assumption and considering the camera's range of measurement volume, the camera's position and angle on the end-effector and the marker position on the freehand probe are determined based on a sample simulation study shown in FIG. 4.

Figure 5:
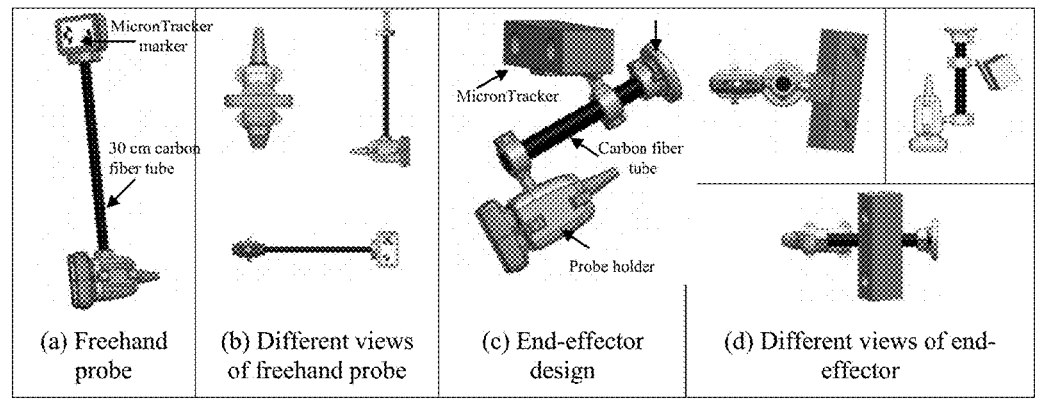
FIG. 5 illustrates a freehand rigid body and end-effector design.

A probe holder is designed and built using acrylonitrile butadiene styrene (ABS) material and solid 3D printing. A hole is designed on top of the probe holder to insert a 30 cm rod complying with the design shown in FIG. 4. To ensure both rigidity and lightness we use a carbon fiber tube with a 0.5 inch inside diameter. The marker is attached on the top of the tube as shown in FIGS. 5A and 5B.

In order to attach the tracker's camera and robot-held probe, we design a separate end-effector which can be mounted on the robot arm. FIGS. 5C and 5D show its components. Since the camera's weight should be tolerated on the end-effector, the carbon fiber tube, used for the end-effector, has a larger diameter (0.75 inch) in comparison with the freehand rigid body, to ensure more rigidity. The whole end-effector weighs around 1 kg and is less than the maximum possible payload on the robot, which is 5 kg.

Figure 6A:
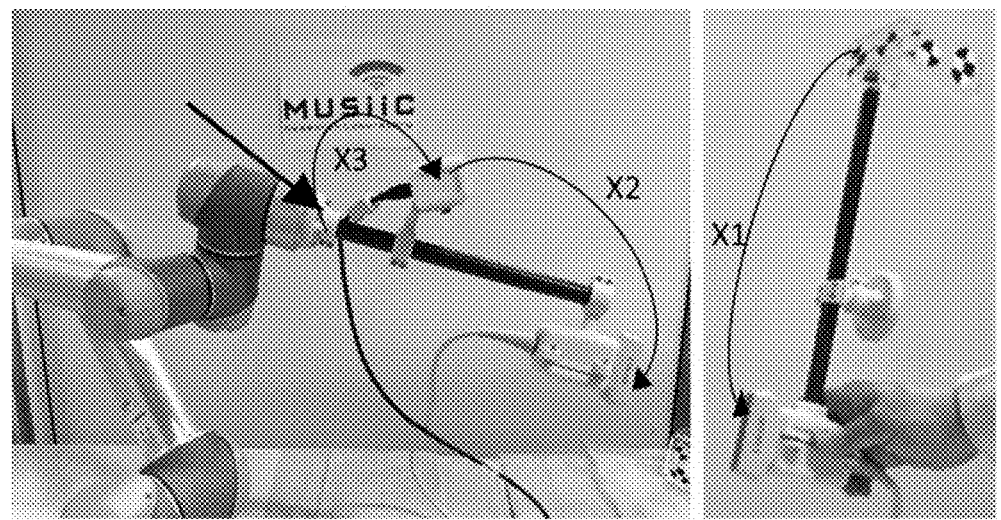
FIG. 6A shows unknown transformations found through ultrasound calibrations.

Two ultrasound calibrations are performed to enable the tracking: the transformation from the freehand probe marker coordinate system to its ultrasound image coordinate system, X1, and the transformation from the tracker's camera coordinate system to the robot-held probe ultrasound image, X2, as shown in FIG. 6A. In addition to the ultrasound calibrations, another calibration may be required. Referred to herein as the hand-eye calibration, it determines the transformation from the robot tooltip to the MicronTracker's coordinate system, X3. The hand-eye calibration may be required for the operation of the overall system.

Figure 6B:
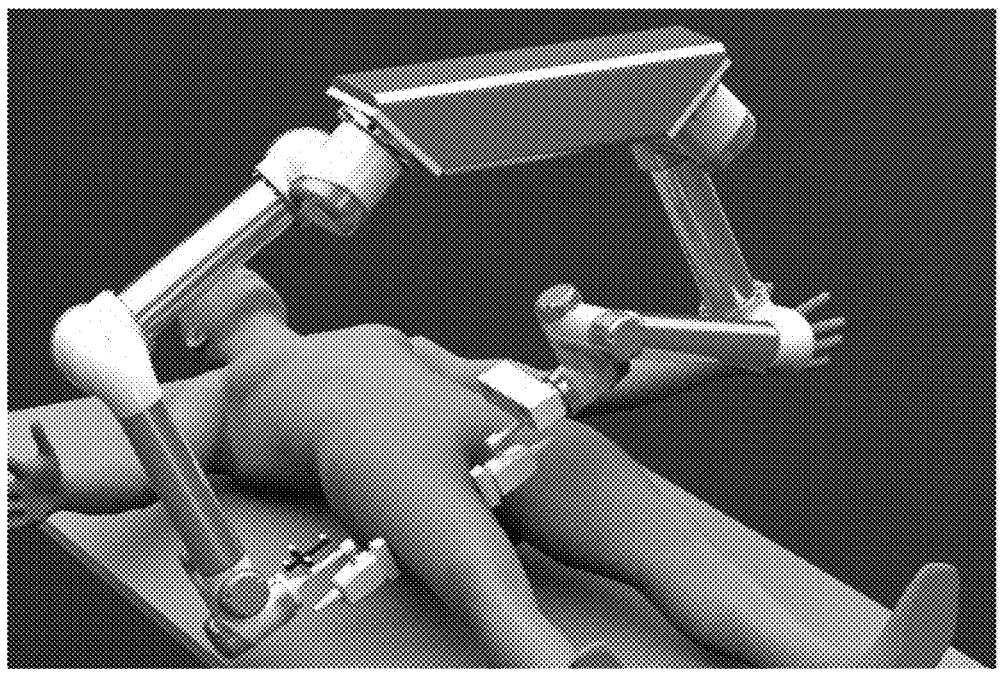
FIG. 6B shows a schematic illustration of an ultrasound tomography system according to some embodiments of the invention.
Figure 6C:
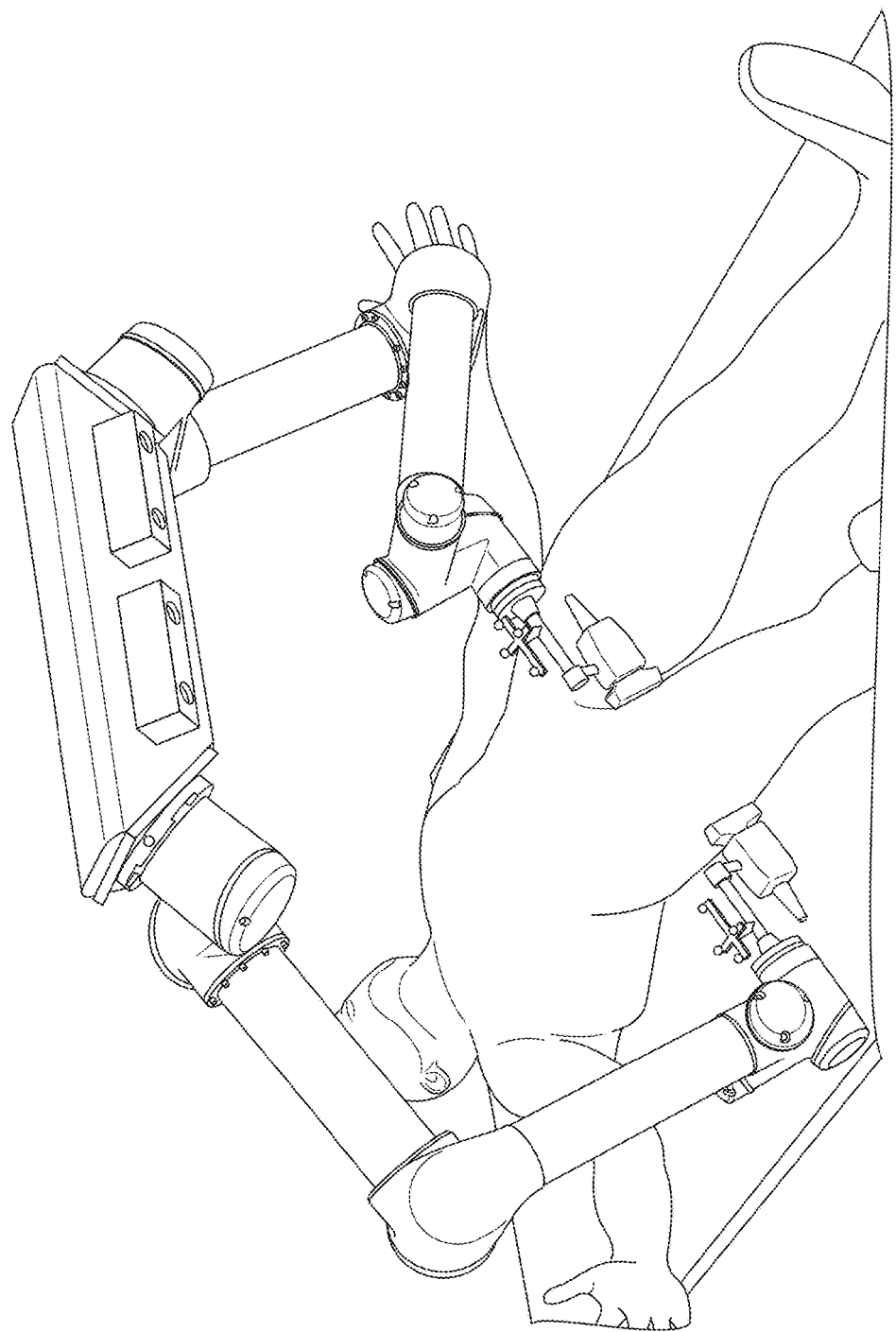
FIG. 6C shows a schematic illustration of an ultrasound tomography system according to some additional embodiments of the invention.

As described with regard to FIG. 3, according to some embodiments of the invention, the robot-assisted ultrasound system includes two manipulation arms, with an ultrasound probe attached to the end of each arm. FIG. 6B shows a schematic illustration of an ultrasound tomography system according to some embodiments of the invention. While both robot arms can be calibrated to each other and we can rely on the arms' encoders to localize both ultrasound probes, the tracking camera attached to one arm can provide redundant tracking. It can also help in calibrating both arms intraoperatively. This tracking camera configuration can also include a projector to visualize and guide the user or to help generate surface information need for registration tasks. We can also utilize the ultrasound energy profile to fine tune the tracking and to accurately aim both probes to the center of the common beam profile. FIG. 6C shows a schematic illustration of an ultrasound tomography system according to some additional embodiments of the invention. This embodiment uses a tracking camera attached to the base of the robot. The camera can be, in addition to an optical tracking device, a Kinect-like device to provide additional surface information or RGB projection guidance.

The ultrasound calibration method should be chosen carefully for such system because of several factors: 1) The camera has a small range of measurement; 2) the marker is attached at a height with respect to the probe; 3) the camera is attached at a distance with respect to the probe. Factors 2 and 3 imply that when the probe rotates a certain degree, the observed rotation from the marker or camera's points of view is larger, i.e., the probe's range of motion during calibration is limited. We chose the point calibration method as it is more straightforward than other types of ultrasound calibration and can more easily alleviate the limitations on the system. However, the embodiments of the present invention are not limited to the point calibration method, and other calibration methods may be employed.

Figures 7A, 7B:
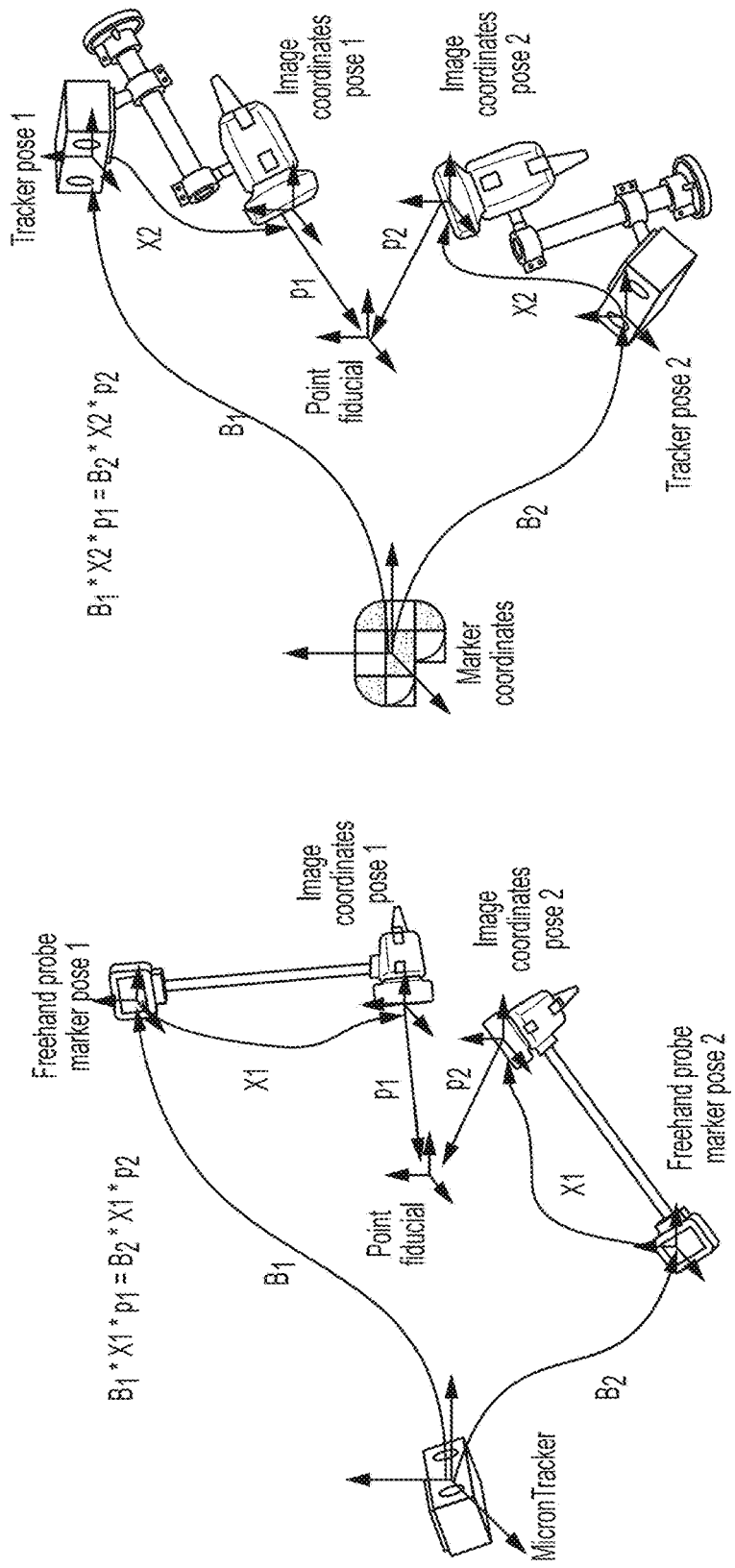
FIG. 7A shows point calibration coordinate systems for the freehand ultrasound calibration design.
FIG. 7B shows point calibration coordinate systems for the robot-held ultrasound calibration design.

In the point calibration, the following equation holds for two instances of time:

$$B_i X p_i = B_j X p_j \quad (1)$$

where $B_i$ and $B_j$ are the transformations from tracker to the tracked sensor at times i and j; X is the transformation from tracked sensor to ultrasound image coordinate system; and $p_i$ and $p_j$ are positions of the point element in the US image. The coordinate systems' diagrams for the two ultrasound calibrations are shown in FIGS. 7A and 7B. FIG. 7A shows the freehand ultrasound calibration diagram, and FIG. 7B shows the robot-held ultrasound calibration diagram.

To solve Equation 1 for X, a gradient decent solver is used which is presented in [9]. In summary, an initial X is given to the algorithm. The algorithm finds the cloud of points based on current X, and then finds the corresponding cost function, based on which a new X is calculated using gradient decent. The above procedure is repeated and consequently, the cloud of points shrinks iteratively until it converges. To determine convergence, two thresholds for translation and rotation are set. The algorithm converges when the difference between the two consecutive X's is less than the thresholds. Refer to [9] for more details.

In this section, the experiment setups, data collection procedures, and evaluation results for the two ultrasound calibrations are provided. The procedure to find X1 is called freehand calibration and the one for X2 is called robot-held calibration.

Since the ultrasound machine and the PC that records tracker poses are not synchronized, either a temporal calibration may be done or data collection may be done when all the components are at a fixed position. We choose the latter and the robotic arm is used to fix the probes' positions in both calibrations.

Figure 8:
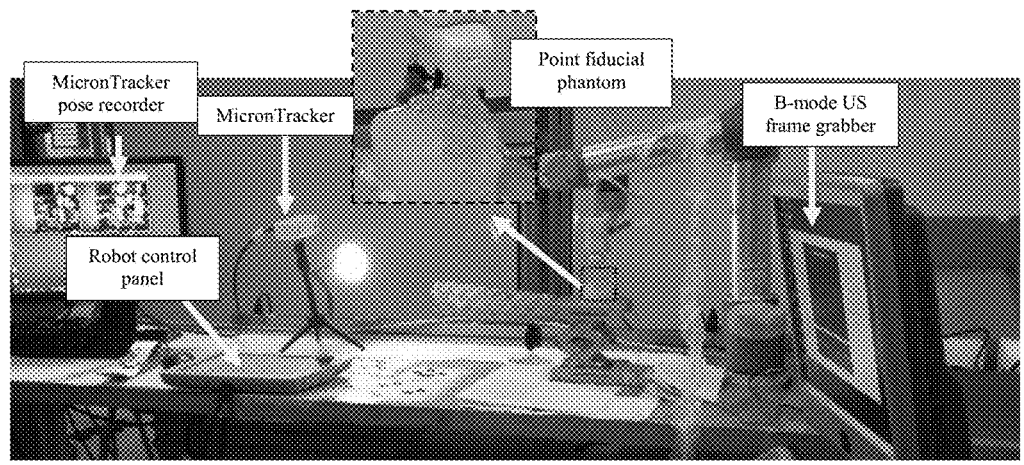
FIG. 8 shows an exemplary freehand ultrasound calibration setup.

FIG. 8 shows the experiment setup for the freehand ultrasound calibration according to some embodiments of the invention. An extra light is placed beside the MicronTracker to increase the accuracy of the tracker readings.

To collect data, the point fiducial is inserted into a gel phantom and fixed on a stage at a height of about eight inches with respect to the table. Ultrasound gel is used to avoid contact with the gel phantom so that the point fiducial does not move due to phantom's deformation. The reason for using gel instead of a water tank is that, due to the tube that comes out of the probe holder, the range of motion may be limited inside a water tank. An extra marker is attached perpendicular to the original marker to cover more ranges of motion. These two single markers are registered in the MicronTracker software as a multi-facet marker. After the calibration is done, the extra marker is detached. The following explains the setup in more details.

The camera is fixed at the side at a distance of about 60 cm from the point fiducial and its software tool can record a stream of rotation matrices and the positions of the probe's marker in the camera coordinates. The ultrasound machine has a frame grabber software tool that records B-mode images. The depth is set to 7 cm. The focus is adjusted at each data collection to get the best image. The frequency is set to 5 MHz and US images are stored at a rate of 17 Hz. The US machine is in B-mode Harmonic Resolution mode and the TCG is set to a low value.

When the best position of the probe is achieved, 20 frames are recorded on both the US machine and MicronTracker pose recorder while the robot is stationary. Later on the average of these 20 frames is taken to analyze each data set. Hence, each data set includes 20 US frames and 20 transformation matrices from camera to the probe's marker. The above is repeated 60 times to get 60 data sets. The average of the 20 points in each data set is taken to produce 1 US image and 1 transformation matrix for each set. The position of the point fiducial is segmented manually in all images and then converted to millimeters. Gradient solver is used to find X1.

Figure 9:
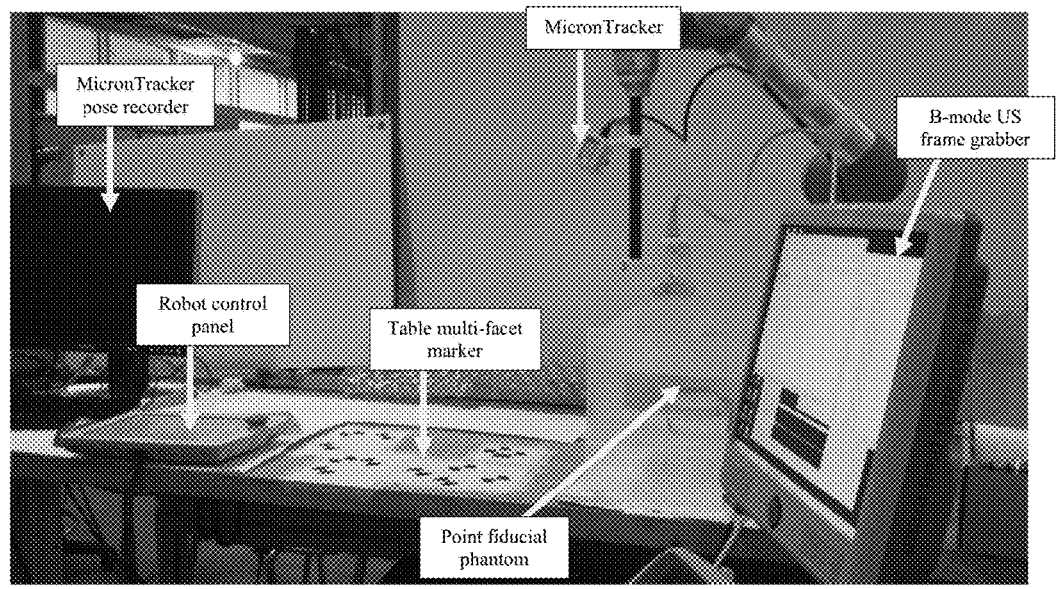
FIG. 9 shows an exemplary robot-held ultrasound calibration setup.

FIG. 9 shows the experiment setup for the Robot-held ultrasound calibration. The data collection procedure for the robot-held ultrasound calibration is similar to the freehand one except for the following. First, the point fiducial is inserted into a gel and fixed inside the water tank. The water tank is used here because it provides more convenience and no extra gel is required. In addition, the end-effector design is such that the range of motion will not be limited by the water tank. Second, a multi-facet marker is attached to the table and this marker is fixed with respect to the robot base. This time the tracker is moving and the marker is fixed. Hence, the transformation matrix is inversed.

The reconstruction precision is used to evaluate the calibrations. For the freehand calibration, three data sets are discarded due to empty readings from MicronTracker and hence 57 data sets are used. 45 sets are used to find X1 and 12 points are used to evaluate the reconstruction precision. For the robot-held ultrasound calibration, four data sets are discarded and hence 56 sets were used in total. 44 data points are used to find X2 and 12 are used to evaluate the reconstruction precision. Table 1 shows the reconstruction precision along axes together with the norm of the precisions.

TABLE 1

Ultrasound calibrations reconstruction precision

| | Precision (STD in mm) | | | |
| --- | --- | --- | --- | --- |
| | Norm | X | Y | Z |
| Freehand | 4.30 | 1.20 | 0.97 | 3.99 |
| Robot-held | 1.79 | 0.69 | 1.25 | 1.05 |

The low accuracy observed for the freehand ultrasound calibration may be due to limited range of motion that is imposed by the rigid body. It can also be because of the auxiliary marker that is registered to the first marker and creates more error in the tracker's readings.

As previously mentioned, in order to evaluate the overall system performance, an extra calibration may be performed. This calibration, referred to herein as hand-eye calibration, is done by fixing a marker on the table and moving the camera, while it is attached to the end-effector, to different viewing angles of the marker, similar to what is done for the robot-held ultrasound calibration. Similar data analysis is done and the norm reconstruction precision for the current calibration is 2.52 mm.

Figures 10A, 10B:
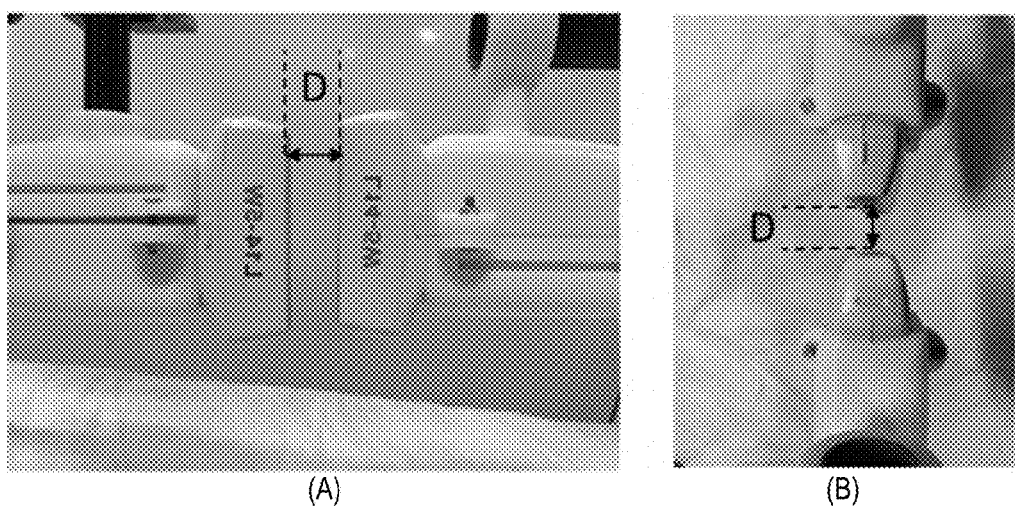
FIG. 10A illustrates dynamic experiment alignment from a first viewing angle (D=20 mm)
FIG. 10B illustrates dynamic experiment alignment from a second viewing angle (D=20 mm)

The overall system performance is evaluated by fixing the freehand probe and running the system so that the robot-held probe becomes aligned with the freehand one. This is done with different initial positions for the robot-held probe and the repeatability is measured. The results are shown in FIG. 10 and Table 2. FIG. 10 shows that the image planes are visually aligned (D=10 mm) and have at least 50% overlap.

TABLE 2

Repeatability of robot-held US image corners for a fixed freehand probe

| | Repeatability (mm) |
| --- | --- |
| corner 1 | 5.87 |
| corner 2 | 5.16 |
| corner 3 | 4.97 |
| corner 4 | 5.73 |

There are other ways of choosing calibrations for the system. For example, an alternative way of finding X2 is to calibrate the ultrasound image to the robot tooltip, i.e., find the transformation from the robot tooltip to the robot-held probe ultrasound image, and then use X3 to recover X2. The advantage of this alternative method is that one can benefit from the higher accuracy of the robot (in comparison with the MicronTracker). However, it is required to calibrate the robot and perform X3 first. Also, one can combine the transformations recovered with the two methods to achieve a better accuracy.

In the above examples, an ultrasound tomography system is described that can be used for soft tissue tomographic imaging, deep ultrasonic scanning, and faster scanning of the anatomy. The use of a robot-held probe in such applications enables the use of two tracking probes with better accuracy and ease of operation. An overview of the system's prototype and components is provided. A point target ultrasound calibration is delivered which shows a reconstruction precision of few millimeters.

The following examples describe some embodiments in more detail. The broad concepts of the current invention are not intended to be limited to the particular examples. Further, concepts from each example are not limited to that example, but may be combined with other embodiments of the system.

EXAMPLES

Example 1: Enabling Technologies for Robot-Assisted Ultrasound Tomography

Ultrasound imaging is a low-cost and non-ionizing radiation imaging modality. Most clinically available US systems are based on single view reflection imaging. However, similar to CT or MRI, which provide tomographic images of the anatomy, there is potential for transmission imaging and enhancement of the amount of information imaged by using an US system. Some example methods include three-dimensional (3-D) US, multi-view imaging, and US tomography.

3-D US has been an interesting area of research for many years. The first 3-D US was introduced by the Kretz Company in 1989 using a mechanically swept probe. This probe consists of a 1-D array of US elements that was mechanically swept by motors and actuators [1]. An alternative to this type of probe, which can enable 3-D imaging with any conventional 2-D US system, was proposed by researchers at the University of Western Ontario. A mechanical add-on enables the sweeping for any type of 2-D probe [2]. The next generation of 3-D US was introduced by constructing 2-D arrays of US elements known as 3-D or matrix array probes [1]. Freehand tracked US has also been proposed. This technique utilizes a tracking system to enable 3-D reconstruction of the 2-D images collected by the freehand probe [3].

SonoCT technology and spatial compounding are two examples of US multi-view imaging. SonoCT uses beam steering to acquire an US image from several viewing angles leading to more tissue information embedded in one 2-D image [4]. Spatial compounding, however, may be achieved through physical rotation of the US transducer around the target and then combining the acquired images into one image [5]. These types of multi-view imaging methods have proven useful in US imaging, but are not considered truly tomographic compared to x-ray CT or MRI [6] and cannot provide measurements of a tissue's acoustic properties such as attenuation and speed of sound.

US tomography is another way of producing 2-D or 3-D US images through tomographic reconstruction[6-19]. Tomographic imaging using US was proposed as early as 1977 [19], but the hardware technology available at that time and computational limitations have been the major reasons why these ideas have not yet been widely adopted [6]. Recent advancements in technology, however, have made successful implementations of such systems possible [6]. The most common US tomography techniques can be categorized into two types: reflection and transmission. Reflection tomography can provide mapping of boundaries inside the object while transmission tomography can enable measurement of additional parameters such as the attenuation coefficient or time of flight [6,18]. Many recent developments have been associated with US tomography for breast cancer diagnosis. For example, the Softvue system [20] (Delphinus Medical Technologies, MI, USA)—composed of a water tank with an appropriately designed hole to fit in the breast area—has enabled such breast tomographic images using a cylindrical arrangement of US transducers. This setup is used mainly for breast US tomography and has proven helpful in breast cancer diagnosis [6-10].

An alternative way of enabling US tomography is by means of two 2-D US probes, activating one or several of the transducers in one probe as the transmitter and the rest as the receiver [14]. Such a system can make US tomographic imaging available for more general applications. On one hand, the advantages of such types of US tomography make it an interesting area of research. On the other hand, the problem of aligning the two probes appropriately remains a major challenge to this goal. A robot-assisted US tomography system (shown in FIG. 11) is described herein which can address the alignment challenge. The advantages of having the robot in the loop include precise alignment and ease of use. This system comprises two probes: one probe is operated by a sonographer as a tracked freehand probe; the other probe is operated by a robotic arm following the motion of the freehand one. The stereo camera of the MicronTracker is rigidly attached to the robotic arm. The tracker can track the freehand probe and at the same time provide a photographic view of the anatomy.

Several research groups have reported robot assistance for US imaging [21-23]; however, to the best of our knowledge, to date no robot-assisted US tomography system has been proposed. To make the precise alignment possible, at least three calibrations may be required: two US calibrations, and one hand-eye calibration. US calibration is the procedure of finding the transformation from the coordinate frame of a rigid body attached to the US probe to the US image coordinate frame. An extensive review on the current state of the art of US calibration techniques is provided in reference [24]. The method of calibration used in this paper is the point calibration solved using gradient solver [25], though other methods may be used. Hand-eye calibration is the procedure of finding the transformation from the robot tooltip coordinate frame (hand) to the camera (eye) rigidly attached to the robotic arm. We provide a summary of the system setup and calibrations followed by an extensive evaluation of calibrations and the alignment.

Figure 11:
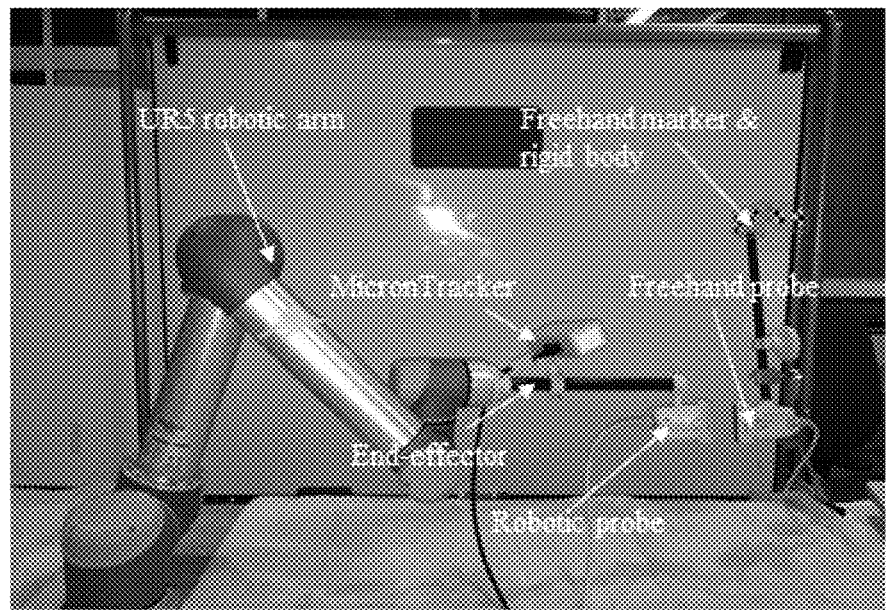
FIG. 11 shows the robot-assisted US tomography system setup according to some embodiments of the invention.

FIG. 11 shows the system setup of the prototyped robot-assisted US tomography. The freehand probe is shown as held by a passive arm. We used a 6 degree of freedom (DOF) UR5 robotic arm (Universal Robots Inc., Odense, Denmark) for which we designed a compatible end effector. For tracking, we used a MicronTracker SX60 (Claron Technology Inc., Toronto, ON, Canada). The MicronTracker uses visible light normal stereo cameras for tracking. It is also lightweight and can be installed on the robotic arm to provide a view of the scanning area. Herein, the word camera may be used interchangeably with tracker to refer to the MicronTracker's stereo cameras.

We design a rigid body that attaches to the robotic arm's end effector and holds both the tracker and the robotic ultrasound probe. In addition, another rigid body is designed for the freehand probe to hold the MicronTracker marker. The appropriate position of the marker on the freehand probe and the place of the MicronTracker on the robotic arm are determined through a configuration study with the assumption that the region to be scanned is a phantom with cylindrical shape and a maximum diameter of 30 cm. The goal is to design the configuration such that for a cylindrical phantom, the tracker and marker keep line of sight and the marker also remains in the tracker's field of measurement. More details of system components, sample configuration study, and mechanical designs are provided in reference [26], which is incorporated by reference herein in its entirety.

Two identical Ultrasonix L14-5W/60 (Analogic Corporation, Richmond, BC, Canada) 60-mm, 128-array, linear transducers are used as the US probes. The SonixTouch US machine is used for both US calibrations.

Figures 12A, 12B:
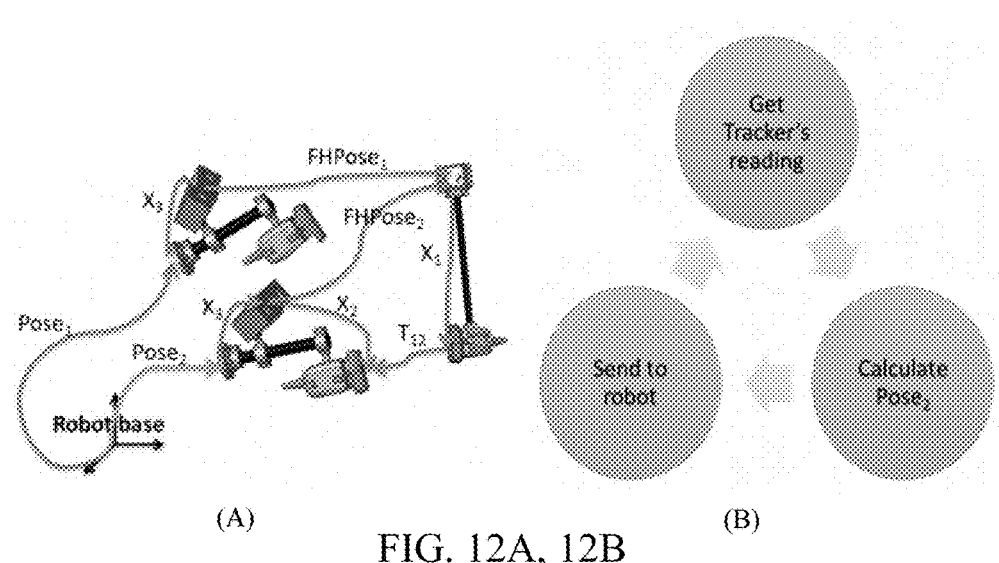
FIG. 12A illustrates transformations used in the software framework.
FIG. 12B is schematic illustration of the software program main modules.

To enable the simultaneous operation of the two probes, a software interface is required. FIG. 12A illustrates transformations used in the software framework. Pose1 is the initial position of the robot tooltip, and Pose2 is the desired position calculated by the software program and sent to the robot. Each curved arrow in FIG. 12A represents a 4×4 transformation matrix. All the transformation matrices can be read through the robot encoders or tracker except for X1, X2, X3, and T12. The calibration procedure to find the three 4×4 transformation matrices (X1, X2, X3) is explained below. The results of the three calibrations (X1, X2, X3) are hard-coded into the software. As shown in FIG. 12A, initially, the two probes are not aligned (Robot tooltip in Pose1).

FIG. 12B illustrates the software program main modules. In stage 1, the software fetches the current MicronTracker's reading and gets the position and orientation of the freehand marker (FHPose$_1$) in the MicronTracker's coordinate frame. In stage 2, using calibrations' information, the software calculates the goal position of the robot tooltip for the appropriate alignment of the two probes. The calculations are done based on the following equations:

$$T_{US1} = Pose_1 \times X_3 \times FHPose_1 \times X_1, \quad (2)$$

$$T_{US2} T_{US1} \times T_{12}, \quad (3)$$

$$Pose_2 = T_{US2} \times X_2^{-1} \times X_3^{-1}, \quad (4)$$

where $T_{12}$ is a 4×4 transformation matrix between the freehand probe US image coordinate and the desired position of the robotic US image coordinate frames. $T_{12}$ is determined by the diameter of the cylindrical phantom (D) and axes definitions, as shown in FIGS. 13A and 13B.

Figures 13A, 13B:
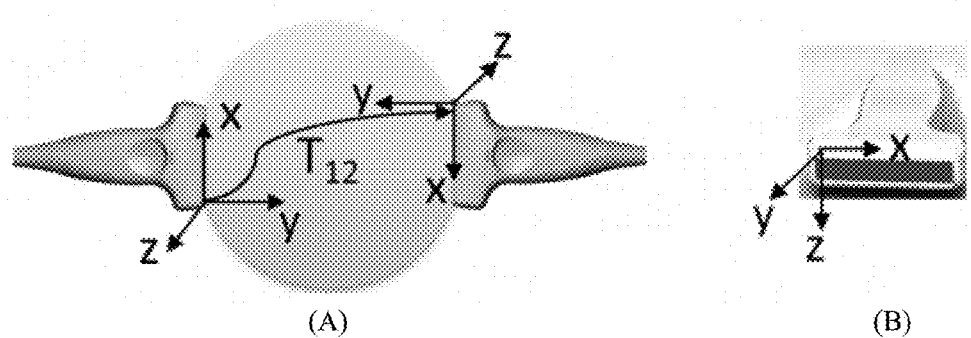
FIG. 13A shows axes direction conventions.
FIG. 13B shows axes definitions from a side view.

FIGS. 13A and 13B show axes direction conventions according to some embodiments of the invention. As illustrated in FIG. 13A, $T_{12}$ is determined based on the definition of the axes in the two probes and also on the cylinder diameter. FIG. 13B shows the axes definition from a side view. The frame's origin for each probe is defined at the probe's edge.

When defining $T_{12}$, it is important to first determine the US images' axes direction and the position of their origin (top corner of the ultrasound image). In the built prototype, the US probes are installed such that their frame and axes direction are as shown in FIGS. 13A and 13B. Hence, the $T_{12}$ transformation comprises a rotation of 180 degrees about the Z axis and a translation along the X axis. The translation along the X axis is equal to the lateral length of the probe, which is 65 mm. In addition, the frames' origins are located at the edges of the US probes, which requires another translation of 9 mm along Z axis (elevational width of the probe tip). Hence, the $T_{12}$ transformation is defined as $$T_{12} = \begin{bmatrix} -1 & 0 & 0 & 65.0 \\ 0 & -1 & 0 & D \\ 0 & 0 & 1 & -9.0 \\ 0 & 0 & 0 & 1 \end{bmatrix}, \quad (5)$$

where the units are in millimeters.

Using Eq. 2, the software finds the position of the freehand US image origin in the robot base's coordinate frame. After that, the desired robotic probe's US image position is calculated using Eq. 3. Then, the goal position of the robot tooltip with respect to the robot base is found such that the robotic probe's US image is aligned with the freehand probe (Eq. 4). In stage 3, a command is sent to the robot controller to move the tooltip to the goal position (Pose$_2$).

The software is written in C++. The MicronTracker is connected to the PC using the IEEE 1394 FireWire port. It has a library called MTC [27] through which the FHPose can be read. The matrix calculations are done using CISST libraries [28]. The PC-robot connection is established through Ethernet.

A program is written to be executed on the robot control panel that is able to establish the client-server connection with the PC C++ program, to send the tooltip current position, to receive the desired position, and to move the robot accordingly. This program operates in a loop to handle the above procedures. The program on the PC sends URScript [29] commands through the Ethernet connection to get Pose$_1$ and send Pose$_2$.

To enable tracking, two US calibrations and one hand-eye calibration are performed. In each calibration, the goal is to identify a 4×4 transformation matrix that determines the relation between two rigidly attached coordinate frames in terms of both translation and rotation in 3-D space. The first US calibration ($X_1$) shown in FIG. 12A, called freehand calibration, finds the transformation from the freehand probe's marker coordinate frame to its US image coordinate. The second calibration ($X_2$), called robot-side US calibration, finds the transformation from the camera's coordinate frame to the robotic probe's US image coordinate. The third calibration ($X_3$), called hand-eye calibration, finds the transformation from the robot tooltip coordinate frame to the camera's coordinate frame.

The method used for the calibrations was point calibration, i.e., a fiducial point was observed by one of the coordinate frames from different viewing angles and positions. The reason for choosing this method was its simplicity, which can be easily adapted to the features of our setup, such as the required line of sight, and the small field of view of the tracker.

Figure 14:
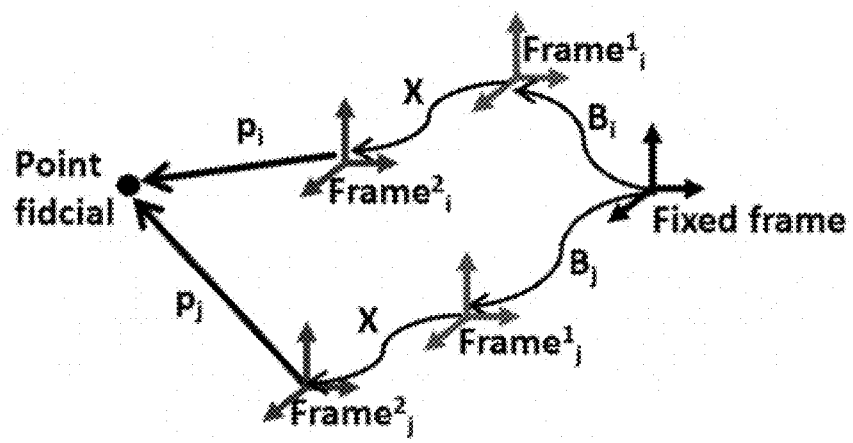
FIG. 14 shows a point calibration diagram.

FIG. 14 shows a point calibration diagram. The calibration's objective is to find X. $B_i$ and $B_j$ are 4×4 transformation matrices that can be read; $p_1$ and $p_2$ are 3-D positions of the fixed point fiducial as observed by Frame 1. As shown in FIG. 14, in point calibration, a fixed point fiducial and a fixed frame are utilized. Frames 1 and 2 are moved to different positions and orientations so that frame 1 can observe the point from different viewing angles. For any position pairs, as shown in FIG. 14, the following equation holds:

$$B_i X p_i = B_j X p_j, \quad (6)$$

Each $B_i X p_i$ defines a point in the fixed frame. Using all the collected data, a cloud of points are formed and the correct X is the one that minimizes the size of this point cloud. To find X, the Gradient Descent algorithm [25] was used. It starts from an initial X and converges to the calculated X iteratively by defining an appropriate cost function penalizing $B_1 X p_1 - B_2 X p_2$.

For US calibrations, if a passive point (such as a cross wire) is used, the accuracy of the calibration may be limited by the image thickness. In fact, while imaging the point, it is not possible to ensure that the point is at the center of the ultrasound beams. To overcome this issue, instead of a simple point, an active echo US element is used as the point fiducial. The active echo element echoes the US beam and shows flashing signs in the US image. This flashing is maximized when the element is at the center of the ultrasound beam, i.e., at the center of image thickness.

Figure 15:
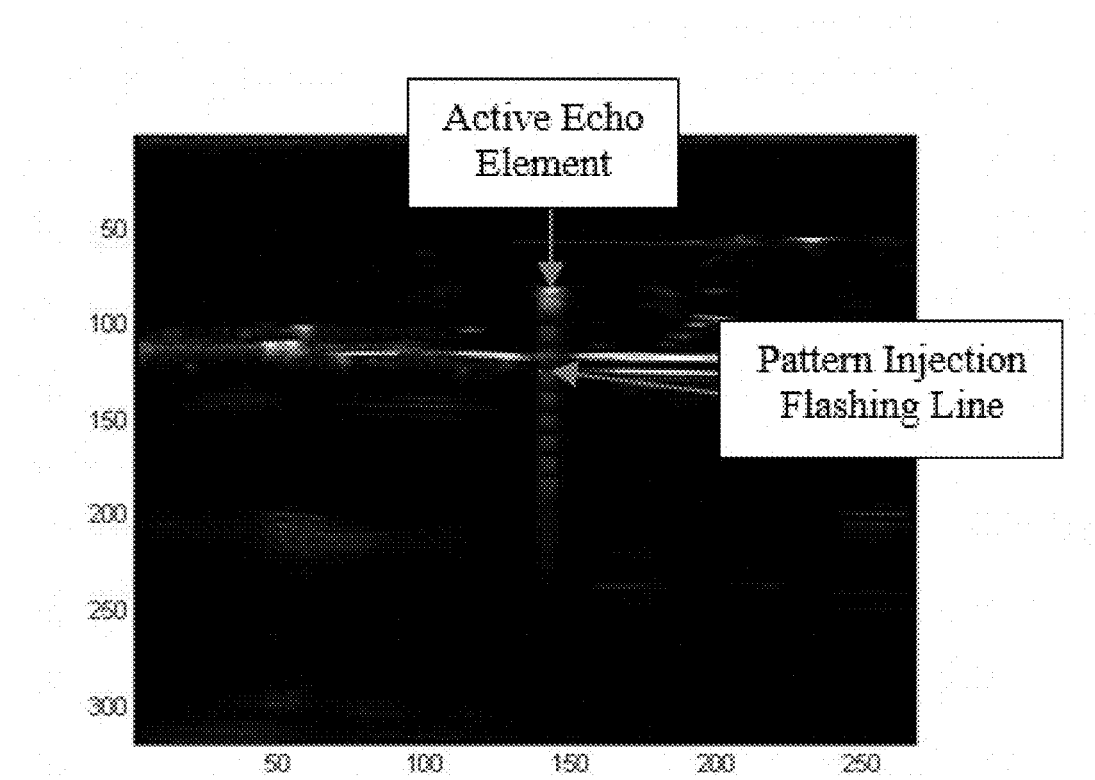
FIG. 15 shows an active echo element and pattern injection in an US image.

A circuit is designed [30] that receives the active echo element signals and amplifies the flashing sign by producing a pattern injection in the US image and also a beeping sound. Once the active echo element is in the center of the US beam, the pattern injection is wider and brighter; the beeping can be heard with a higher frequency. We have also created a sensitivity knob to control the indicator's activation threshold. A sample pattern injection observed in the US image is shown in FIG. 15. Overall, the use of an active echo element can help the operator during data collection to ensure data collection is done when the fiducial is at the center of the image thickness.

Synchronizing the data streams is another challenge during data collection for calibrations. There are methods proposed in the literature for synchronization (or temporal calibration) [31-33], but the data herein are collected when everything is at a static position to avoid the need for synchronization.

In freehand US calibration, the tracker is fixed and the freehand probe is moved to different positions and orientations to image the active echo fiducial. At each probe pose, instead of one reading from the tracker, 20 readings are recorded and their average is interpreted as one pose. This way, first, the reliability of each reading that may have been degraded by environmental noise such as a tiny movement of the camera or marker is increased; second, the standard deviation of these readings can be used as a measure of reading accuracy. For the purpose of data collection for calibrations only, the software demo that comes with MicronTracker's software package is used.

During data collection, at each pose of the probe, the 3-D position of the marker is captured by the fixed camera, and the 2-D position of the fiducial is captured in the freehand probe US image coordinate frame. Since the active echo fiducial is fixed in the coordinate frame of the camera, the manually segmented points in the US images form a cloud of points in the camera coordinates system, and the gradient solver method can be used to find the transformation, X1, that minimizes the size of this cloud of points.

In both US calibrations, similar to the tracker's data collection, at each static pose, 20 US images are collected and their average is used as one US image to segment the active echo fiducial. The ultrasound machine has a software interface that records B-mode images. The image depth is set to 7 cm; the focus is adjusted at each data collection to get the best image. Frequency is set to 5 MHz and the US images are stored at a rate of 17 Hz. The US machine is in B-mode Harmonic Resolution mode and the TCG is set to a low value. The active echo point in the US image is segmented manually.

In robot-side US calibration, the goal is to find X2, the transformation matrix between camera and robotic probe image coordinate frames. In this case, the camera and US image are the moving frames. Hence, a set of markers are fixed on the experiment's table and the end effector (with robotic probe and camera installed) are moved to different positions and orientations with respect to the active echo fiducial. The multi-facet registration is done using Micron-Tracker's software tool to create one unique coordinate frame for all the markers—which has the role of the fixed frame. The markers are distributed on the table carefully such that at least one marker is seen at each camera position. In addition, the markers are chosen to be large with their long vector as large as possible to get the best accuracy. To avoid fast variation of readings from the tracker, its jitter filter is activated; however, it should be noted that due to the use of a multi-facet marker, the accuracy of the tracker's reading is degraded.

At each pose, the 3-D position of the marker with respect to the camera coordinate frame is read by the MicronTracker while the 2-D positions of the fiducial are extracted from US images. The US machine settings are as described for freehand US calibration. More details on the data collection procedures for both US calibrations together with setup pictures are provided in Ref. [26], which is incorporated by reference herein in its entirety.

For the hand-eye calibration setup, similar to robot-side US calibration, a multi-facet marker is fixed on the table, but this time it has the role of a point fiducial. The goal of this calibration is to find $X_3$, the transformation between the camera and the robot tooltip coordinate frames. Hence, the camera and the robot tooltip are the moving frames. The end effector with the camera installed is attached to the robotic arm. The robotic arm is moved to different positions and angles and at each pose the marker can be seen by the camera, as shown in FIG. 16.

Figure 16:
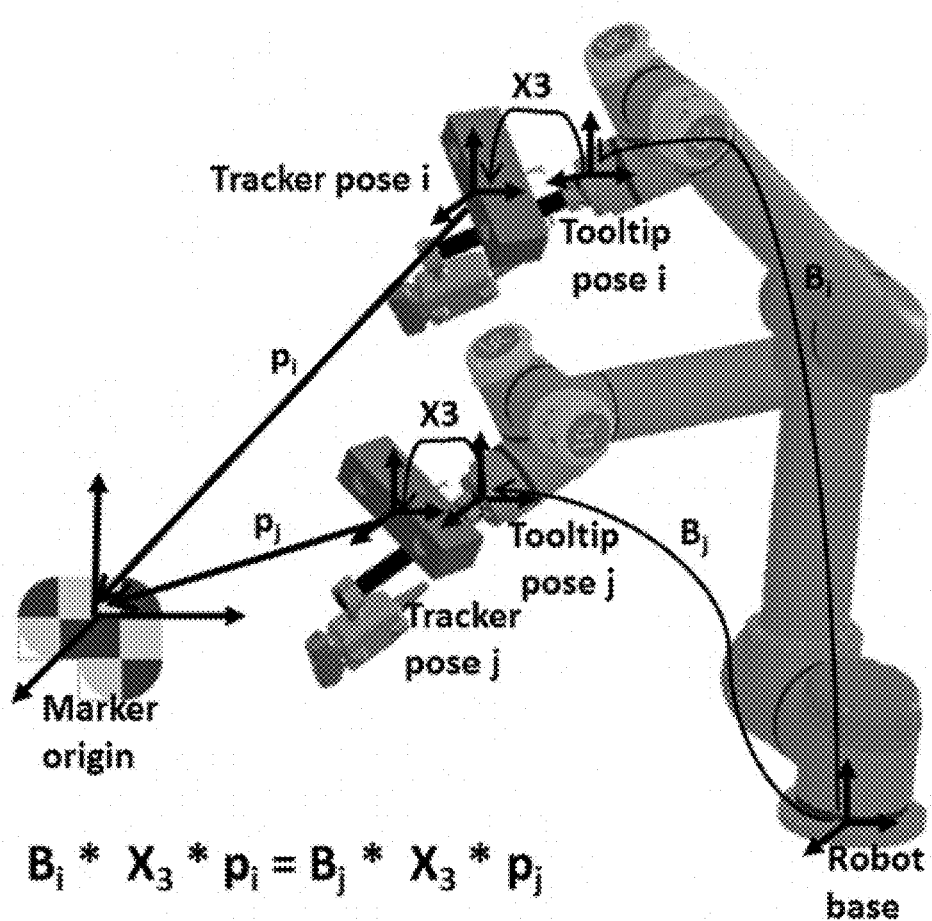
FIG. 16 illustrates an example hand-eye calibration.

FIG. 16 illustrates how the robot tooltip together with the camera is moved so that the camera can see the marker from different positions and orientations. The marker origin is the point fiducial here and the robot base is the fixed frame. At each pose, the hand-eye calibration data set includes the following: (1) a transformation matrix from the robot base to the robot tooltip, and (2) a translation vector from the camera to the marker origin. The robot control panel is used to read the robot tooltip coordinate in the robot base coordinate frames. It should be noted that the default UR5 display uses axis angle representation, which needs to be converted to transformation matrix. The direction of the three angles vector (rotation vector) shown on the display determines the unit vector direction, ê, and its magnitude determines the magnitude of the angle about the unit vector, θ; i.e., e=θê, where e is the rotation vector.

The calculations performed to retrieve the calibration matrices are now explained. From all the collected data sets (each set contains one 4×4 transformation matrix, $B_i$, and one translation vector, $p_i$), some are used to calculate the calibration matrix, and the rest should be put aside for evaluation. In addition, due to the presence of outliers, the transformation matrix found might not be the most accurate matrix possible. Outliers can come from different sources of error such as a decrease in the tracker's accuracy for markers at far distances, pose reading fluctuations due to multi-facet markers, and error in point manual segmentation in the US images. Since the number of data sets collected was chosen to be fairly large, (about 60 for US calibrations and about 40 for hand-eye calibration), it was possible to remove some as outliers. The following evaluation algorithm can be used to enable outlier removal, to ensure that the calibration matrices are calculated as precisely as possible, and to allow for fair reconstruction precision evaluation.

Figure 17:
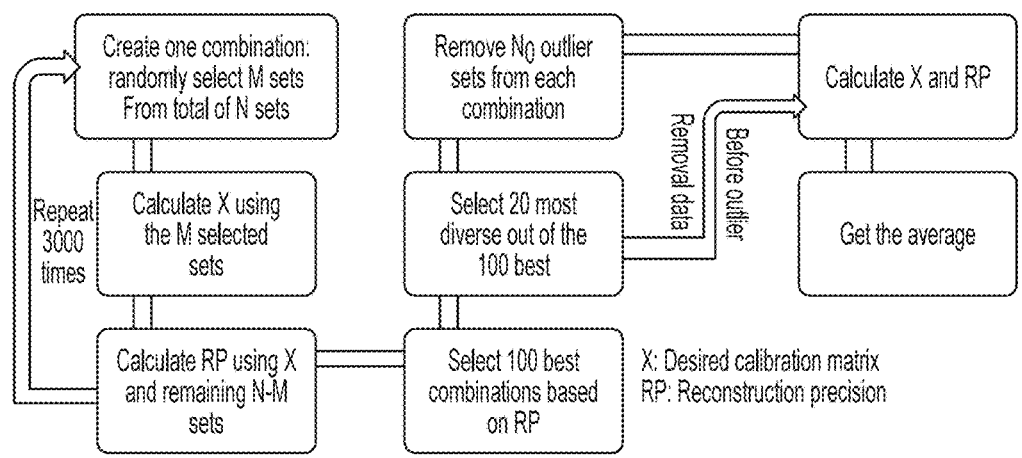
FIG. 17 illustrates a calibration and evaluation algorithm to enable outlier removal and achievement of high precision.

The algorithm is shown as a flowchart in FIG. 17, where N is the total number of sets, M is the number of calibration sets, and NO is the number of sets eliminated as outliers. The first step in this algorithm is to determine which sets should be chosen for calculation of the calibration matrix (called calibration sets) and which sets should be selected for reconstruction precision evaluation (called evaluation sets). It may not be possible to try all the possible cases because the number of possible combinations is large (in the order of 1013 for selecting 45 calibration sets from the total of 60 data sets: C(60,45)=5.32×1013).

To overcome this issue, we randomly select 3000 combinations for which the reconstruction precision is calculated. Next, the 100 best are picked from the 3000 tested cases. To enable fair evaluation in a reasonable time, the 20 most diverse combinations are picked from this refined 100 combinations. Diversity is measured as having the least number of intersecting data sets. At this stage, the candidate outlier data sets are removed from the calibration sets, which are those that have either a tracker reading outlier or a manual segmentation outlier. The tracker reading outlier is determined as those that have the highest standard deviation in their 20 readings for each pose. The candidate manual segmentation outliers are determined beforehand by two independent users flagging those images that are not easy to segment. Finally, the reconstruction precision is measured before and after outlier removal by averaging over the 20 most diverse sets.

Figure 18:
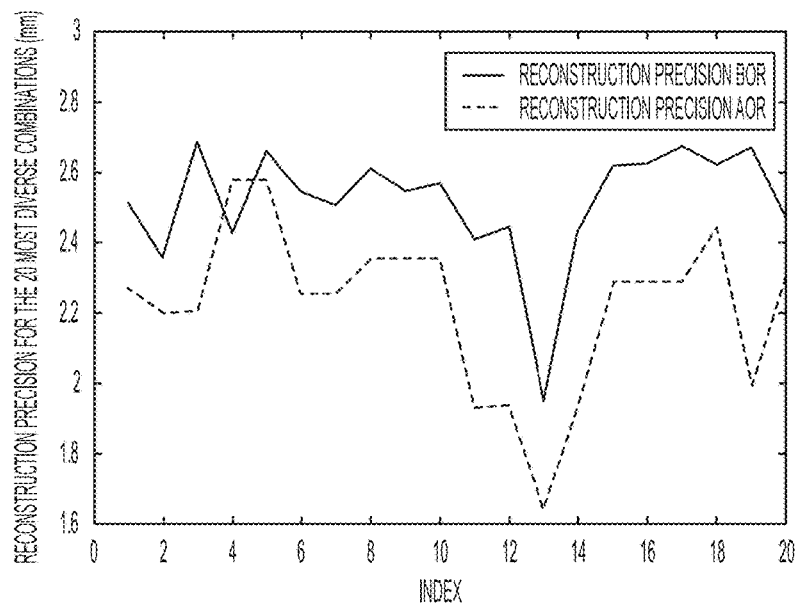
FIG. 18 shows the reconstruction precision of the 20 most diverse sets for hand-eye calibration before (bor) and after outlier removal (aor)

The algorithm described above is used to calculate and evaluate the calibrations. FIG. 18 shows the reconstruction precisions for the 20 most diverse sets for the hand-eye calibration before outlier removal (bor) and after outlier removal (aor). It can be seen that there is a range of reconstruction precisions from 1.6 mm to ~2.7 mm, showing that it may not be reliable to calculate precision based on one selection of calibration and evaluation sets. In addition, outlier removal in most cases improves the reconstruction precision.

The table in FIG. 19 shows the final evaluation output of the algorithm. The X, Y, and Z columns show the reconstruction precisions along X, Y, and Z axes, respectively. The norm columns show the norm reconstruction precision along all three axes. As shown in FIG. 19, freehand US calibration has less reconstruction precision than the robot-side calibration, which is probably because during data collection the US image thickness is parallel to the Z axis of the camera. This means that the accuracy of the collected data is worse. It should be noted that the current configuration enforces such a setup for the calibration of the freehand probe.

The following process is performed to further evaluate the US calibrations. Using the obtained calibration matrix, the positions of the US image four corners in the other coordinate frame involved in the calibration (for the freehand US calibration, the marker coordinate frame, and for the robot-side US calibration, the tracker's coordinate frame) are calculated for each collected pose. Then the standard deviation is taken to measure the repeatability of the reconstructed US images. This procedure is also performed for both calibration matrices found before and after outlier removal.

The four corner points considered in the US image coordinate frame are as follows: A=(0,0,0), B=(0,70,0), C=(60,70,0), D=(60,0,0) in mm. These points are considered because 60-mm probes are used and the depth is set to 70 mm. The table in FIG. 20 shows the results of the US image repeatability evaluation. The standard deviation of the US images' four corners are calculated for the collected poses before outlier removal (bor) and after outlier removal (aor).

In the previous section, the individual calibration evaluations were provided. However, after all the system components have been put together, we are interested in measuring how well the overall system is able to align the two US images. Hence, in addition to the individual evaluations, the overall system is evaluated through a repeatability experiment explained below.

The freehand US probe is fixed using a passive arm. The robot-side US probe was initialized at a position using the robotic arm; through running the software interfaces, the robot was asked to align the robot-side probe with the freehand probe. This procedure was repeated 15 times: once from the same initial position (called stationary repeatability experiment), and then from a slightly different random initial position (called dynamic repeatability experiment).

The data are collected after the robot performed the alignment. Each data set includes the transformation from the robot base to the robot tooltip frames, and the transformation from the tracker to the freehand probe marker frames (Pose$_2$ and FHPose$_2$ as shown in FIG. 12A). The repeatability is measured as the standard deviation of the robot-side US image four corners reconstructed in the robot base coordinate frame as $$P_{Corner} = \text{Pose}_2 \times X_3 \times X_2 \times p_{Corner}, \quad (7)$$

where $P_{Corner}$ and $p_{Corner}$ are the robot-side US image corner positions in the robot base and robot-side US image coordinate frames, respectively. The image corners were defined as explained above. In addition, to allow for possible outliers, two data sets that produce points at far ends of the corner A point clouds, in robot base coordinates system, were removed. The table in FIG. 21 shows the results of the overall system repeatability experiments with a cylinder diameter, D=190 mm. The standard deviations of the robot-side US images' four corners are calculated in the robot base frame.

Figure 22:
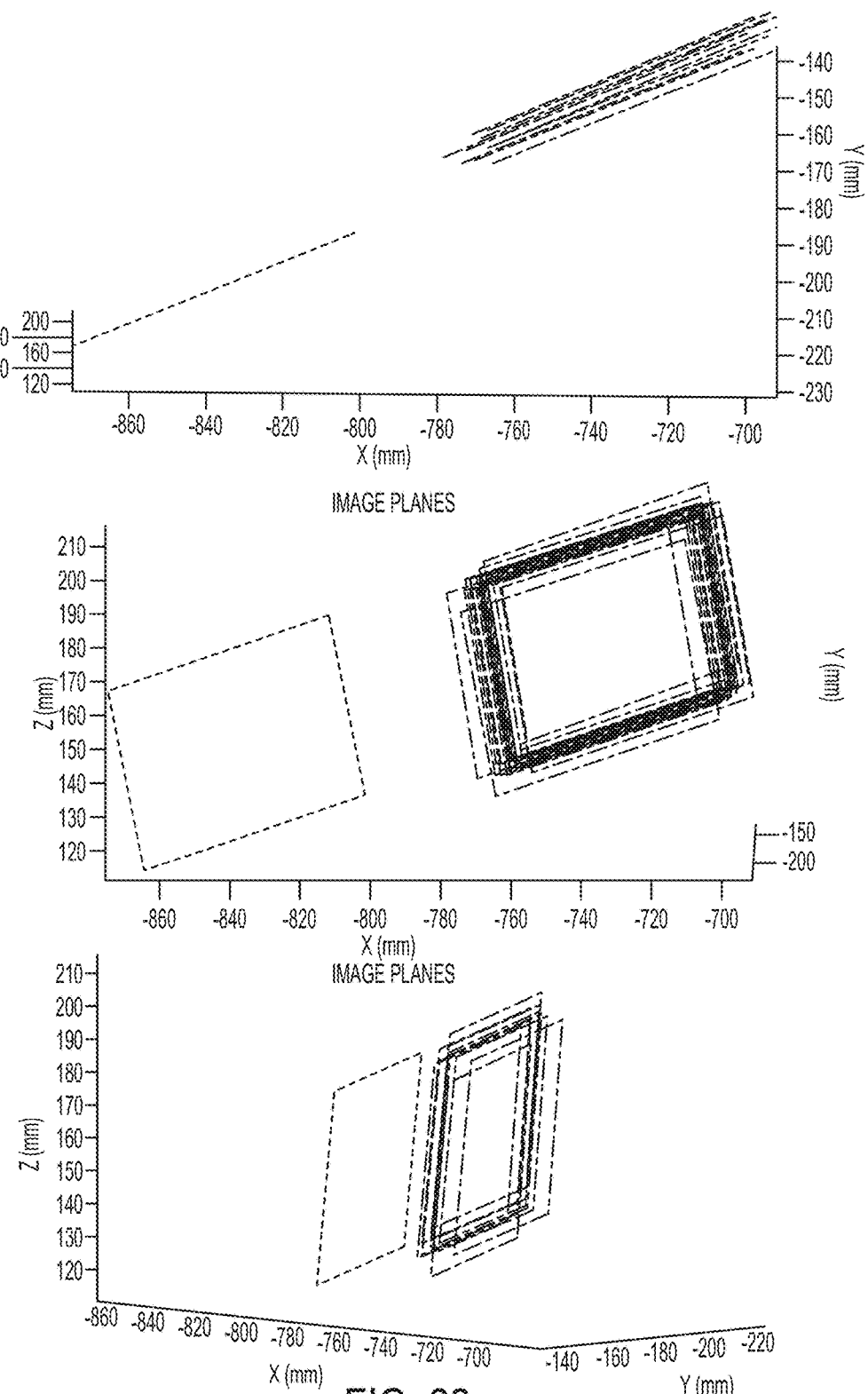
FIG. 22 shows dynamic experiment alignment visualization in Matlab from three different viewing angles (D=190 mm)

FIG. 10 shows a sample alignment of the two probes when the parameter D was set to 20 mm. FIG. 22 shows all of the alignments for the dynamic repeatability experiment visualized in Matlab. The dynamic experiment alignment visualization is shown from three different viewing angles (D=190 mm). The freehand US image is calculated using the first collected data set as $$P'_{Corner} = \text{Pose}_2 \times X_3 \times \text{FHPose}_2 \times X_1 \times p'_{corner}, \quad (8)$$

where $P'_{Corner}$ and $p'_{Corner}$ are the freehand US image corner positions in the robot base and freehand US image coordinate frames, respectively.

As an extension to the proposed robot-assisted US tomography system, force sensors can be added at the robot side to maintain the contact during scan. Other shapes for the scanned region can be adopted by similar configuration studies and benefiting from force sensors. The advantages of using an optical tracker include providing photographic images of the environment and the scanned area as well as avoiding the magnetic interference. However, in areas where the line of sight cannot be maintained using an optical tracker, another robotic arm can be used to operate the freehand US probe in a cooperative mode with the sonographer.

The provided prototype offers a new system setup for testing various US tomography algorithms, enabling deep/fast US scanning, or reconstructing 3-D US images.

Example 2: Robot-Assisted Mirror Ultrasound Scanning for Deep Venous Thrombosis Using Depth Image Deep venous thrombosis (DVT) is an important component of venous thromboembolism (VTE) and a major cause of morbidity and mortality [1]. DVT refers to a blood clot that develops inside a large vein usually deep within the lower leg or thigh [2]. The danger is that part of the clot can break off and travel through the bloodstream, where it can lodge in the lungs causing a blockage in blood flow, organ damage, and death. If part of the clot breaks loose and travels through the bloodstream, the results can be life-threatening. A clot that blocks the blood supply to the lungs is called a pulmonary embolism [3]. Pulmonary embolism is the leading cause of preventable deaths in hospitalized patients, causing, if untreated, death in as many as 16% of hospitalized patients [4].

Preventing a DVT is vital. Unfortunately, DVT often goes unnoticed. About half of people with DVT have no warning signs. The most common tests used to diagnose DVT are US, D-dimer tests, venography. US test is the most common test for diagnosing deep vein blood clots.

US has been used in the medical field since the late 1950s and has become one of the most widely used techniques in modern medicine, with diagnostic and interventional applications across disciplines. The technique of B-mode ultrasonography for the diagnosis of DVT was first described by technologist Steve Talbot in 1982 [5] and has subsequently been refined to become the diagnostic standard [6]. Color-flow Doppler is helpful to assess for residual flow within a DVT and for confirming patency of venous segments. US scans create real-time images of internal body organs and tissues by sending out high-frequency sound waves and recording the reflected waves.

However, the time taken to complete a scanning session and its results depends on the sonographer's skill and experience. In order to obtain the technical and clinical advantages offered by sonography, highly-qualified personnel trained to properly operate transducers and accurately interpret the resulting images are required. In particular, operators must display highly sensitive skills in order to maximize the US data signal-to-noise ratio, which is affected by the reflection and transmission characteristics of sound waves in human tissue. US procedures are also physically challenging for the medical personnel, as they need to hold transducers in some special positions for prolonged periods of time, resulting in high incidences of musculoskeletal injuries and disorders (e.g. carpal tunnel syndrome) [7]. With patients, image acquisition is made more difficult by the fact that sound attenuation increases exponentially with fat thickness, reducing the quality of the image. To compensate for the signal loss, sonographers need to apply even higher forces on the transducer, consequently increasing their risk of muscle injury.

Thus, there is a need for a robot system for US scanning to compensate for the human factor and make the diagnosis easier and more efficient. The idea of using robotics technology to address the challenges and limitations of manual examination goes back to the early 1990s with the first use of industrial robots configured as medical tool holders [8]. The Hyppocrate platform [9] was based on a Mitsubishi robot (PA-10) on which a transducer was mounted as the end-effector. Due to their limited force sensing capabilities, early systems often failed to offer sufficient compliance, dexterity and control performance. New robot designs were developed to better meet the force requirements and provide back-drivable capabilities often absent on highly geared industrial robots. Various designs and clinical applications of similar concepts are discussed in TER [10], Otello/Teresa [11], and UMI [12]. In References [13] and [15], UBC presents a parallel kinematic design which aims at reducing the weight and bulkiness found in earlier systems, while still conserving a relatively large workspace.

The idea of using robots for DVT scanning has not yet been mentioned. For this purpose, we have designed a robotic US scanning system that actively performs auto US scanning by mirroring the sonographer's procedures. The novel "MIRROR" concept can help sonographers simultaneously scan both legs of patient within one scanning time to evaluate a risk of DVT. The is an example of a "mirror mode."

The robot-assisted mirror mode can improve both the efficiency and accuracy of US scanning to detect DVT. For a sonographer, continual scanning of two whole legs via manual control of the US probe would be a tedious task imposing a large burden and demand of more focus. This robot-assisted mirror method can reduce the over-load burden, and at the same time, increase the detecting precision and quality by comparing two sides of US images. By relieving this burden through robot assistance, the sonographer is able to focus on more important tasks. For the patient, keeping a posture for a long time is difficult. The mirror method can reduce the scanning time. It can also provide a reference of both side scanning images for the sonographer. The sonographer can check the scanning results and modify the procedure in real time.

Figure 23A:
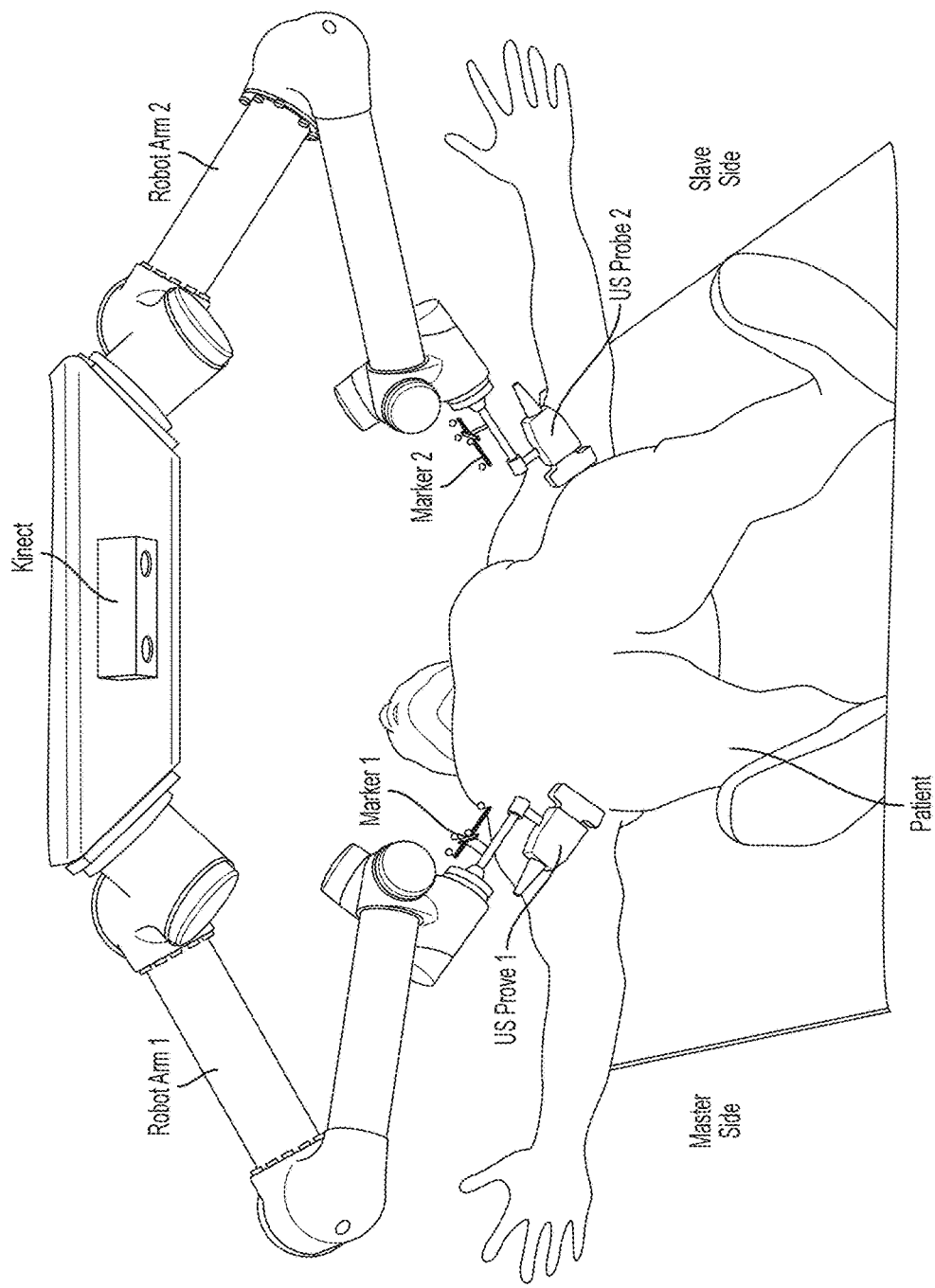
FIG. 23A shows some of the components of the robot assisted mirror US scanning system according to some embodiments of the invention.
Figure 23B:
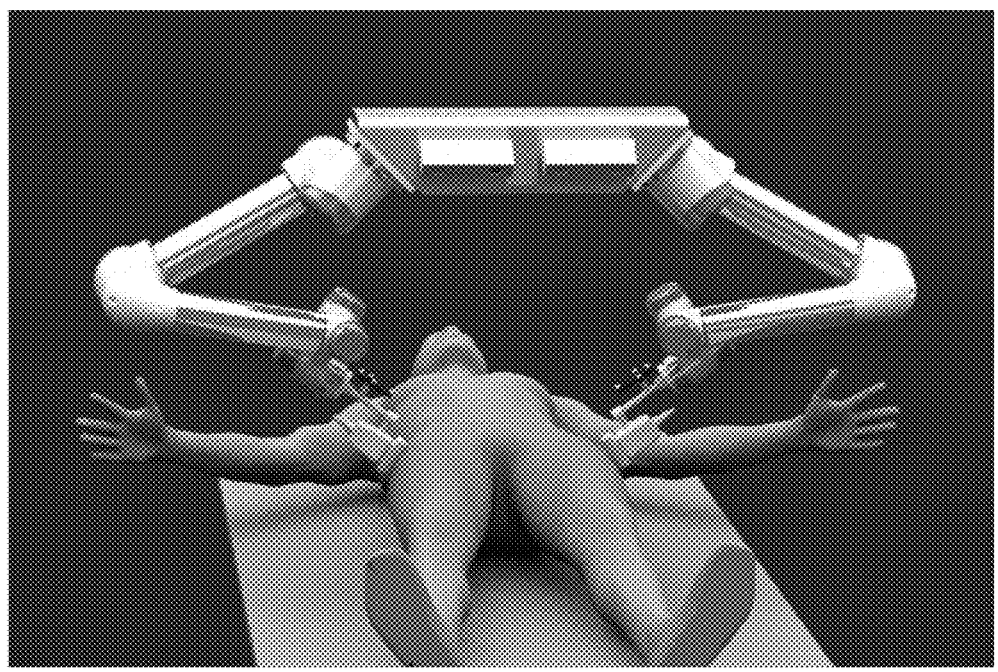
FIG. 23B shows some of the components of the robot assisted mirror US scanning system according to additional embodiments of the invention.
Figure 23C:
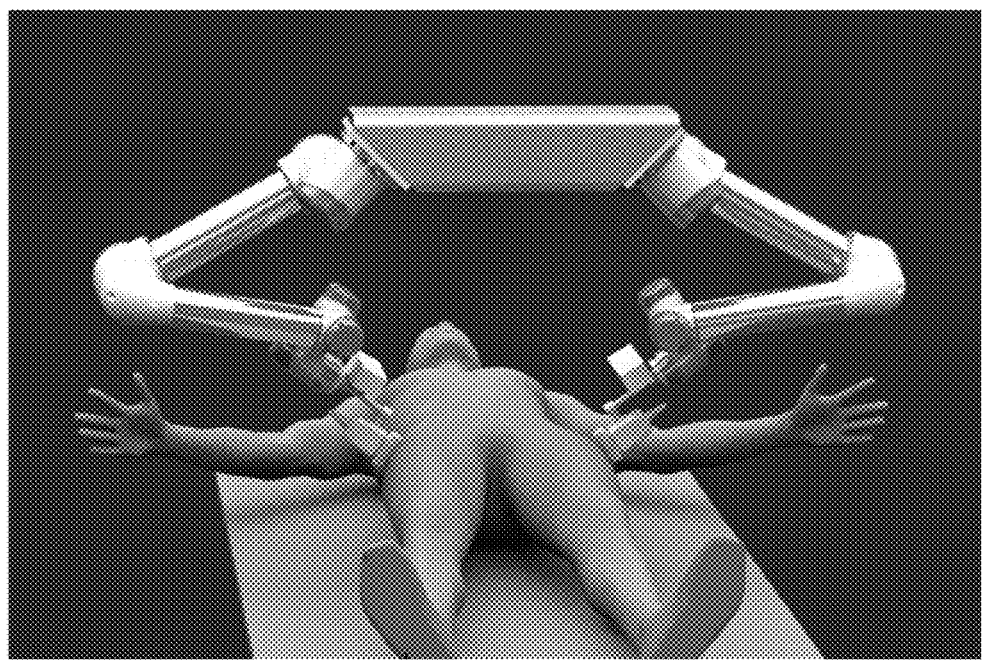
FIG. 23C shows some of the components of the robot assisted mirror US scanning system according to some embodiments of the invention, wherein a vision system is attached to the robot arms.
Figure 24:
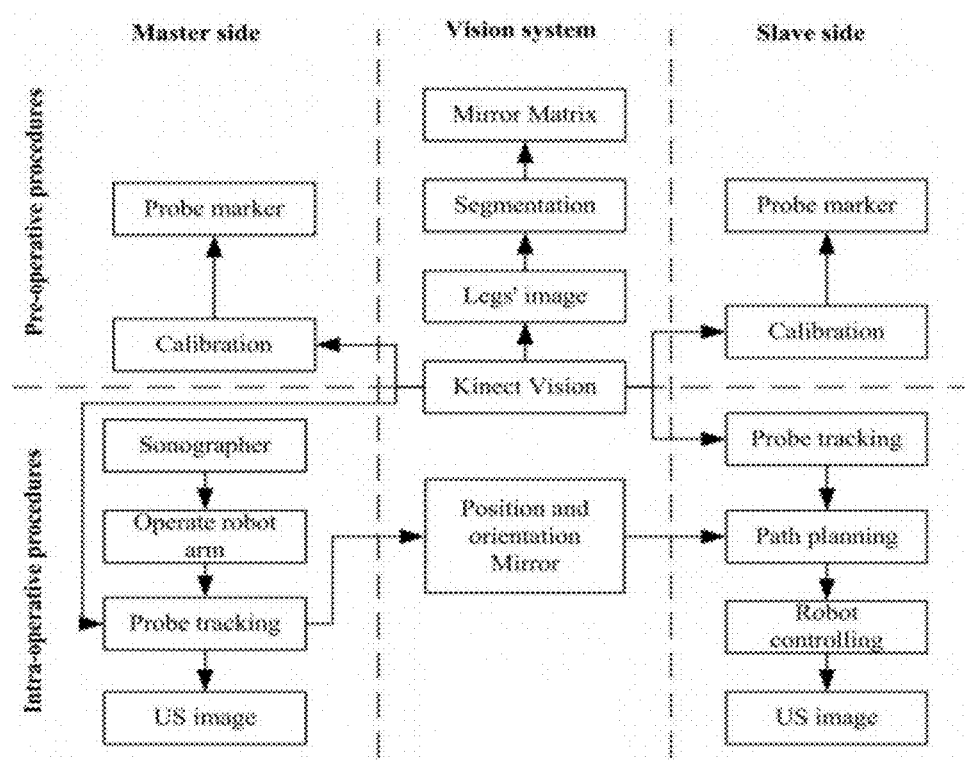
FIG. 24 shows the workflow of the robot-assisted mirror US scanning system according to some embodiments of the invention.

The system according to some embodiments of the invention is composed of three main elements, as shown in FIGS. 23A and 23B: a two-arm robot, a vision system and an US probes. A two-arm robot assists the sonographers scanning legs using US probes. One robot arm with a probe and force sensor is held by a sonographer or a technician, named the master probe. The other robot arm holds another probe named the slave probe. On the master side, the sonographer holds the robot arm and operates the probe to inspect one leg. On the slave side, the robot follows the master probe on navigation and scans the other leg. The appropriate movement of the master probe can be calculated by a vision system and sent to the slave probe as the robot mimics the motion of the sonographer. A vision system can obtain depth images and RGB images in real time. Due to the quality of the depth sensing, and given the low-cost and real-time nature, the Kinect [14] has become popular with researchers and enthusiasts [15,16,17,18,19]. In FIGS. 23A and 23B, one or two Kinect sensors are used to recognize both the patient's leg and the probes. In order to calibrate the Kinect(s) and the probes, an optical marker is fixed on each probe. This optical marker can be seen in a depth image due to the IR sensor on the Kinect [20]. It's a more direct and easier way to calibrate the probe and the Kinect than using an optical tracker. The probes can be mounted on the robot. The nominal position and orientation of the probe with respect to the robot end-effector can be adjusted through a series of set screws. As shown in FIG. 23C, the vision system can instead be attached to the robot arms. For example, a Kinect sensor may be attached to each robot arm near the robot end-effector. A Kinect-like device can also be used to digitize the surface of the patient and the corresponding probes.

The procedure for robot-assisted scanning can be divided into two processes, preoperative and intra-operative. FIG. 23 presents the workflow for the procedure. In the preoperative procedures, the Kinect vision obtains the depth image of the two legs and the master probe. After segmenting the two legs from the background, the mirror algorithm maps the scanning leg to the other side. Then an iterative closest point (ICP) algorithm is applied to register the mapped leg to the other leg. They are overlaid together. The mirror matrix between the two legs is obtained. So, the master probe with the optical markers can be "mirrored" to the opposite side according to this mirror matrix. The calibration matrix between the Kinect and the master probe is also gained after calibrating the optical marker between its own system and the Kinect system.

In the intra-operative procedures, the sonographer operates the robot arm with the probe to scan one leg and get the US images. The movement and the scanning point's position and orientation are mirrored based on a mirror and calibration matrix. By combining path planning and the mirrored motion, the slave probe scans the other leg after robot controlling and gets another volume of US images. The sonographer can determine the scan positions in real time and judge the potential risk of DVT by comparing both sides' US images.

Devising a mirror method is one of the major challenges in guiding the slave probe to track the sonographer's scanning movement. The accuracy and precision of the register algorithm can influence the mirror results greatly. Iterative closest point (ICP) is an algorithm that is extensively used to register two point sets in the computer vision and robotic communities for registration and tracking purpose [21]. Due to its simplicity and efficiency, the standard ICP is employed herein to do registration since the standard ICP can converge to the local minimized once we provide a good initial solution.

FIGS. 25A-25D shows steps of the left-right leg mirror method. Before mirroring, the two legs are segmented from the background. A Sobel method is used here as the segmentation algorithm. The legs can be abstracted based on different heights in the scene based on segmentation results.

Figures 25A, 25B, 25C, 25D:
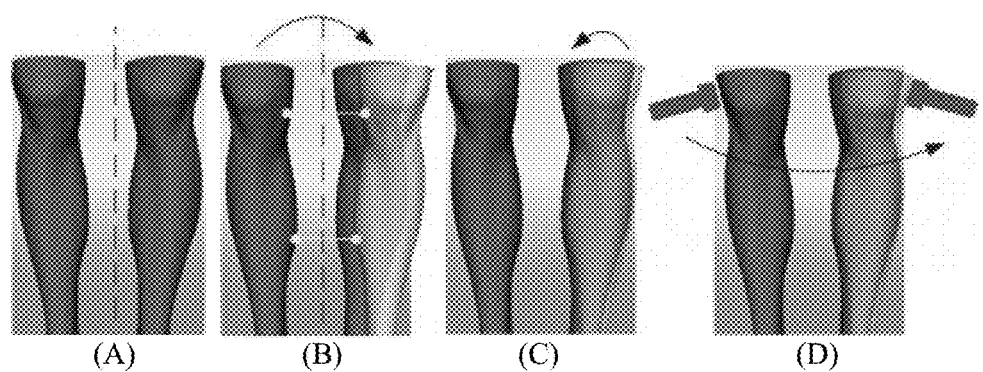
FIG. 25A illustrates the first step of the left-right leg mirror algorithm: segment and separate two legs.
FIG. 25B illustrates the second step of the left-right leg mirror algorithm: pre-mirror the right leg to the left area.
FIG. 25C illustrates the third step of the left-right leg mirror algorithm: register the left leg and the mirrored right leg.
FIG. 25D illustrates the fourth step of the left-right leg mirror algorithm: mirror master-probe.

$r_i \in R1$ are points on the right leg, and $l_i \in L1$ are points on the left leg. First, a virtual mirror plane C1 is set to separate the left leg and right leg, as shown in FIG. 25A. Second, we randomly chose four points $r_a$, $r_b$, $r_c$, $r_d$ on R1 and calculate the projection distance between the four points and C1. Suppose the projective points are $c_a$, $c_b$, $c_c$, $c_d$. Next, we calculate Euclidean distance between $r_a$, $r_b$, $r_c$, $r_d$ and $c_a$, $c_b$, $c_c$, $c_d$, $$D_i = |c_i - r_i| \tag{9}$$

We denote the mirrored right leg as R1', and the mirror position of points $r_i' \in R1'$. Mirrored points $r_{a'}$, $r_{b'}$, $r_{c'}$, $r_{d'}$, on R1' can be calculated according to the distance $$D_i' = D_i = |r_i' - c_i| \tag{10}$$

The right leg is then pre-mirrored to the left area, as shown in FIG. 25B. The mapping matrix T1 is computed by $r_i$ and $r_i'$.

$$R1' = T1[R1] \tag{11}$$

After mirroring the right leg to the left, the third step is registration. The mirrored right leg and the left leg need be registered together. Standard ICP achieves the operation and calculates the transfer matrix T2 between L1 and R1', as shown in FIG. 25C.

$$T2 = \begin{bmatrix} R_{LR'} & T_{LR'} \\ 0 & 1 \end{bmatrix} = ICP[L1, R1'] \tag{12}$$

Here, $R_{LR'}$ denotes to the rotation between R1' and L1, and $T_{LR'}$ denotes the translation. The mirror transformation matrix between two legs $T_{mir}$ can now be calculated:

$$T_{mir} = T2T1 \tag{13}$$

All the leg's points can be mirrored to the corresponding positions according to $T_{mir}$, as can the master probe. In FIG. 25D, the master probe is mirrored to the other side using $T_{mir}$. When the sonographer scans one leg, this mirror method calculates the real-time position and orientation of the master probe, and provides the mirrored position and orientation to the robot.

The mirror position can be transformed from the Kinect coordinate system to the probe coordinate system, and the robot can move the slave probe to the proper position. An optical marker is mounted on the probe because it can be easily recognized and segmented in depth images. The relative distance from the marker to the edges of the probe is constant. If the center of gravity of the marker can be segmented and calculated from the depth image, then we can determine the position of the probe.

Figures 26A, 26B:
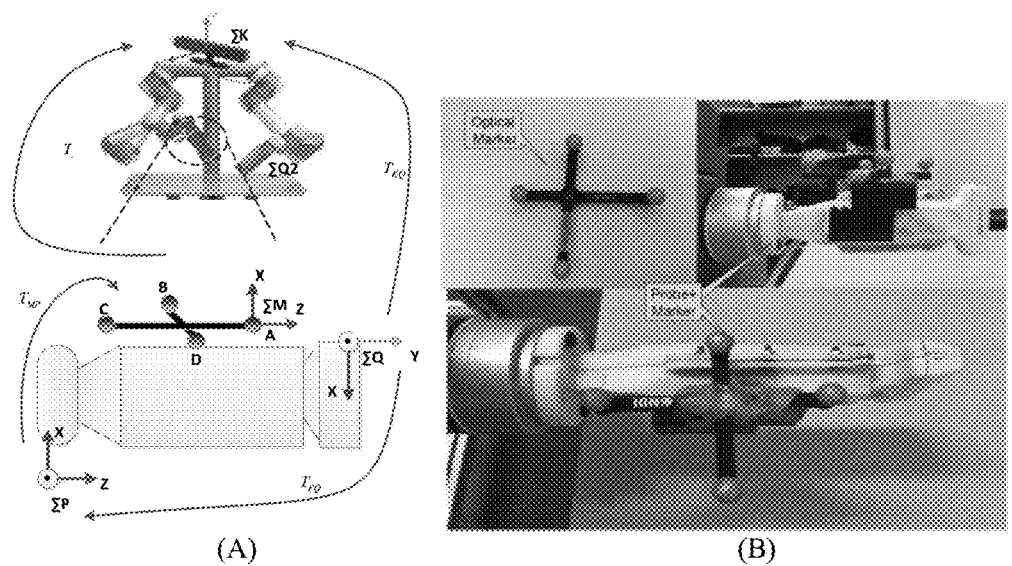
FIG. 26A illustrates the calibration between the Kinect and the probe.
FIG. 26B shows the fixed optical marker position on the probe, which is constant.

FIG. 26A shows the coordinate system of the probe's top $\Sigma P$, the probe's end-effector $\Sigma Q$, the marker $\Sigma M$, and the Kinect $\Sigma K$. The transformation between $\Sigma P$ and $\Sigma M$ is denoted $T_{PM}$, the transformation between $\Sigma P$ and $\Sigma Q$ is denoted $T_{PQ}$, the transformation between $\Sigma M$ and $\Sigma K$ is denoted $T_{MK}$, and the transformation between $\Sigma K$ and $\Sigma Q$ is denoted $T_{KQ}$.

Assuming $T_{PQ}$ and $T_{PM}$ are known beforehand, the marker and the Kinect first need to be calibrated. According to image segmentation results, the four balls of the marker A, B, C, D are segmented from depth image, after center of gravity calculating, and the positions $P_A$, $P_B$, $P_C$, $P_D$ can be obtained in Kinect coordinate system. The positions of the four balls $P'_A$, $P'_B$, $P'_C$, $P'_D$ in the coordinate system $\Sigma M$ are known according to the marker's datasheet [20], so the transformation matrix between the maker and the Kinect can be calculated:

$$\sum K = T_{KM} \sum M = \begin{bmatrix} R_{KM} & T_{KM} \\ 0 & 1 \end{bmatrix} \sum M \quad (14)$$

FIG. 26B shows how an optical marker is fixed on the probe, such that the marker's position on the probe is constant. Then the transformation between Kinect and the probe's end-effector can be calibrated by $$T_{KQ} = T_{KM} T_{MQ} = T_{KM} T_{MP} T_{PQ} \quad (15)$$

To mirror the master-probe to the slave side, first the probe position needs to transform to the mapping position based on the matrix $T_{mir}$ calculated by the mirror method in the Kinect coordinate system. Second, the mirrored position needs to transform to the probe coordinate system based on $T_{KQ}$.

Figure 27:
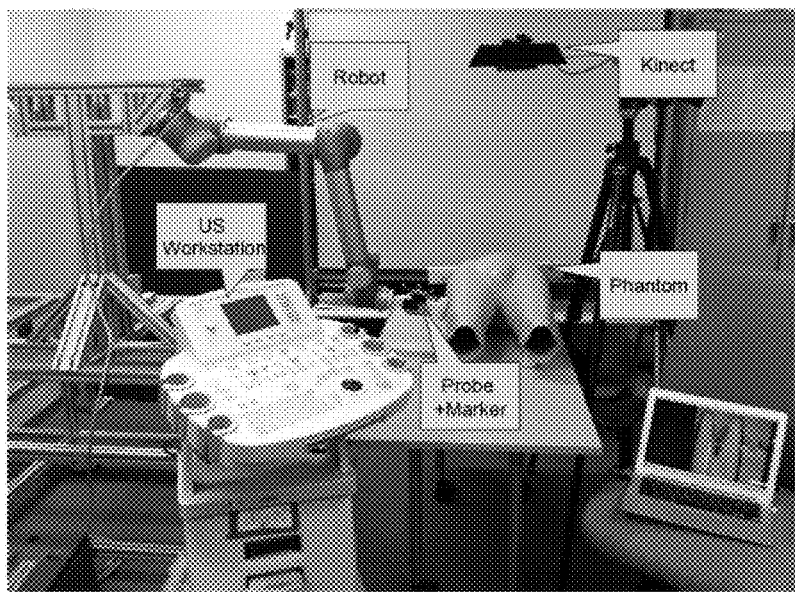
FIG. 27 shows the experimental setup of the robot-assisted mirror US scanning system according to some embodiments of the invention.

We demonstrate the mirror method on both a phantom and a human leg. FIG. 27 shows the system setup according to some embodiments of the invention. The master side is built up in these experiments to assess the performance of the mirror mode. We use a UR5 robotic arm (Universal Robots, Inc., Odense, Denmark) which is a lightweight and noiseless robot with six degrees of freedom. All of the six joints have a range of rotation of 360 degrees. We use Ultrasonix machines (Ultrasonix Inc., Richmond, British Columbia, Canada) as an US workstation. The probe is an identical 60 mm linear array one.

Figures 28A, 28B, 28C, 28D:
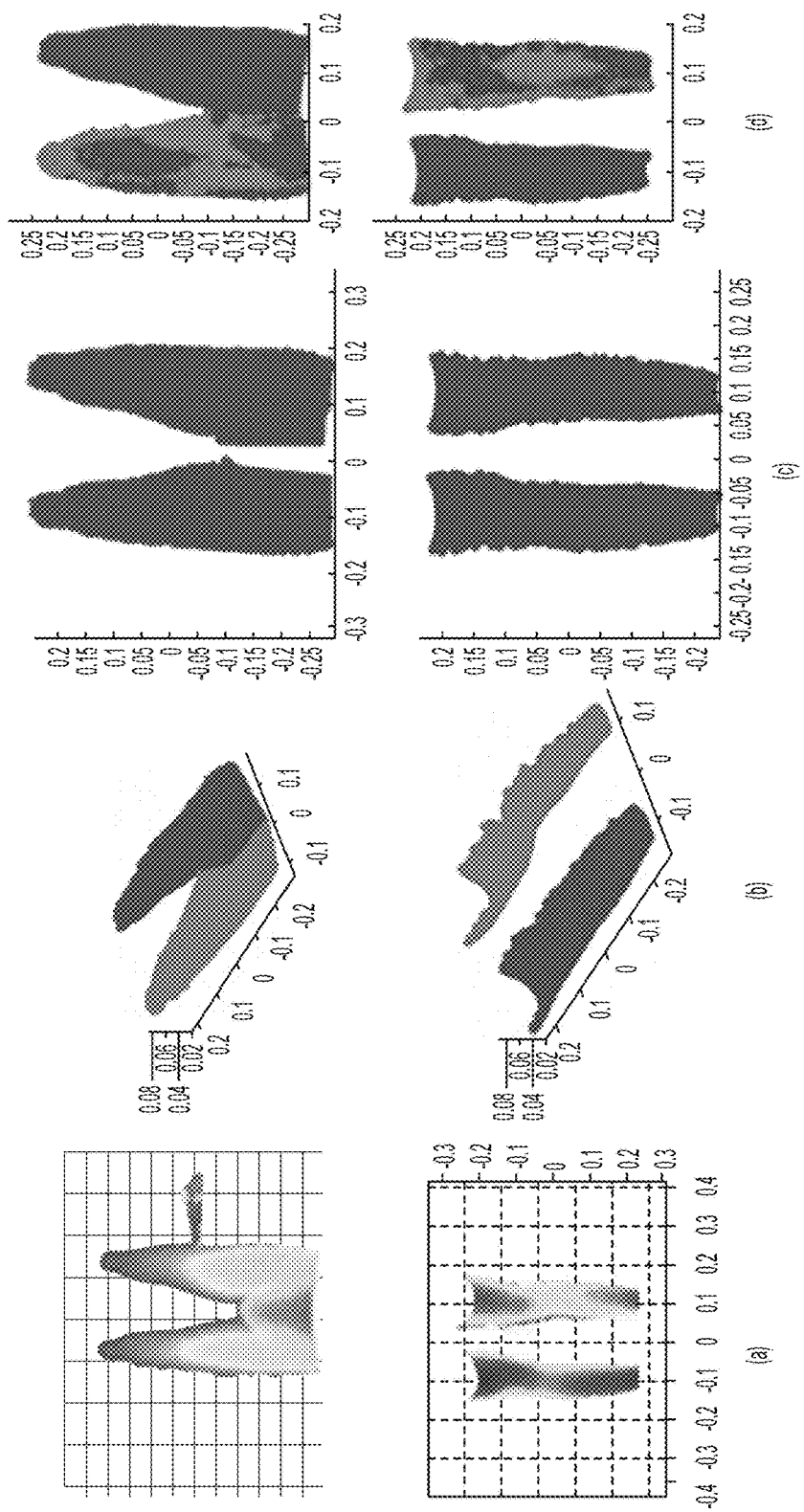
FIG. 28A shows mirror results for the segmented legs from the background (top row shows the mirror result of phantom, bottom row shows the result of human legs)
FIG. 28B shows the shows mirror results for the separated legs.
FIG. 28C shows the shows the mirrored right leg.
FIG. 28D shows how the mirrored right leg is registered to left leg using ICP iteration.

FIGS. 28A-28D show the results of the mirror method for a phantom (top row) and for human legs (bottom row). FIG. 28A shows the legs segmented from the background. We set the failed measured points as the 0 value, which usually happens in the irregular edge of objects or surfaces that do not reflect IR rays well. FIG. 28B shows the separated legs. The right leg is mapped to the left area as shown in FIG. 28C together with the right leg. Finally, after ICP iterations, the mirrored right leg and the left leg are registered together as shown in FIG. 28D.

Figure 29:
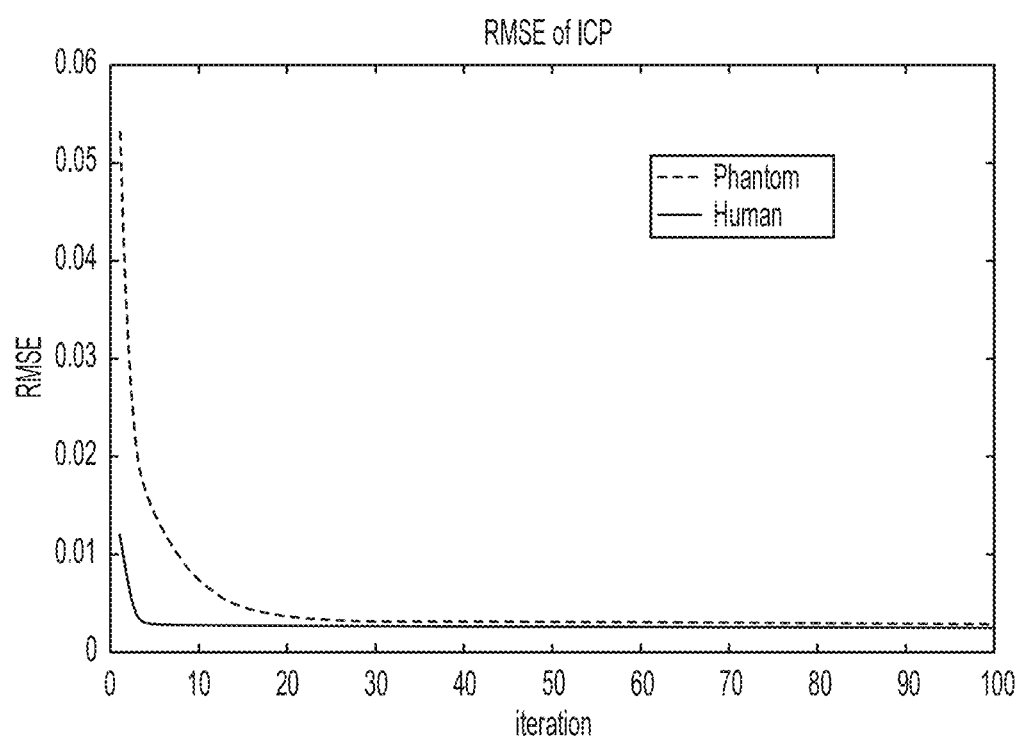
FIG. 29 plots a comparison of the root-mean-square error (RMSE) of the iterative closest point (ICP) in both phantom experiments and human leg experiments.

FIG. 29 shows a plot of the computed root-mean-square error (RMSE) of the ICP in both the phantom and the human leg experiments. The curves indicate that increasing the iteration times can reduce the RMSE of the ICP, but after a certain number of iteration, the RMSE of the ICP is unchanged.

The quantitative results of the method are demonstrated by calculating the correlation coefficients of the mirrored right leg and the left leg. The results are shown in the table in FIG. 30. The correlation coefficient shows the similarity between the mirrored right leg and the left leg after ICP. The fact that the correlation is higher for the phantom than the human leg is reasonable as there is some difference between the two human legs based on intrinsic morphology. The mean of the RMSE reflects the accuracy of the ICP. The mean time of the iteration reflect the efficiency of the ICP.

Figures 30, 31:
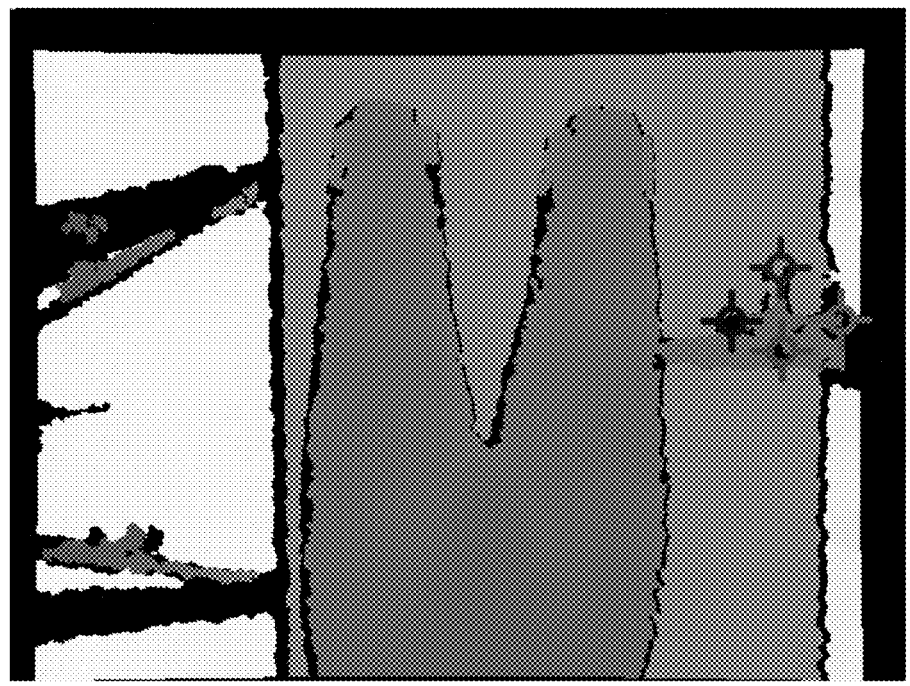
FIG. 30 shows quantitative results showing the correlation coefficient and the mean of the RMSE of the ICP.
FIG. 31 displays segmentation results of markers.

FIG. 30 shows the segmentation results of the four balls of the marker. In this image, the centers of the four balls are calculated as (515,222,0.6950), (550,246,0.6890), (587,223, 0.6440), (550,188,0.6900). Then the position of the slave probe's end-effector is determined according to $$T_{KQ} = \begin{bmatrix} R_{KQ} & T_{KQ} \\ 0 & 1 \end{bmatrix} = \begin{bmatrix} 0.6552 & 0.0839 & 0.7507 & -0.2677 \\ -0.0647 & 0.9964 & -0.0549 & 0.0120 \\ -0.7526 & -0.0126 & 0.6583 & 0.1367 \\ 0 & 0 & 0 & 1 \end{bmatrix}. \quad (16)$$

The preliminary results for the MIRROR robot US scan system indicate that the novel idea is feasible. We a standard workflow for the sonographer to follow. It will greatly improve the current diagnose efficiency and relieve the sonographer from the heavy workload. Moreover, the patient will feel more comfortable during the operation. Besides, this system has another advantage that it provides two comparable US images for both of the legs. This may have important clinical value in the future.

The results shown in FIGS. 28A-28D indicate that there are errors for the mirroring of two legs. The correlation coefficient for leg phantom (0.9493) is much higher than that of the human legs (0.8809). There are several reasons which contribute to this difference. One major reason lies in the intrinsic morphology difference between two legs of a human. This difference was just observed from one volunteer. Genetic factors or behavioral habits may also enhance the difference. The registration process may also cause error for two legs' mirroring. The individual difference cannot be neglected, but as a large-scale screening measure, this system has great significance for clinical applications.

Force feedback can be added on both sides of the robot. For the master side the force sensor may be necessary for the human-robot cooperation. For the slave side, since there are always differences between two legs and registration error, the mirrored US probe may not be in the ideal position. The force sensor is can aid in effective scanning and can reduce safety issues. For the former, the US probe on the slave side may not tightly contact the leg, and thus the US image of the leg may be obtained, or the quality may not be sufficient. For the latter, the US probe on the slave side may put an undesirably large force on the leg. Also, integrating the force sensor on the slave side can facilitate the control of slave robot arm.

Example 3: Active Echo, a New Paradigm for Ultrasound Calibration

Ultrasound (US) imaging systems are widely integrated with tracking or robotic systems in medical procedures for tool tracking and image guidance. To integrate US with a tracking system and perform more advanced forms of guidance, an US calibration process must be performed. The US transducer can be fixed to a rigid body that can be tracked in some external coordinate system. The tracking is usually done by an optical marker, an electromagnetic (EM) sensor or the robot end-effector. The US calibration process determines the rigid body transformation relating the tracker to the US image, allowing an US image to be positioned in the tracking system base frame. Once calibrated, the US image is registered with any other tools or devices that are also being tracked in this base frame. Thus more advanced uses of the US system are possible, such as overlaying the image onto a video stream or actuating a tracked robotic actuator to target a region within the US image. The main drawback for US is its poor image quality relative to the other imaging modalities. This drawback often makes it difficult to accurately and automatically segment regions of interest within the images.

Figure 32:
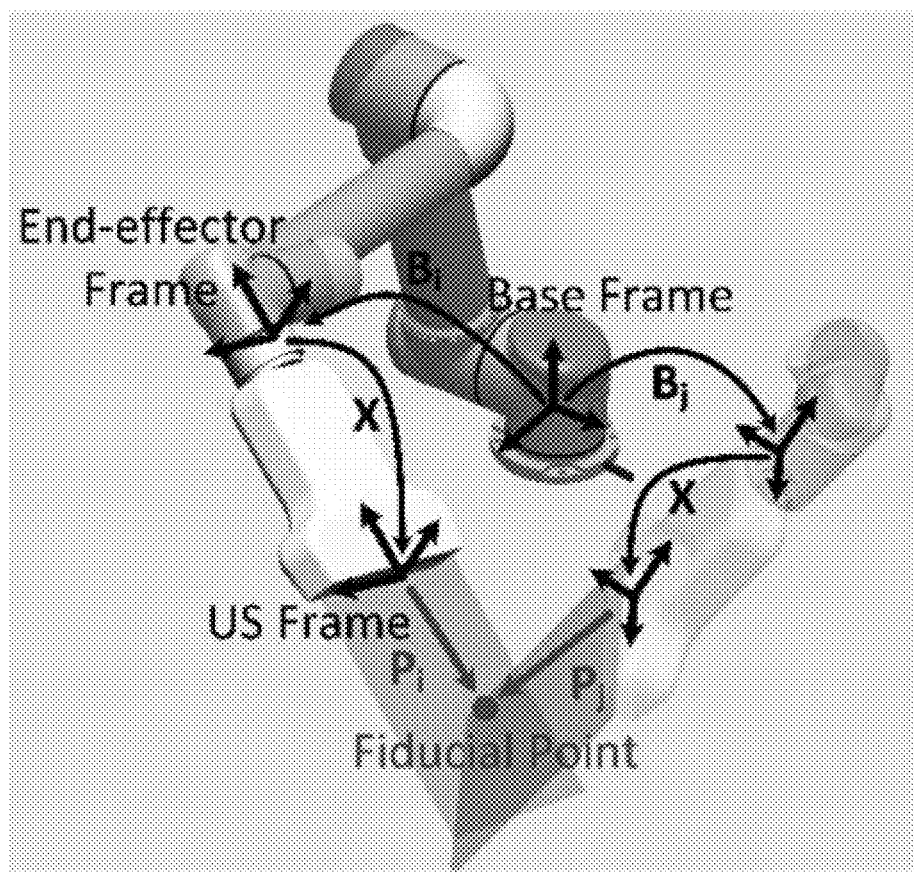
FIG. 32 illustrates the coordinate transformation in the BXp calibration using a robotic arm as the tracking system.

To find the transformation between the end-effector frame and the US image frame X, a specialized model or phantom with known configurations is required. A crosswire (CW) is one of the most commonly used phantom for US calibration [1]. With two wires crossing at a single point, it is a typical form of BXp US calibration, in which a single fiducial is imaged by a tracked US probe in different poses [2-5]. In this equation p is the fiducial point in the sensor coordinate, B is the transformation measured by the tracking system, and X is the unknown desired homogeneous transformation. Since all $(B_i, B_j)$ pairs are measured for the same physical point, the relationship $B_i X p_i = B_j X p_j$ holds for all combinations of i and j. FIG. 32 shows the situation where US images of the CW point are accumulated in various poses. One then uses these poses and the segmented points in the US images to reconstruct a single point in the external tracker's space. A limitation that prevents one from getting good calibration accuracy using this method is the US image plane thickness. In US imaging, the US beam transmitted from a probe usually has a width of several millimeters to centimeters dependent on the depth and other imaging parameters. As a result, it is difficult to distinguish whether an object in the B-mode image is intersecting the mid-plane. Since the localization and segmentation completely rely on the US image in conventional calibration phantoms, the elevation axis positioning uncertainty coupled with the relatively low quality of US image result in a reconstruction precision that can easily be worse than a few millimeters. Moreover, this is a user dependent procedure as the operator's experience greatly affects the calibration accuracy.

Figures 33, 34:
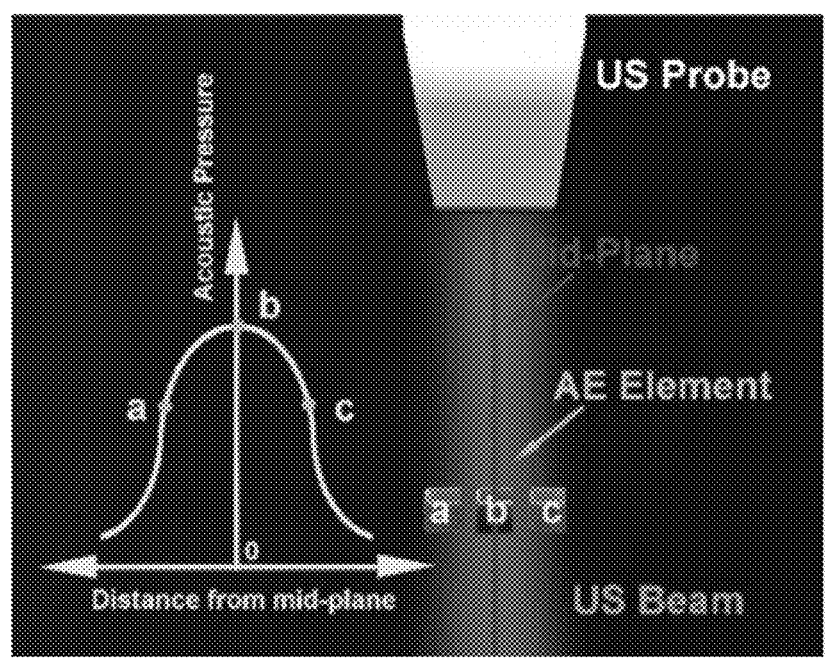
FIG. 33 illustrates the use of an active echo (AE) element for the mid-plane localization.
FIG. 34 shows repeatability for Xs computed with segmented AE and CW points.

Guo et al [6] demonstrated an interventional tool tracking and guiding technique active ultrasound pattern injection system (AUSPIS) that solves both the object visualization and mid-plane error problem at the same time. In AUSPIS, an active echo (AE) element, which acts as a miniaturized US transducer, is integrated with the target object that needs to be tracked in US images. An electrical system composed of a US receiver, a signal processor, and a pulser is connected to the AE element. When the US system is acquiring a B-mode image, probe elements fire sequentially to scan the entire field of view (FOV). An AE element in the FOV will sense the beacon pulse when the transmission beam scans over. To improve the tool visualization, the AUSPIS will drive the AE element to send an US pulse immediately after the beacon reception. Since the reception-transmission delay is in nanoseconds and is negligible for US imaging, the US pulse is superimposed on the reflected wave, resulting in an enhanced echo pulse with a much higher amplitude, configurable frequency and wider emission angle. This wave travels back to the imaging probe and appears as a bright spot (AE spot) that indicates the AE element location in the B-mode image. Another function of AUSPIS is localizing the US mid-plane by measuring the local US signal intensity, as shown in FIG. 33. At position b, the AE element receives the maximum ultrasound signal amplitude. At a and c, although the element is still shown in the US image, the received signal amplitude is lower compared to b.

Since the AE element is a point that can be localized in an US image accurately, especially along the elevation axis, it is possible to use it in the same way as the CW point for US calibration. Practically, one procedure of finding the mid-plane can be done in three steps. The first step is to move the US probe until the AE element is shown in the B-mode image. The second step is to finely adjust the probe position until the AE element fires active US pulses, which is an indication that the received signal amplitude exceeds the pre-selected AE response threshold. The final step is to increase the threshold and adjust the probe position at the same time, until reaching a position that any small adjustment from this position will stop the active echo response. Another procedure of finding the mid-plane is to use the virtual pattern injection technique. AUSPIS measures the beacon intensity and injects a corresponding number of virtual bars into the B-mode image to indicate the signal strength. The mid-plane can be localized by simply moving the probe and finding the maximum number of bars. With the mid-plane detection feedback from AUSPIS, more accurate and user independent positioning can be achieved along the elevation axis, and thus we expect a better and more consistent calibration precision using this method.

There were several hypothesis that we wanted to test by performing several CW and AE experiments. The first hypothesis is that the localization of AE points within the ultrasound image mid-plane is more user-independent than the CW points. To test this hypothesis, we conducted an experiment where users repeatedly approached the CW and AE points respectively using the robot-actuated ultrasound probe. The robot motion was restricted to a single dimension such that the two points pass a similar region of the ultrasound beam transmission profile. In this experiment, the user would stop the robot motion and record the robot pose when they felt the AE or CW point was accurately in the ultrasound image's mid-plane. A total of thirty-five poses were recorded for the AE and CW points respectively. From our initial hypothesis, we would expect the standard deviation of the robot poses to be smaller when imaging the AE point than when imaging the CW point.

The second hypothesis is that the calibration done using AE points is less affected by segmentation errors than when using CW points. To test this hypothesis, we collected sixty CW point and sixty AE point images with their respective robot poses. Two users segmented each of the two data sets by manually choosing the CW and AE element points on B-mode images, and repeated this for a total of ten times. The ten CW data sets and the ten AE data sets were independently used to solve for X, the transformation relating the robot end effector to the ultrasound image plane. We used a variant of the gradient descent solver described by Ackerman et al. [7] with a cost function that minimizes every pair of $|B_iXp_i-B_jXp_j|=0$. This resulted in ten Xs each using either the CW points or AE points. The repeatability of these ten Xs was tested using a version of the method described by Treece et al. [8]. The US image corners are transformed by each X and the standard deviations of the resulting point clouds at each corner is reported with †i,norm $(std(\{X_1c_i, \ldots, X_mc_i\}))$. It is expected that these standard deviations will be lower for the Xs computed using the segmented AE points.

The third hypothesis is that the calibration using AE points has a better point reconstruction precision than the calibration using CW points. To test this, we used the segmented points and the Xs acquired to test the second hypothesis. Each set of segmented CW points are used to test each of the AE Xs and vice versa. The point reconstruction precision is computed by $norm(std(\{B_1Xp_i, \ldots, B_kXp_k\}))$. For example, to compute this metric for the AE X, the robot poses imaging the crosswire and corresponding points would be B and p, respectively. We compare the AE X and the CW X with the best reconstruction precisions in their respective sets. The expectation is that the AE X will have a better reconstruction precision. The datasets collected for the fourth and fifth hypothesis were also used to test this hypothesis.

Before we describe the fourth hypothesis, we introduce two additional compo-nents used in the experiment. The first is the use of fiber optical hydrophone points as the test data set. By principle, any US sensor can be used as a reception-only AE element for mid-plane localization. Since the mid-plane position is determined by the detected spatial acoustic pressure distribution, a smaller sensor has higher spatial resolution, and results in a higher mid-plane detection accuracy. Fiber optical hydro-phones have an effective aperture of as small as 10 μm, and were previously shown by Guo et al. [6] to have better localization than the PZT AE points. Using these points as the point reconstruction test points allow us to further isolate the error in the calibration X from other errors. The second is the automatic segmentation. The active phantom is able to provide both US and electrical feedback when the US probe is aligned with the target point. This enables several methods, like the beacon delay method, frequency modulation method, and time modulation method, to segment the points automatically by the electronics or software. We focus on the first one herein, and leave the other methods for future investigation.

In the beacon delay method, the US system outputs two TTL triggers for the RF line and frame synchronization. The AE electronic system receives these two triggers and compares them with the signal received by the AE element. For the axial direction, the system measures the delay between a line trigger and the corresponding beacon signal received by the AE element to get the TOF. So the axial distance can be determined by multiplying the TOF with the speed of sound. Practically, the AE element may receive signals from multiple neighboring RF lines, and the system will use the one with the shortest delay as the TOF. For the lateral direction, once a frame trigger is received, the device will start counting the number of line triggers until a TOF is received, and the count will be recorded as $n_{tof}$. So the axial distance can be determined by $y=L_{probe}*n_{tof}/n_{total}$, where $L_{probe}$ is the array length, and $n_{total}$ is the total line triggers in each frame. By using this method, the point segmentation becomes entirely image and user-independent.

The fourth hypothesis is that the automatically segmented AE points result in a calibration comparable to manual CW and AE expert segmentation. To test this, we compare the point reconstruction precisions of the CW X, AE X, and the automatically segmented AE X with our third experimental dataset using sixty optical hydro-phone points as the test data set.

The final hypothesis is that Xs constructed from subsets of CW data will vary more than Xs constructed from subsets of AE data. To test this, we take some subset of the data and compute a X. We repeat this one hundred times for the CW, the AE, and the auto-segmented AE. The metric we use for this test is the point reconstruction precision.

One important note in the last hypothesis is that the subset of data for the CW and the AE contain very similar motions. This is only possible with the use of the robot arm as it allows us to have consistent motions between various apparatus. The robot also has a higher accuracy than other tracking systems such as electromagnetic or optical trackers. However, the proposed calibration method is generally applicable to other external trackers as well. Moreover, since the system is capable of detecting in-plane conditions, it is possible to trigger the image and tracking data capture automatically once the element is in-plane without holding the probe in position. So it potentially can make the calibration process easier and faster with any tracking system.

The experiment is performed in a water tank. An AE element and a CW phantom are placed side by side at the same height in the water tank. A Sonix Touch system and a 58.5 mm L14-5W probe (Ultrasonix Inc.) are used to acquire a 9 cm depth US image. The probe is attached to a UR5 robotic arm (Universal Robots Inc.), which has 6 degrees of freedom and an end-effector positioning repeatability of ±100 μm. The AE element is made of a customized PZT5H tube with an outer diameter of 2.08 mm, an inner diameter of 1.47 mm, and a length of 2 mm. The electronic system includes a transmit/receive switch, an impedance matching circuit, a variable gain amplifier, filters, a triggering circuit, an analog to digital converter, a microprocessor and a pulser. The CW phantom is made of two 0.2 mm fishing lines. A fiber optical hydrophone (OH) developed by Precision Acoustics LTD is also integrated as a reference phantom. This device has a micro Fabry-Pérot acoustic sensor fabricated on a fiber tip [9]. It has a receiving aperture of 10 μm, a bandwidth of 0.25-50 MHz, a dynamic range of 0.01-15 MPa, and a sensitivity of 150 mV/MPa.

The localization precisions as described in the experiment for our first hypothesis are 371 μm and 223 μm for CW and AE, respectively. The localization precision is computed by taking the standard deviations in the robot motion dimension of the recorded robot poses.

Figure 35:
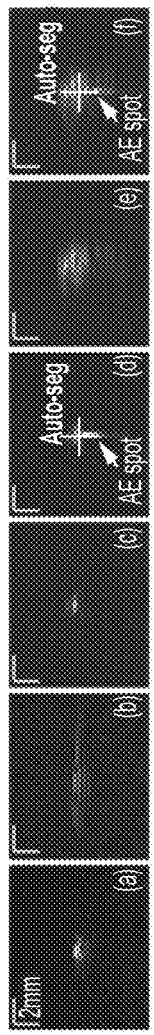
FIG. 35 shows best point reconstruction precision for Xs computed with calibration and test data.

The table in FIG. 34 shows the repeatability of the Xs as described in the experiment for our second hypothesis. The corners are chosen to correspond with the ultrasound image dimensions. Three experiments were performed to test our third hypothesis. In the first experiment, the quality of the collected images is low for both CW and AE, mainly due to the multi-reflection and unfocused beam. The data resulted in point reconstruction precisions of 2.36 mm and 1.05 mm for CW and AE, respectively. In experiment 2 and 3, the experimental setup is configured to optimize the image quality. The results are shown in columns AE/CW and CW/OPT in the table in FIG. 35. The results for our fourth hypothesis are also shown in FIG. 35. Data from experiment 1 is not directly compared to 2 and 3 as the difference in image quality.

The results for our first hypothesis show that the AE points can indeed be localized more precisely in the ultrasound image mid-plane than the CW points. We can see that the localization precision is significantly better for the AE points than the CW points. Also, the results in FIG. 34 show that the Xs computed using different segmentations of the AE images are more repeatable than those of the CW images. This was true for each of the four corners of the ultrasound image.

FIG. 35 shows that we can achieve comparable point reconstruction precisions using AE calibration and CW calibration. This contradicts our initial hypothesis of better point reconstruction precision. The comparison is especially obvious when we observe FIG. 35 when the same optical hydrophone test set is used for both calibrations. However, we must note here that the current AE setup is not ideal. We are limited by the available piezoelectric components, so the AE element used in this experiment is fairly large in size, resulting in a receiving aperture of around 2 mm. This is a major factor that prevents us from getting a higher mid-plane localization accuracy. Also, compared with the CW phantom, the AE phantom has the drawback that when the US image plane is far away, it is unable to provide any feedback regarding the distance. A better implementation in the future could be a hybrid phantom, in which a miniaturized AE element is integrated on the CW. One can then use the wires to guide the probe to the CW point, and use the AE feedback to finely adjust for the mid-plane.

FIGS. 36A-36F show the US images of CW and AE phantoms under different conditions. FIGS. 36A and 36B show images of a CW point, and FIGS. 36C-36F show images of an AE phantom. The images in 36A, 36C, and 36D are acquired at 4 cm depth, normal angle and in-focus condition. The images in 36B, 36E, and 3F are acquired at 8 cm depth, large incident angle and off-focus condition. For FIGS. 36D and 36F, the active echo is enabled. The auto-segmentation result is also marked on the figure. For FIGS. 36B, 36E, and 36F, the image quality is low and it is difficult to perform accurate manual segmentation. As shown in FIGS. 36D and 36F, the AE spot can provide a visual cue of the element position, simplifying the manual segmentation. Moreover, image quality dependency can be completely eliminated with automatic segmentation, as shown by the red markers in FIGS. 36D and 36F. In the figures, the marker position is not on the center of the AE element because the image is mainly formed by the top surface of the element. The auto-segmentation marker represents the element's geometric center.

Figure 37:
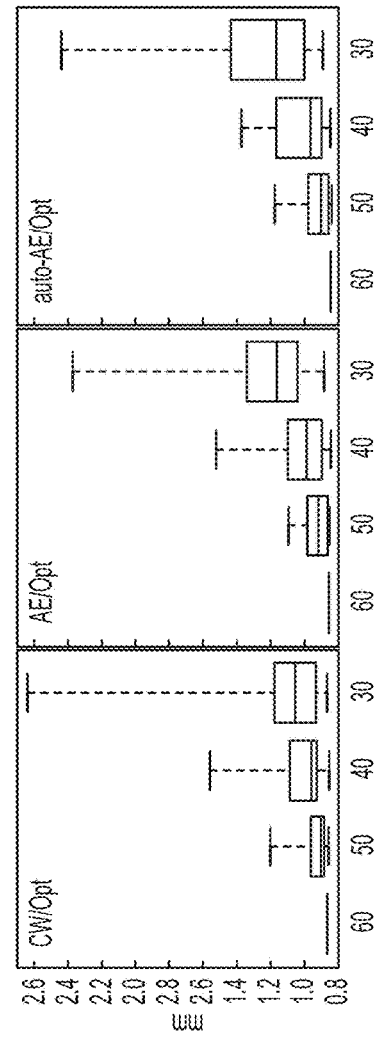
FIG. 37 shows a comparison of point reconstruction precisions as decreasing sizes of partial data subsets are used for CW, AE, and automatic AE calibration.

In the automatic segmentation test, we notice that a few of the auto segmented points are obviously away from the true AE element position by up to 0.4 mm. This is mainly because the AE element we use has a cylindrical shape, and does not have a symmetric signal response along certain angles. As a result, the maximum signal amplitude positions deviate from the element geometric center. This may be a possible reason why there is disagreement between the hypothesis and the results shown in FIG. 37. FIG. 37 shows a comparison of point reconstruction precisions as decreasing sizes of partial data subsets are used for CW, AE, and automatic AE calibration. In FIG. 37, the $25^{th}$ and $75^{th}$ quartiles are larger for automatic AE than CW for each of the tested number of sample points. Additional experiments will be required as one hundred random subsets of a certain size may not be enough to fully capture its behavior.

The AE system built in our lab includes a customized electronic system and an AE catheter. The overall material cost is less than $250, which is comparable to a typical 3D printed calibration phantom.

We have demonstrated herein the use of an active phantom for ultrasound calibration and have compared it to conventional CW calibration. We are able to show that AE points could be localized more precisely than CW points. AE calibration was also shown to be less affected by segmentation errors. We showed that AE calibration achieved a point reconstruction precision comparable to CW calibration. Finally, we demonstrated the fully automatic segmentation method with the same point reconstruction precision as manual segmentation.

In the examples above, the AE element may be replaced by a second US probe as shown in FIG. 3. The second US probe can transmit signals that are received by the first US probe. According to some embodiments of the invention, the first US probe is attached to the end of a first robotic manipulation arm, and the second US probe is attached to the end of a second robotic manipulation arm. The manipulation arms can be controlled by one or more robotic control systems. The position of the one of the probes can be fixed, and the robot control system can command the manipulation arm to move the other probe to various positions and poses until the unknown calibration matrices can be recovered. This process may then be repeated for the other probe. As shown in FIG. 3, an acoustic coupling medium can be positioned between the two probes. The coupling medium may be an ultrasound gel pad that is fixed to one of the probes.

Alternatively, the robot control system can command the manipulation arms to move both probes at the same time. Both probes can simultaneously send and received US signals, acquiring data to recover the unknown calibration matrices. The arms can move together while servoing a minimal acoustic coupling between both probes. In this case, and with enough motion, both US probes will be calibrated.

Example 4: Active Point Out-of-Plane Ultrasound Calibration

Image-guided surgery (IGS) systems are often used in modern surgical procedures to provide surgeons with additional information support and guidance leading to less trauma for the patient. Specific benefits to the patient can include reduced cost of the procedure, reduced morbidity rates, and shorter recovery times. In IGS systems, an intraoperative medical imaging modality is often used to provide a visualization of underlying tissue structures or anatomy that cannot be seen with the naked eye. We focus on the use of ultrasound (US) in IGS.

If one wants to use US to perform more advanced forms of guidance, an US calibration process must be performed. According to some embodiments of the invention, the first step for this process is rigidly attaching a tracked rigid body to the US transducer. The tracked rigid body can be an optical marker, an electromagnetic (EM) sensor, or a mechanically tracked attachment. The external tracker provides the tracked rigid body's pose, orientation and position, within the external tracker's coordinate frame. The US calibration process finds the rigid body transformation relating the tracked rigid body to the US image, allowing an US image to be positioned in the external tracker space. The US image is now registered with any other tools or devices that are also being tracked in this external tracker space. Once calibrated, more advanced uses of the US system are possible, such as overlaying the US image onto a video stream or actuating a tracked robotic actuator to target a region within the US image.

To find the tracked body to image transformation in the US calibration, a specialized model or phantom with known configurations or shape is required. There have been many different types of phantoms or models used for US calibration including wall [1], cross-wire [2], Z-fiducial [3], and AX=XB [4] phantoms. Of these phantoms, cross-wire phantoms are considered to be the most accurate. They are built such that two wires cross at a single point. US images of this point are then accumulated in a number of different tracked poses. One then uses these tracked poses, and the points in the US images resulting from imaging the cross-wire, to reconstruct a point in the external tracker's space.

There are two main disadvantages to using cross-wire or point based phantoms. The first disadvantage is the long acquisition time. Since the calibration framework relies on reconstructing a single point, the cross-wire or point must be accurately positioned in the image plane such that its elevational component is 0. Previous work showed that an active echo phantom [5] can provide feedback for in-plane positioning. However, feedback drastically increases the acquisition time because the operator now aims to minimize out-of-plane errors. Unless one uses the feedback to finely tune the point position, its utility is limited. The second disadvantage is that regardless of how finely one can tune the point position, there will still be out-of-plane errors that are generally unaccounted for. In this work, we present an extension of the active echo phantom to account for out-of-plane errors and decrease acquisition times. We describe herein the phantom, the data acquisition apparatus, the calibration algorithm, and finally simulation and experimental results.

The active phantom is an extension of the active echo phantom by Guo et al. [5], which is incorporated by reference herein in its entirety. According to some embodiments of the invention, the active phantom no longer responds to an US pulse and is instead always active and transmits US when it receives a trigger from a pulser. The US transducer now acts purely as a receiver and all of its transmissions are turned off. Since the US transmission from the active phantom is a one-way travel to the transducer, the standard beamforming on US machines will fail. Thus, it is necessary to acquire pre-beamformed channel data. We use an Ultrasonix Touch, SonixDAQ (Ultrasonix Corp., Richmond, Canada), and the MUSiiC Toolkit [6] to accomplish this.

This source of data also provides more information than standard beamformed data. The active point will appear as a wave-front in the image as opposed to a single point. We will describe how we can use this additional information to provide an estimate for out-of-plane localization. For our experiments, we use a linear L14-5/60 US transducer, but we will also briefly describe how using a curvilinear probe theoretically affects the algorithm. For our external tracker, we use a Universal Robots UR5 robot arm, providing a listed accuracy of 0.1 mm.

Figure 38:
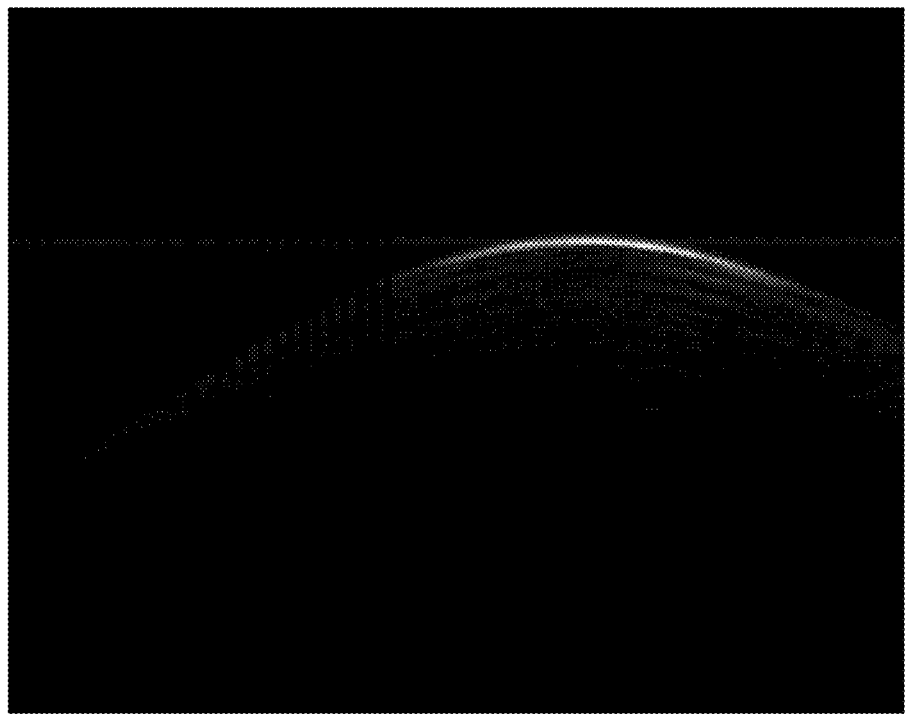
FIG. 38 shows a sample pre-beamformed US image with an active point present.

Out-of-plane active point estimation refers to the process of localizing an active point source based on its pre-beamformed channel data. In the pre-beamformed channel data, the active point will appear as a wave-front as seen in FIG. 38. Assuming that the active point is a perfect point source and the transducer elements are perfect point receivers, the wave-front represents a time of flight reading between the active point and each of the transducer elements. Thus, we gain a sense of distance between each transducer element and the active point by segmenting this wave-front. We can then apply a least squares 3D triangulation method on this set of distances to find the relative location of the active point with respect to the ultrasound image coordinate system. As can be seen in FIG. 38, the magnitude of the active point signal is much higher for some elements than others. It is prudent to reject the distance readings from elements with a low magnitude because the segmentation will likely be more inaccurate.

Equation 17 defines the general equation for performing least squares triangulation:

$$d_i^2 = \|e_i - p\|^2;$$

$$d_i^2 = (e_{ix} - p_x)^2 + (e_{iy} - p_y)^2 + (e_{iz} - p_z)^2. \quad (17)$$

Figure 39:
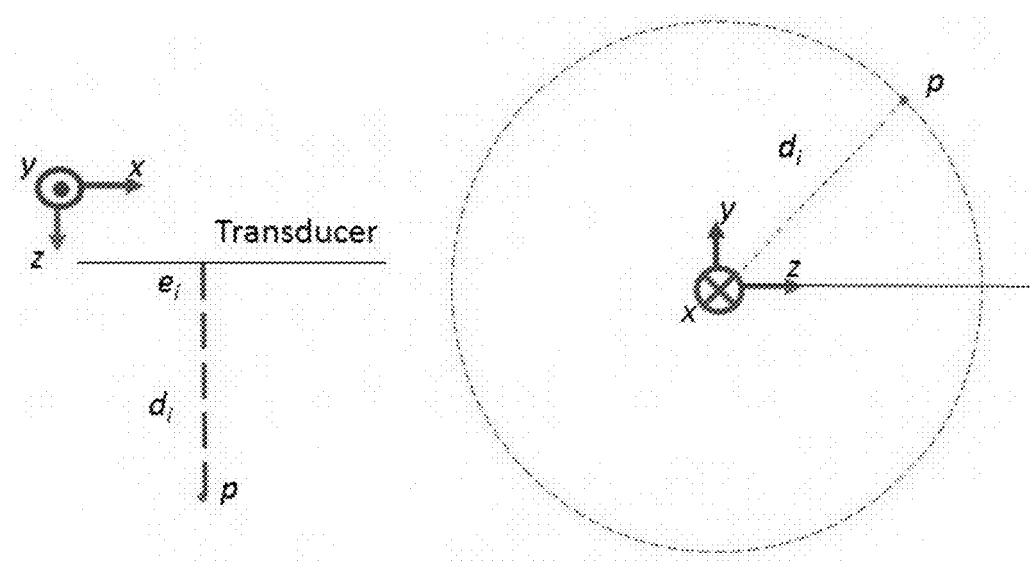
FIG. 39 illustrates the active point out-of-plane estimation concept.

As shown in FIG. 39, $d_i$ represents the wave-front distances for each element i. $e_i$ represents the position of transducer elements i in its local coordinate frame. p represents the 3D position of the active point in the transducer coordinate frame. This equation can be applied to both linear and curvilinear transducers, but there is a significant difference in the minimization result.

Equation 18 is the representation of equation 1 when using a linear transducer:

$$d_i^2 = (e_{ix} - p_x)^2 + p_y^2 + p_z^2. \quad (18)$$

Since the transducer elements are on a line, there is no axial or elevational component. We can easily see that there is one degree of freedom to satisfy this equation. The shortest distance between the transducer elements and the point results at $e_{ix} = p_x$. In this case, we can see that equation 18 becomes the equation of a circle in the elevational-axial plane at $e_{ix} = p_x$. From this geometry, we can also see that any $d_i$ not corresponding to $e_{ix} = p_x$ will not give any additional information to this problem. Thus, if given the lateral and axial position of this wave-front, we can also approximate a circle in the axial-elevational plane on which the point lies without using the entire wave-front or channel data.

Equation 19 is the representation of equation 17 when using a curvilinear transducer:

$$d_i^2 = (e_{ix} - p_x)^2 + p_y^2 + (e_{iz} - p_z)^2. \quad (19)$$

We can see that the main difference between this equation and equation 18 is the presence of an axial component in the transducer elements. This has a significant effect on the outcome as this equation can now be uniquely solved up to sign. The additional information will restrict the location of the point to a point on the circle, either in front of or behind the US image plane. It should be noted that this method of out-of-plane point estimation using a curvilinear transducer does require channel data.

The calibration algorithm will be described in the context of using a linear transducer, but it can also be applied in the curvilinear case. As previously mentioned, there is a circle for each particular image where equation 18 is satisfied. Thus, the calibration algorithm attempts to find a calibration that minimizes the distances between the circles of each image. Using the full circle is obviously unnecessary, so one can define a subset of the circle based on a maximum distance away from the image plane. This maximum elevational distance is fairly important and will be discussed later. Since we now have a set of points per image instead of a single point, we now modify the standard algorithm used for point-based calibration.

Equation 20 is the standard approach for solving point-based calibration.

$$\forall\, i = 1 \ldots n,\; \min_{X \in SE[3], c \in R^3} (\|c - B_i X p_i\|) \qquad (20)$$

$B_i$ is the pose recorded by the external tracker, $p_i$ is the point observed in the image, X is the unknown calibration transformation, and c is the unknown fixed point in the external tracker's coordinate frame. A least squares solver can be used to compute both c and X. The main change in our algorithm is that this becomes an iterative process as seen in FIG. 40.

The first step is to solve for c and X as one would normally do while assuming that there is no out-of-plane uncertainty. This provides an initial estimate of c and X that we use in the next step. For i=1 . . . n, we find $p_i$ belonging in the predetermined subset of points that minimizes the difference between $c_i$ and $B_i X p_i$ using the current estimate of c and X. This new set of p is then used in conjunction with the original set of B to solve for a new c and X. These two steps repeat until X converges and its change in an iteration reaches some predefined tolerance level. The same algorithm applies to curvilinear transducer calibration. The only difference is that the predetermined subset of points is now just the uniquely solved point and its negative on the other side of the US image plane. In theory, this means that the algorithm will converge much more quickly when using a curvilinear transducer as opposed to a linear transducer.

We perform both simulations and experiments to demonstrate the feasibility for this method. In this work, we simulate the theoretical geometry based on our assumptions of ideal point transmitter and receivers. In our simulation, we observe the effects of changes on two parameters. The first is the amount of elevational distance that the point is from the US image plane. The second is the standard deviation of the noise added to the distances between the active point and each of the transducer elements. In this simulation, we compare three things: how close our estimated out-of-plane points are to the true points, how close our calibration is to the true transformation and the point reconstruction precision.

We currently compute a slightly modified point reconstruction precision. In our experiment, we separate our data into two sets, one for computing the calibration, and the other for computing point reconstruction precision. We divide the data by picking the set of points that are estimated to be within 1 mm of the US image mid-plane as our test points. To perform this estimation, one needs to first run the calibration process on all of these points. After this step, the remaining points are used to re-compute the calibration. This calibration is then applied to the previously removed test points.

Figures 43, 44:
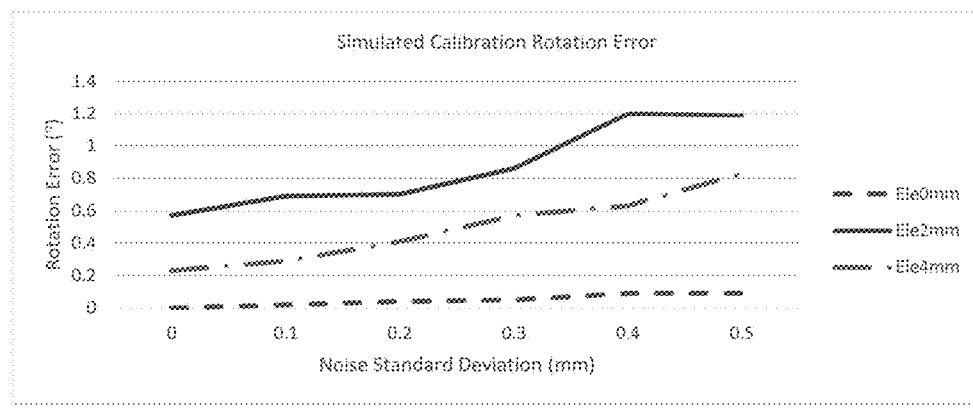
FIG. 43 shows a table of the Simulated calibration estimation error (Rotation (°), Translation (mm))
FIG. 44 plots the simulated calibration rotation error.
Figures 45, 46:
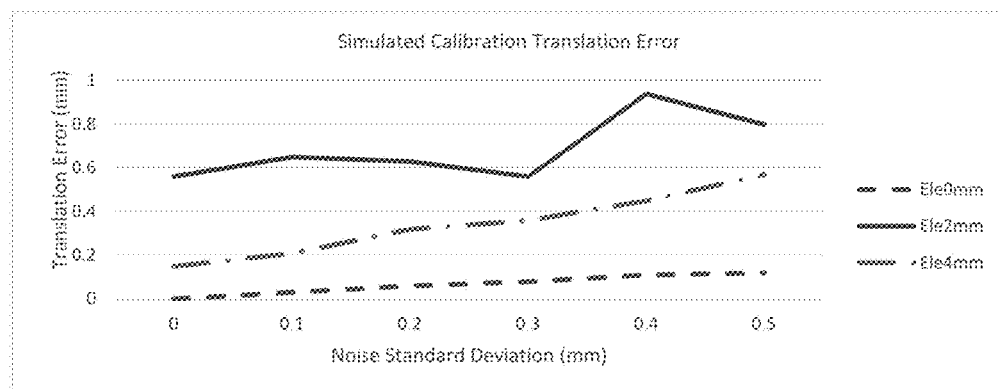
FIG. 45 plots the simulated calibration translation error.
FIG. 46 is a table showing the simulated point reconstruction precision (mm)

The table in FIG. 41 shows the mean and standard deviation of the distance between the estimated out-of-plane point and the true out-of-plane point as we changed the elevational distance of the point and as we changed the amount of added noise. FIG. 42 is the graphical representation of the data in the table in FIG. 41. The table in FIG. 43 shows the mean and standard deviation of the rotational and translational differences between the true X and the computed X as we changed those same parameters. FIGS. 44 and 45 are the graphical representations of the data in the table in FIG. 43.

Figure 47:
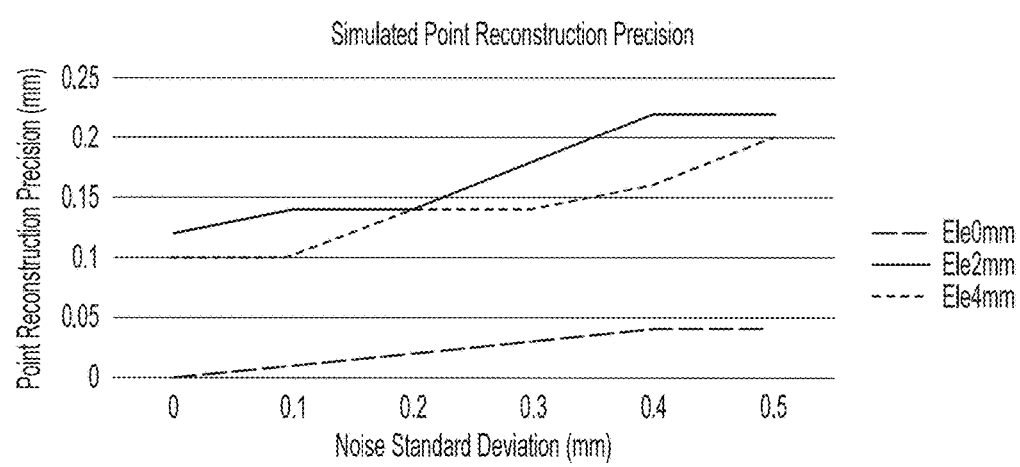
FIG. 47 plots the simulated point reconstruction precision.

The table in FIG. 46 shows the simulated point reconstruction precision. An independent set of points is transformed by the computed X. We then compute the standard deviation of the resulting point cloud as the point reconstruction precision for a single trial. FIG. 47 is the graphical representation of the data in the table in FIG. 46. The experimental test points are used to generate a point reconstruction precision of 0.64 mm.

From table 1, we see that this approach can be used to estimate out-of-plane points in our simulation conditions. We can see that the absolute error grows as the points are more out-of-plane. However, the ratio between the error and the elevational distance actually decreases as we increase the distance. This means that, while the absolute error increases, the relative change in error decreases as there is more uncertainty. We also see that the error increases with the noise.

From FIG. 41 we see that this approach can be used to compute the overall calibration. An interesting observation is that the errors actually decrease as the points are further away from the US image plane. This is likely due to there being a larger range of poses as we relax the restrictions placed on the active point position.

We can see that the table in FIG. 43 agrees with the table in FIG. 46. A larger calibration estimation error results in larger point reconstruction precisions. From our experimental result, we also see that we had a larger error than in simulation. While this is mostly expected, one very likely reason is the assumptions that we originally made in our algorithm and simulation. The ultrasound transducer and active point are not ideal point sources in reality. Since the equations assume otherwise, we naturally expect there to be deviations between simulation and reality. The future work for this would be to use a simulation environment that better resembles reality. Creating the wave-fronts through image formation simulation as opposed to geometric simulation will aid us in determining the ideal model for estimating out-of-plane points.

Since we can now approximately localize out-of-plane active points for calibration, we can significantly decrease acquisition time. In previous work with active echo calibration[5], one needed to place the active echo point in the ultrasound mid-plane based on feedback. This can be a time-consuming process. With the present approach, we can now approximately place the active point in the ultrasound mid-plane and estimate for out-of-plane deviations. The feedback is still useful, but fine-tuning the position generally takes significantly more time than getting to the general area.

An observation that we had over the course of our experiments was that this algorithm can be prone to overfitting. As we previously mentioned, we select a subset of the circle with some maximum elevational distance. Increasing this distance will almost always allow for a better least squares fit. Thus, one needs to apply caution when picking this parameter and should choose it to fit the actual experimental scenario. We currently apply a static parameter to all of the images in our dataset, but one can envision an algorithm which uses a variable parameter based on some other notion of distance away from the ultrasound image mid-plane. One example of feedback that can facilitate this would be signal intensity, as it decreases the further away the active point is from the mid-plane. Another possibility is to use the active echo feedback described by Guo et al. [5]. While this approach can theoretically account for points of any out-of-plane distance, an alternative embodiment attempts to place the active point in the ultrasound mid-plane and to use this approach as a slight adjustment.

Example 5: Co-Robotic Ultrasound Tomography: Dual Arm Setup and Error Analysis

Most clinically available US systems provide A reflection US image and its varieties. However, reflection US imaging may miss some of the useful information that can be measured by tomographic US imaging [1]. In US tomographic imaging [1-10], the transmitter and receiver transducers are located at different known positions with respect to an insonified volume and the received signal can be used to reconstruct the volume's acoustic properties such as speed of sound and attenuation. Previous attempts to allow US tomography have shown to be effective in breast cancer detection and diagnosis [1-6]. Duric et al [1] used a circular array of US transducers in which at each time, one element transmits and others receive. This process is then repeated with a different element transmitting sequentially. Given that the geometry of the circular array of transducers is known, the radiological paths [11] can be reconstructed. This geometrical information, together with the received signal properties, such as time of flight and amplitude, are used to reconstruct tissue acoustic properties.

Another setup for tomographic US was investigated by several other groups [7-9]. Since an US probe, consists of an array of US transducers, two of such probes can be aligned along their axial axes to produce tomographic images. Aligning two probes manually is a challenging task. Hence we previously proposed robot assisted US tomography for tomographic US imaging using two conventional US probes, one operated by the sonographer as freehand and the other one moved by a robotic arm which stays aligned with the freehand probe [12]. Such systems will also facilitate tomographic reconstruction for more general examinations.

We describe herein a new system setup for robot assistance in US tomographic imaging. Compared to our previous setup, the dual arm system does not require line of sight for tracking, it has the potential to be used as a fully robotic system or in a cooperative mode, and it provides the operator with the option to fix the cooperative probe for tomographic imaging after the area of interest is found.

In the robot assisted US tomography system according to some embodiments of the invention, one of the robotic arms is controlled by the sonographer. Then the other robotic arm can align the second US probe automatically. To enable such alignment, accurate calibrations between the two probes are performed beforehand. Once the two probes are aligned, the US waves can be transmitted by one probe and received by the other probe to allow for tomographic image reconstruction.

We describe herein an algorithm for reconstructing speed of sound in US tomographic images using two aligned linear probes. The method is, however, prone to positioning inaccuracies. We provide an analysis on how the tracking error propagates through the whole system and how the in-plane translational error affects the tomographic reconstruction.

Figures 48A, 48B:
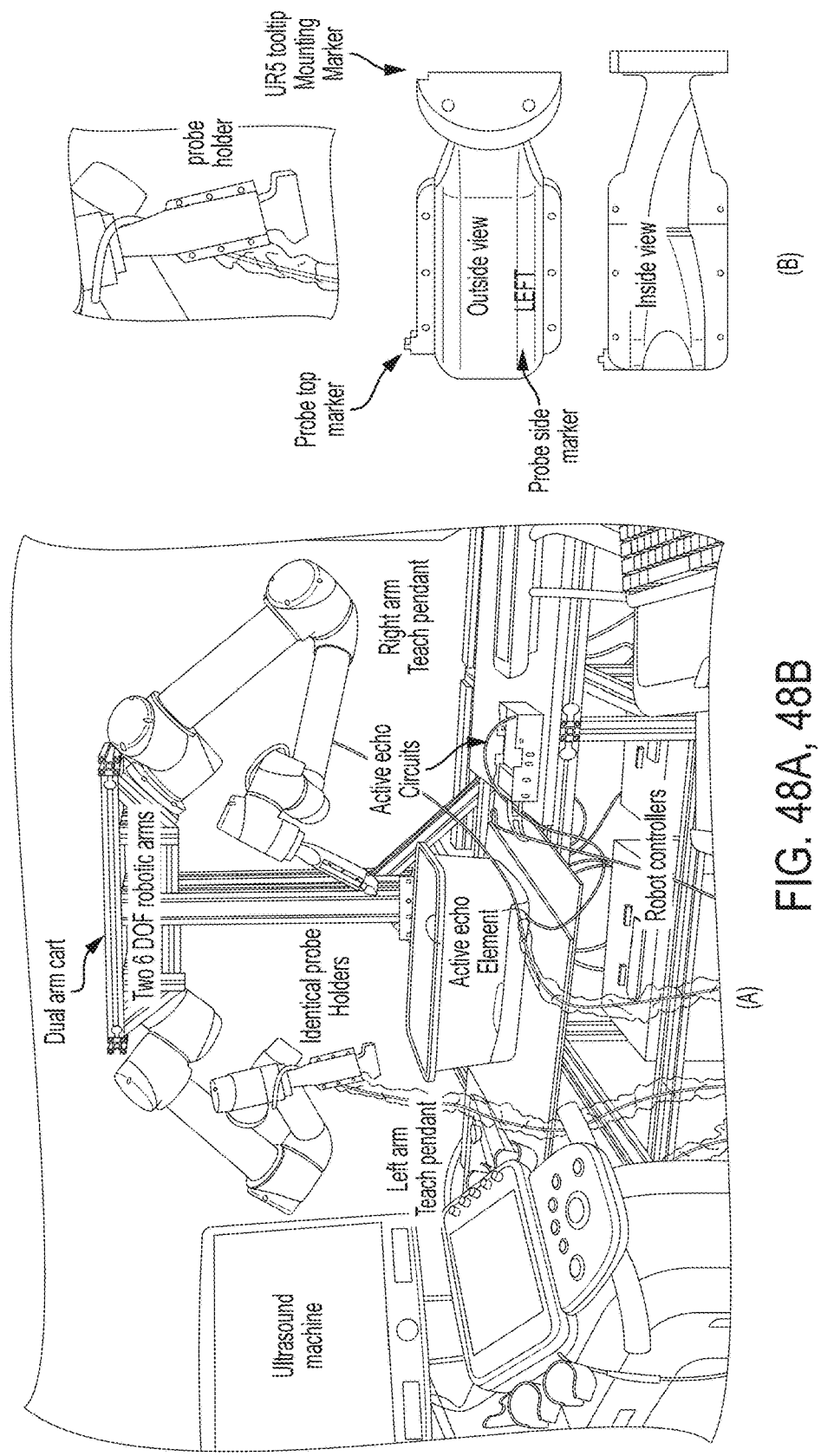
FIG. 48A shows the dual robotic arm US tomography system components and setup for calibrations according to some embodiments of the invention.
FIG. 48B shows the probe holders and the designed markers to enhance repeatability of the attachment.

The dual arm system setup according to some embodiments of the invention consists of two robotic arms and two US probes, as shown in FIGS. 48A and 48B. One of the arms can be operated in cooperative mode with the technician while the other one automatically aligns with it. To calculate the desired pose of the second arm, several calibrations are required.

We use two six degrees of freedom UR5 robotic arms (Universal Robots, Odense, Denmark) which have 850 mm in radius spherical reach, and 0.1 mm repeatability. Each arm has a 149 mm in diameter circular base and 75 mm in diameter circular tooltip. UR5 is an 18.4 kg lightweight robotic arm. We have designed and manufactured a portable dual arm cart, as shown in FIG. 48A, where the two robotic arms can be installed. There is a space on the lower part of the cart to put the robot controllers.

Two identical 60 mm 128 array linear Ultrasonix US probes, together with the Sonix Touch US machine (Analogic Ultrasound, Richmond, BC, Canada) are used. We have designed and manufactured US probe holders that enable the attachment of the US probe to the robot tooltip. FIG. 48B shows the designed holder from different views. The holders were 3d printed using ABS material. It should be noted that detaching and attaching the probe holders in a different orientation invalidates the calibrations. Hence, the probe holders have some markers to make the attachment as reproducible as possible. However, even untightening the holders' screws may degrade the calibration accuracies in the millimeter range.

Figure 49:
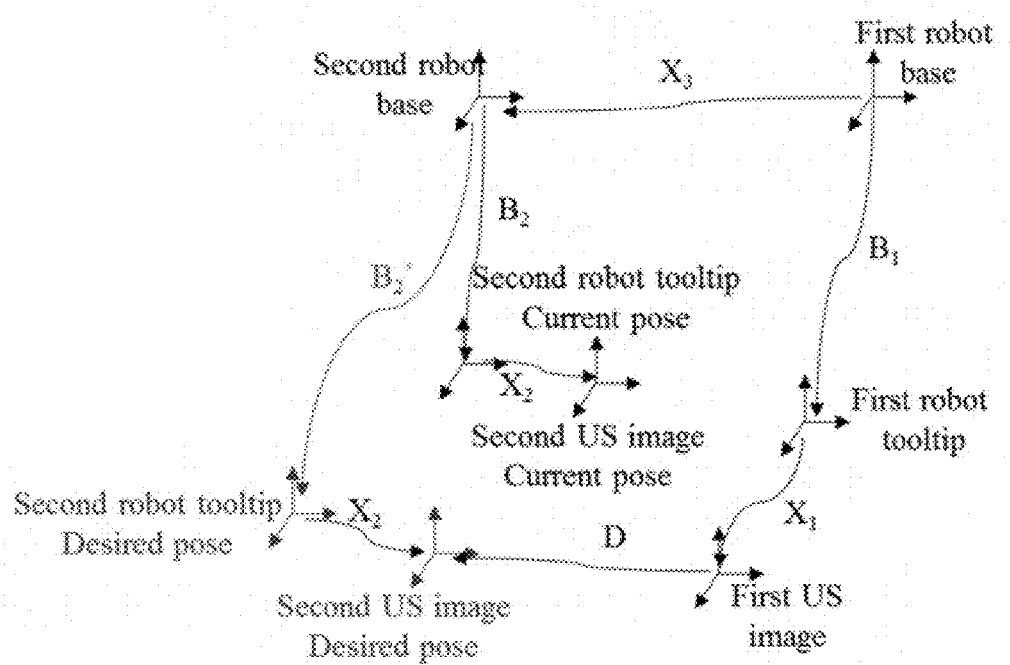
FIG. 49 illustrates transformations involved in calculating the desired second arm pose such that the two US probes are aligned.

As mentioned above, one of the robotic arms may be controlled by the technician. FIG. 49 illustrates transformations involved in calculating the desired second arm pose such that the two US probes are aligned. To calculate the desired pose, the following equation can be used:

$$B_2' = X_3^{-1} B_1 X_1 D X_2^{-1} \qquad (21)$$

where $B_2'$ is the desired pose for the second arm, $B_1$ is the first arm's pose, and D is the desired transformation from first US probe image frame to the second.

$B_1$ and $B_2$ can be read from robot encoders; however, $X_1$, $X_2$, and $X_3$ should be determined through calibrations. $X_1$ and $X_2$ are the transformation matrices from robot tooltips to US images and hence are called US calibrations. $X_3$ is the transformation between the two robotic arm bases.

To find $X_1$ and $X_2$, we used an active echo US calibration [13] (the active echo circuitry is shown in FIG. 48A). It is a point based calibration in which the active echo is imaged by the US probe from various poses. The active echo is an active miniaturized US element that listens to US signals. It sends back an US signal when it receives one. When the US probe's trigger signals are connected to the active echo circuitry, the probe can measure the delay between the time the US signal was transmitted by the US probe and the time it was received by the active echo element. In addition, the probe's element with minimum delay can be determined. These two parameters can be used to localize the active echo element in the US image coordinate frame.

To have an accurate US calibration, we need to ensure active echo is in the US image mid-plane. Hence, we moved the robotic arm to various poses, and at each pose, stored two readings: 1) the robot tooltip frame position and orientation in the robot base frame, and 2) the 2-D location of the active echo in the US image frame.

We collected 28 data points for each arm and used the gradient descent algorithm [14] to solve for $X_1$ and $X_2$. To evaluate the calibrations, for each arm we collected another data set, called test set, containing 9 data points. We consider the standard deviation of the reconstructed test points in the robot base frame as a representation of the calibrations' precision. The calculated reconstruction precisions are [1.47, 0.51, 0.22] and [1.66, 0.69, 0.91] mm for the left and right arms respectively.

We used the calculated $X_1$ and $X_2$ to calibrate the robot bases, i.e., to find $X_3$. We moved the active echo point to 15 different poses (not in a line), and at each pose, we aligned the US images using the two arms (one by one) with the active echo, and collected data. These points can then be reconstructed in the two robot bases (using $P_j^i = B_j^i X_j p_j^i$, j={1,2}, i={1:15} where $P_j^i$ is point i defined in robot base j, $B_j^i$ is the ith pose of jth robot tooltip in its base coordinate frame, and $p_j^i$ is the location of ith active echo in jth US image). Hence, we have 15 points defined in the two coordinate frames. We used point cloud to point cloud registration (with known correspondences) to solve for $X_3$. We also collected a test set to evaluate the calibration precision. We fixed the active echo at five different poses, then scanned it using the two arms, but this time, reconstructed the points in the first robot base ($P_1^k = B_1^k X_1 p_1^k$, $p_2^k = X_3 B_2^k X_2 p_2^k$, k={1:5}). The mean distance between the reconstructed points were considered as a representation of precision and was calculated as [3.30, 0.58, 1.67] mm.

Figure 50:
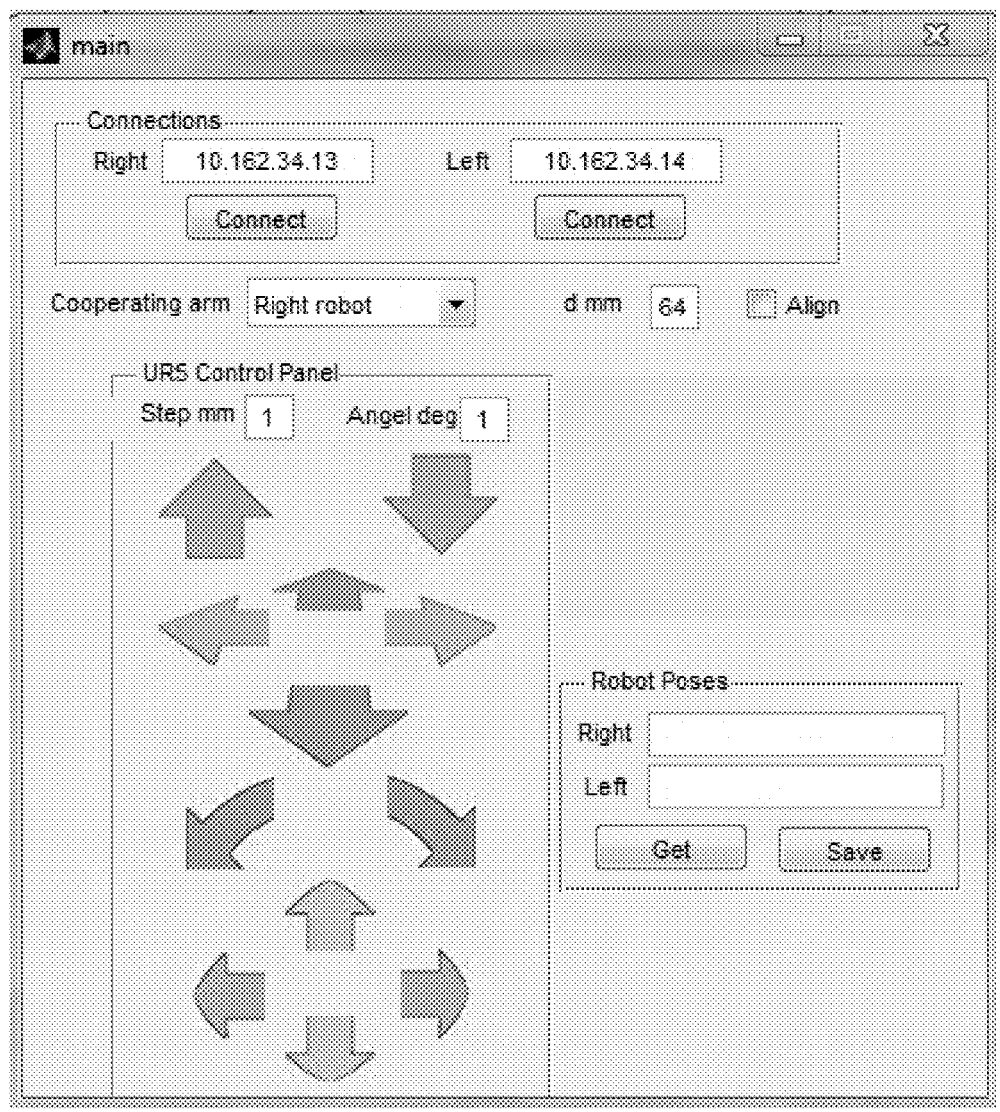
FIG. 50 is a screenshot of the alignment user interface.

We developed a graphical user interface in Matlab to cooperatively control the arms and enable automatic alignment. FIG. 50 shows a screenshot of the designed user interface. The user interface consists of several sections.

1. Connections: This part establishes an Ethernet connection between the user interface and robot control panel. A script on the robot control panel is written which can create a TCP/IP connection; send robot poses when requested; receive robot poses; and move the tooltip to the desired robot pose. The input to this section is the two controllers' IP addresses.

2. Settings: In this part, the user can determine which arm he/she wants to control. The other arm will automatically align with the cooperating arm if the Align box is checked.

3. UR5 Control Panel: This section of the interface simulates the UR5 control panel. The user can control the cooperating arm in all the six degrees of freedom and in US image axes using the buttons in this section.

4. After the movement is done, the control/display area, on the right side of the interface, can be used to save robot poses and display the transformation between the US images' frames.

In this section, we provide an algorithm for reconstructing speed of sound in the insonified area between two aligned linear arrays of US transmitters and receivers. The algorithm is based on one shot of transmitting and receiving between two perfectly aligned US probes when they are fixed in front of each other. Each probe contains an array of linearly positioned US transducer capable of both transmitting and receiving. One probe is selected as transmitter and the other one as receiver. The elements on the transmitting probe fire sequentially and send a trigger signal at the beginning of transmission. This trigger signal can be connected to the receiving probe to start collecting data. We assume that the US signal transmitted by each element can be received by all elements of the receiving probe.

Figure 51:
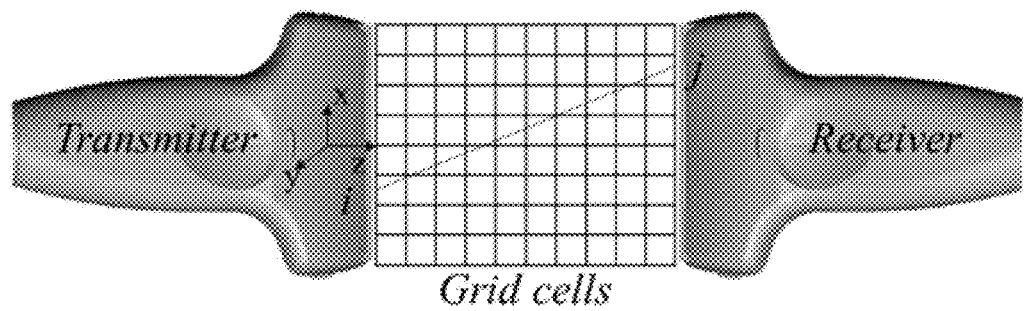
FIG. 51 depicts the insonified area divided into grid cells and one example transmit-receive ray from ith transmitter to the jth receiver.

The system matrix, S, contains the geometrical relation between the transmitters and receivers. The insonified area can be divided into grid cells, as shown in FIG. 51. The transmitters fire sequentially, and at each transmit firing, all the receivers are listening. The signal travels from one transmitter to all the receivers. FIG. 51 shows one example transmit-receive ray from ith transmitter to the jth receiver. There is a ray between each transmitter-receiver pair that passes through several grid cells. FIG. 51 also shows the image axes directions for transmitter.

The system matrix determines how much of each grid cell is passed by each ray. This matrix has $N_t \times N_r$ rows and $N_g$ columns, where $N_t$ is the number of transmitting elements, $N_r$ is the number of receiving elements, and $N_g$ is the total number of grid cells. Each row of the system matrix corresponds to one pair of transmitter-receiver, and contains the path lengths corresponding to each grid cell. We constructed a system matrix based on the method presented in [11] and using the US probe lateral size, the number of element in one probe, and the distance between the two probes. We ignored the elements' width or height and assumed the location of each transmitter/receiver is in the center.

Time of flight, tof, is a vector that contains the time it took the signal to travel from a transmitter to a receiver. This vector has $N_t \times N_r$ rows, where each row corresponds to one ray, i.e., one transmit-receive pair.

Our goal is to estimate the speed of sound in each cell of the grid, $v_i$, i={1:$N_g$}. Instead of directly calculating $v_i$, we calculate its inverse, $b_i$, which is called "slowness". The time required for an ultrasound signal to travel along a ray is equal to the sum of the time in all of the cells that it passes through. The time required to travel through one cell is t=l*b, where l is the path length along the cell, and b is the cell's slowness. Hence, $tof_j = \Sigma_{i=1}^n S_{i,j} * b_i$, where $tof_j$ is the total time of flight for the jth ray, $S_{i,j}$ is the path length of jth ray along ith cell, and $b_i$ is the ith cell slowness. This leads to solving the following equation for b:

$$S*b = tof \qquad (22)$$

where b is the slowness vector with $N_g$ rows.

Figure 52:
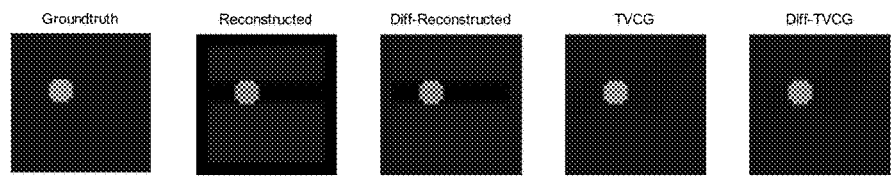
FIG. 52 shows ground-truth and reconstructed images without any inaccuracies or noise.

The number of unknowns is $N_g$ and the number of equations is $N_t \times N_r$ and the goal is to solve equation (2) for b. One way is to use pseudoinverse, i.e., $$b = pinv(S) * tof \qquad (23)$$

where pinv( ) is the Moore-Penrose pseudoinverse. However, Duric et al [3] found that this equation, in practice, is difficult to solve. More accurate results can be obtained if instead of absolute to f and b values (called Reconstructed in figures), their difference from a nominal value is measured (Diff-Reconstructed). In addition, to compensate for incomplete tomographic data and possible noise/error, we tested a total variation with conjugate gradient regularization algorithm [15] (TVCG and Diff-TVCG). We tested the tomographic reconstruction algorithm in simulation. A ground truth image was created by assigning a speed of sound of 1540 m/s for background and 1490 m/s for a circular area with a 6 mm diameter centered at [−5,0,12] mm in the image. The system matrix was reconstructed by considering 64 transmitting and 64 receiving elements, each with 30 mm lateral length and positioned at an axial distance of 30 mm (we assumed half of the real probe dimensions for faster simulations). The transmitters and receivers are considered to have a negligible width and are put side by side with 0.4688 mm distance between them. The ground-truth image is shown in FIG. 52. The pixel intensities represent slowness for a speed of sound ranging from 1450 to 1550 m/s. As shown in FIG. 52, we first use the system matrix to produce the simulated time of flights, then calculate the speed of sound in grid cells using the absolute and differential pseudoinverse or regularized methods.

The reconstructed speed of sound in the absolute or difference methods are similar, when no noise exists. However, the regularized images have a more uniform estimated speed of sound in the background but have shadows around the reconstructed circular area. These figures, however, show the reconstruction results when no noise or inaccuracy in the alignment exists. In the next section, we provide an error propagation analysis to find the range of expected alignment inaccuracy and then show the effect of in-plane translational error on the image reconstruction.

In this section, our goal is to investigate the effect of tracking inaccuracies in the overall alignment. In other words, we are interested in analyzing the resulting error in the transformation matrix, D, between the two US image frames. By looking at FIG. 2, D can be calculated using the following equation:

$$D = X_1^{-1} B_1^{-1} X_3 B_2 X_2. \qquad (24)$$

Equation 24 holds when all the matrices are accurate. Considering inaccuracies, we have the following equation:

$$D\Delta D = \Delta X_1^{-1} X_1^{-1} \Delta B_1^{-1} B_1^{-1} X_3 \Delta X_3 B_2 \Delta B_2 X_2 \Delta X_2, \quad (25)$$

where ΔD is the measurement error in D. Similarly, other matrices have their own errors. By taking D to the right side we have the following equation:

$$\Delta D = D^{-1} \Delta X_1^{-1} X_1^{-1} \Delta B_1^{-1} B_1^{-1} X_3 \Delta X_3 B_2 \Delta B_2 X_2 \Delta X_2. \quad (26)$$

Here, we make the assumption that the desired D matrix is a rotation of 180 degrees about the x-axis and a translation along the z-axis. Ideally we want the two probes to be aligned in front of each other, i.e., the second probe's frame is rotated 180 degrees about the first frame's x-axis, and has an offset along their z-axis. We chose this translation randomly from [0,150] mm. We used the calibration matrices found for the setup and defined a random transformation matrix from the first robot base to its tooltip, $B_1$. Then we calculate $B_2$ using equation (24).

Based on the Rodrigues formula, every rigid-body rotation can be defined by a unit vector, co, as the axis of rotation, and a magnitude of rotation angle, θ:

$$R = e^{\theta \hat{\omega}} = I + \sin(\theta)\hat{\omega} + (1 - \cos(\theta))\hat{\omega}^2 \quad (27)$$

where $\hat{\omega}$ is the skew-symmetric matrix made from ω. When θ is a small value (as in the case of rotation errors), the above formula can be written as:

$$R \approx I + \theta \hat{\omega}. \quad (28)$$

We used this formula to define rotation errors. For $B_1$ and $B_2$, we consider a maximum rotation angle error of 1 degree (0.0175 radian), and a maximum translation error of 0.1 mm. Since the inaccuracy is not always at its maximum for the robot transformations, at each time we picked the current rotation and translation errors from zero to maximum error randomly. However, the calibration matrices have a constant error and hence their error matrices are defined using a constant magnitude of translational and angular error.

Figures 53A, 53B:
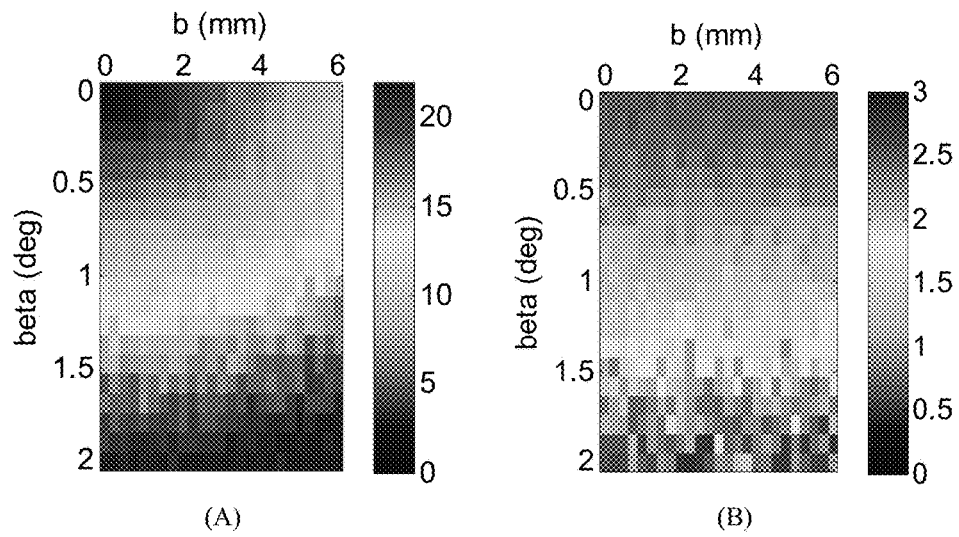
FIG. 53A shows the translational error in the transformation between the probes as a function of calibration errors.
FIG. 53B shows the rotational error (in degrees) in the transformation between the probes as a function of calibration errors.

It should be noted that the translational error is the norm of the errors in the three axes. The axes of rotational and translational errors were also picked randomly. Now, all the matrices in the right hand side of equation (26) are defined or randomly selected, hence, ΔD can be calculated. We repeated this process 20 times for each error value for the calibration matrices' errors (we assumed same error for all the three calibrations), 20 randomly selected other matrices, and got the average resulting translational and rotational errors derived from ΔD. FIGS. 53A and 53B show the results. FIG. 53A shows the translational error in the transformation between the probes as a function of calibration errors, and FIG. 53B shows rotational error (in degrees) in the transformation between the probes as a function of calibration errors.

Figure 54:
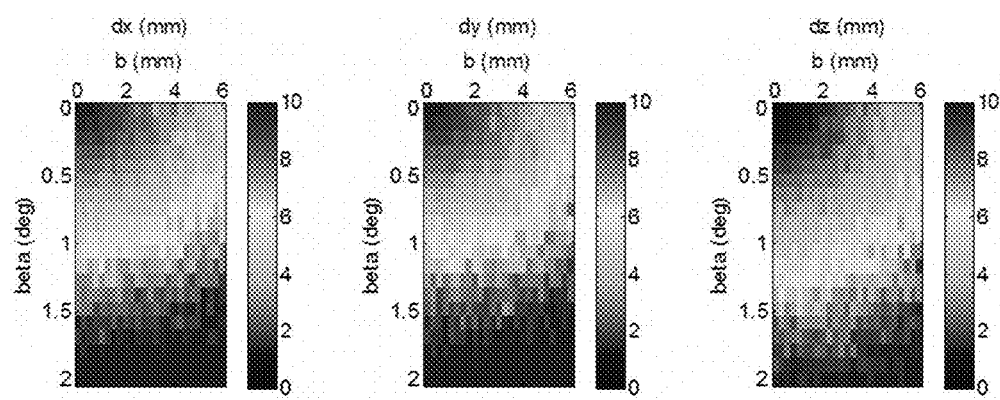
FIG. 54 shows the translational error of the transformation between the two US image coordinate frames for individual axes.
Figure 55:
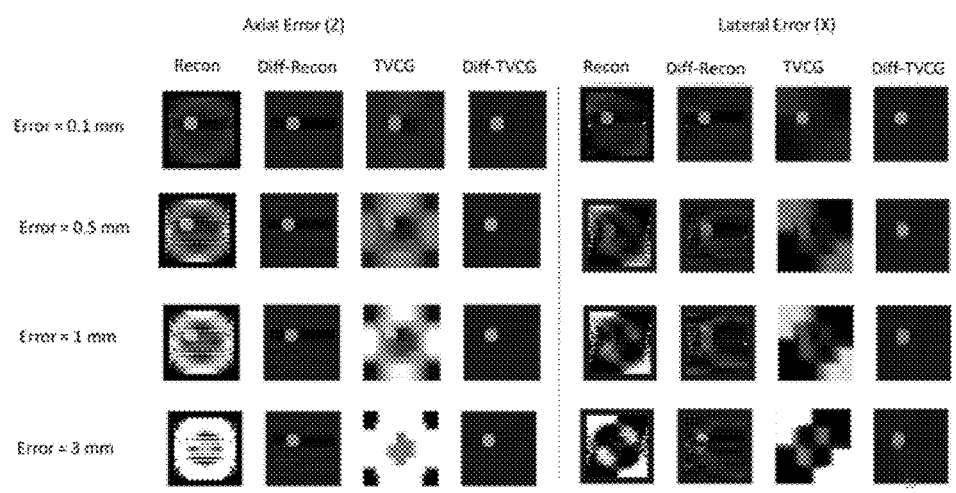
FIG. 55 shows the effect of the in-plane translational error on tomographic reconstruction for the expected range of errors.
Figures 56A, 56B, 56C:
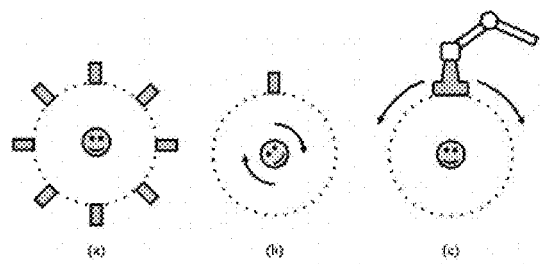
FIG. 56A illustrates a method of scanning in a circular geometry in which transducers are placed around the contrast agent.
FIG. 56B illustrates a method of scanning in a circular geometry by rotating the target.
FIG. 56C illustrates a method of scanning by moving the ultrasound transducer around the target using a robot arm

Focusing on the translation error, we can examine the error along each individual axis. FIG. 54 shows the decomposed translational error in the three axes. The axes are defined as shown in FIG. 3. The amount of the error is fairly similar among the three axes, though the axial error seems to be less than the other two axes). However, they might have different effects on the reconstruction. It is not easy to determine the error from the calculated precisions in the experimental setup. However, we can expect a translational error less than 4 mm, and assuming the rotational error is less than 0.5 degrees, the expected error in each axis will be around 3 mm. Here, we only applied the in-plane translational error on the reconstruction algorithm. The effect of out-of-plane and rotational errors can be investigated similarly, but requires the construction of the system matrix in three dimensions. As shown in FIG. 54, the absolute algorithms are very sensitive to any alignment error. The difference algorithms, especially the difference total variation regulaization (Diff-TVR), are the most robust methods. However, they require imaging of the background which may be difficult in a clinical setting.

Example 6: Study of Robotically Tracked Photoacoustic Computed Tomography

Photoacoustic imaging (PA) is becoming a promising imaging modality for pre-clinical and clinical applications by providing both functional information and depth information. As known from the literature, photoacoustic phenomenon can be initiated by laser, microwave or other thermoacoustic sources. In particular, PA computed tomography (PACT) aims to visualize the tomographic image of photoacoustic source distribution by scanning the surface of the target structure with an ultrasound transducer [1]. Circular scanning geometry is generally used to acquire a wide range of scanning angle, which enables high spatial resolution compared to linear scanning, and a full 360 degree scan is necessary to reconstruct the entire target. Placing transducers around the subject or rotating the subject with a fixed transducer position are two major approaches to scanning in a circular arc trajectory [2,3]. Circular array transducers enable a stable and fast scan because for a single laser emission, it is possible to receive signals from a full range simultaneously and the reconstruction can be applied on it. Rotating the subject is a simpler setup, and only a single element transducer and rotation station are required. However, both are not flexible and have their drawbacks. For example, dedicated customized setup requires to allocate ultrasound transducers in a round shape, and since the transducer has to be fixed, once the geometry is fixed, there is no flexibility to modify the scanning diameter based on the size or shape of the subject. For the case of rotating the subject, motion of the rotating object easily causes motion artifacts, and it is not practical to rotate large scale targets such as human subjects. Therefore, there is a demand for a simple and flexible scanning system for PACT. An array transducer is used as a flexible scanning system for PA tomography, but the problem is its limited view and incomplete reconstruction.

To resolve the problem, we developed a scanning method based on robotic tracking. A robot arm is used to hold an ultrasound transducer, and the motion of the transducer is regarded as its scanning path. Any trajectory can be created by moving the transducer to multiple positions. Received data from multiple poses can be accumulated simultaneously and put into a tomographic reconstruction algorithm. Therefore, the PACT will not be restricted by the small target, and more large scale targets such as humans also can be considered as the imaging object. There are a variety of trajectories to scan the target in this approach. Herein we focus on an in-plane rotational motion.

There are various photoacoustic reconstruction algorithms based on time-domain, Fourier domain, or model based approaches. Here, time-domain delay and sum based reconstruction algorithm is considered. Received photoacoustic signals contain shape information of the contrast agent as well as the distance from the target to the receive elements. Back projection algorithm works by recovering the information of the original structure by putting signals for each receive elements back to the source of the signal. The initial pressure $p_0(\vec{r})$ in the time domain can be expressed as follows:

$$p_0(\vec{r}) = \int_{\Omega_0} b\left(r_0, t = \frac{|\vec{r} - \vec{r}_0|}{c}\right) \frac{d\Omega_0}{\Omega_0}, \quad (29)$$

where $\Omega_0$ represents the solid angle subtended by the measurement surface $S_0$ with respect to the reconstruction point $\vec{r}$, and $\Omega_0 = 2\pi$ for planar geometry. $b(r_0, t)$ is the back projection term. The received acoustic pressure $p(\vec{r}_0, t)$ at position $\vec{r}_0$ and time t is directly inserted in this paper. c is the speed of sound, and $d\Omega_0$ is the solid angle subtended by the detection element with respect to $\vec{r}$.

Figure 57:
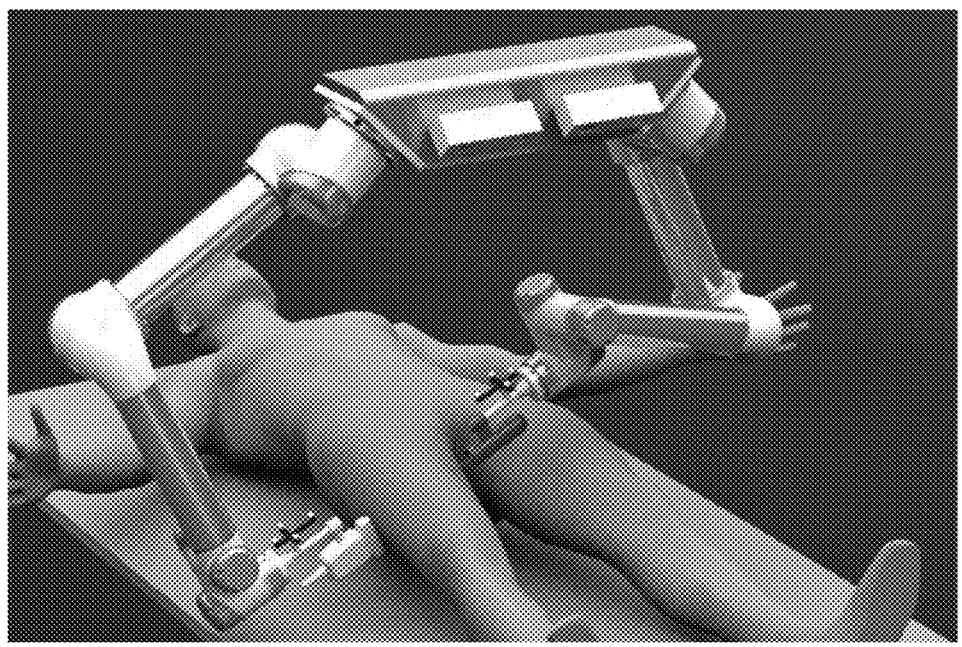
FIG. 57 shows an example setup of the system for robotically tracked photoacoustic computed tomography according to some embodiments of the invention.

As described above, an ultrasound transducer held by a robotic arm is swept around a surface. FIG. 57 shows an example setup of the system according to some embodiments of the invention. According to some embodiments of the invention, one arm can hold the laser light delivery system. We can have an accurate tracked-based PA imaging system as described above in detail. Herein, the laser may be considered an ultrasound probe, as it us used to generate a photoaccoustic effect. The laser can be fixed and the ultrasound can move around the excitation location to create PA tomography, synthetic aperture, or compounding imaging approaches. It can also work by fixing the ultrasound probe and moving the laser source. This laser system can be any electromagnetic source including a microwave source. It can be also a portable nuclear medicine probe. To enable the motion of the ultrasound probe, ultrasound calibration is necessary to identify the rotational and translational relationship between ultrasound image and robot end-effector. This rigid-body transformation is used to transform the coordinate system of robot base and ultrasound image, and it is possible to calculate the motion which is applied in the robot controller to generate a designated motion in ultrasound image coordinate. A base ultrasound image coordinate is defined and the position of transducer is controlled based on the base. Positional information is assigned to each pose and each single element, and that information can be used to reconstruct a tomographic image.

At the same time, it is necessary to recognize that there are several uncertain factors involved in the system: 1) the movement accuracy of the robotic tracking system, and 2) the precision of ultrasound calibration which affects the transformation from robot end effector to the ultrasound coordinate system. These uncertainties reduce the continuity and prevent a perfect reconstruction when pre-beamformed data from multiple poses are combined. Therefore, it is necessary to know the effect of the uncertainty in the reconstruction process.

Figures 58A, 58B, 58C:
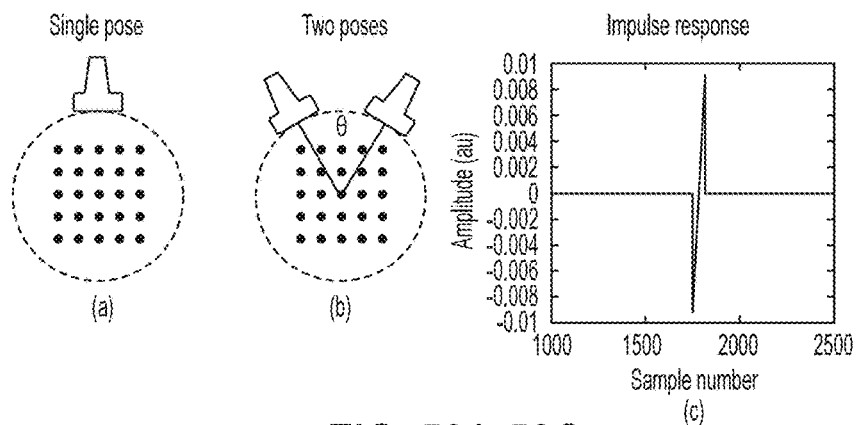
FIG. 58A shows the scanning geometry for the single pose case, (b) the geometry for two poses case, and (c) N-shape photoacoustic wave.
FIG. 58B shows the scanning geometry for the two pose case.
FIG. 58C shows an N-shape photoacoustic wave that is the simulated impulse response.

To validate the benefit of the robotic aperture extension, numerical phantom simulation studies were conducted. As the base condition, a 128 element ultrasound transducer with 0.47 mm pitch was used and it is assumed to be attached into a robot arm. The reconstructed result using the data from this transducer at only one position was regarded as the result of conventional PACT (FIG. 58A). On the contrary, it was assumed in two poses case that the transducer was placed two positions, in other words, it was moved from the first position to the second location (FIG. 58B). The angle between two poses was varied from 10 to 120 degree while the distance from the contrast agent was kept. The photoacoustic signals were collected twice at each position corresponding to two laser irradiation. A final image was generated utilizing these data. As the reason to choose this configuration, it was suitable to demonstrate the effect only comes from angle increase without increasing the number of receiving poses.

A set of 25 contrast agents was placed at the center with the diameter of 2 mm, each of them was separated by 10 mm in lateral and axial direction. The distance of the remote center from transducers was 50 mm. An N-shape impulse response was generated as the photoacoustic signal (FIG. 58C) [5].

$$\hat{t} = \frac{v_s}{a}\left(t - \frac{r-a}{v_s}\right), \quad (30)$$

$$p(r, t) = \begin{cases} \frac{Cv_s^2 a}{r}(1 - \hat{t}) & \text{for } 0 < \hat{t} < 2 \\ 0 & \text{otherwise,} \end{cases} \quad (31)$$

where $v_s$ is the sound speed, r is the radius coordinate, a is the radius of a uniformly irradiated sphere, and C is a constant to normalize the amplitude. Back projection algorithm based on the equation 29 was used in reconstruction. Hilbert transform was applied to reconstructed data. The speed of sound of 1500 m/s was used and, and the sampling frequency was 40 MHz. For display, the region around the target was cut.

In addition, the effect of tracking error in robotic arm is considered. To simulate possible uncertainty caused by robotic accuracy of motion as well as imperfect ultrasound calibration, the displacement with a certain magnitude was added in axial and lateral direction toward the right pose data. The rotational uncertainty was negligible in this case, because relative rotation between two poses should be accurate enough when only one transducer was used.

Figures 59A, 59B:
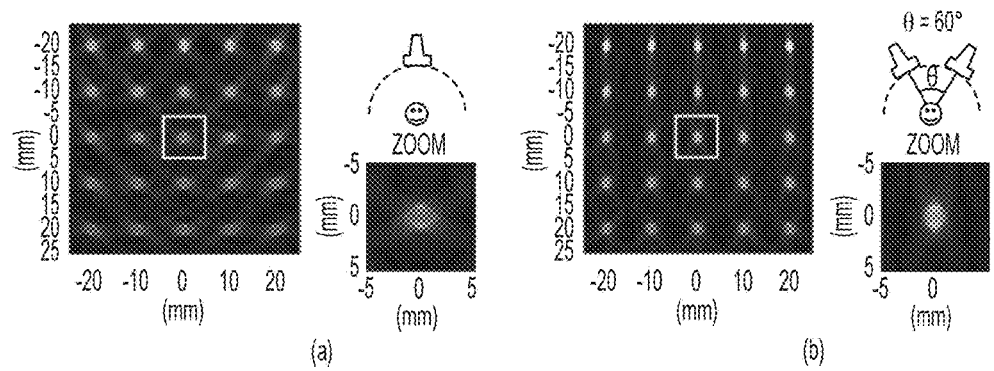
FIG. 59A shows simulation results of a single pose, wherein the center region is zoomed in the bottom right image.
FIG. 59B shows simulation results of two poses with 60 degree rotation, wherein the center region is zoomed in the bottom right image.

FIGS. 59A and 59B depict the reconstructed result for the single pose case and the two pose case (60 degree). In the single pose result, it could be seen that the shape of the target was extended in lateral direction, which was due to the limited aperture size. This result indicates the necessity to expand aperture for this depth. For the same aperture size, the image resolution depends on the target depth. It could be seen that the image resolution is better in the near region and it gets as the target depth increases. The aperture size is more significant in PA imaging compared to ultrasound, because only receive focusing is available in PA imaging, while both transmit and receive focusing can be applied in ultrasound. When two poses data were used to reconstruct an image, the lateral size of the target clearly became close to its original round shape due to aperture extension. FIGS. 59A and 59B illustrate the quality of the co-robotic photoacoustic reconstruction. FIG. 59B, one can easily observe the enhancement of the lateral resolution as a function of the angular separation between the two ultrasound frames. This is a direct advantage of using a co-robotic ultrasound photoacoustic imaging system—where the user can choose the region of interest and the robot can optimize the location of the ultrasound array with respect to the laser source and to the target.

Figure 60:
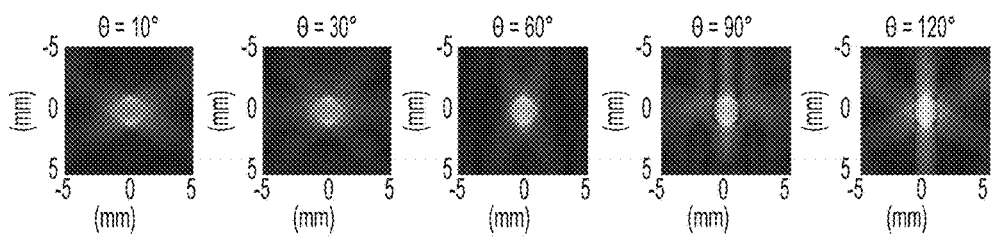
FIG. 60 shows a zoomed sphere target around 50 mm depth with different rotation angles.
Figure 61:
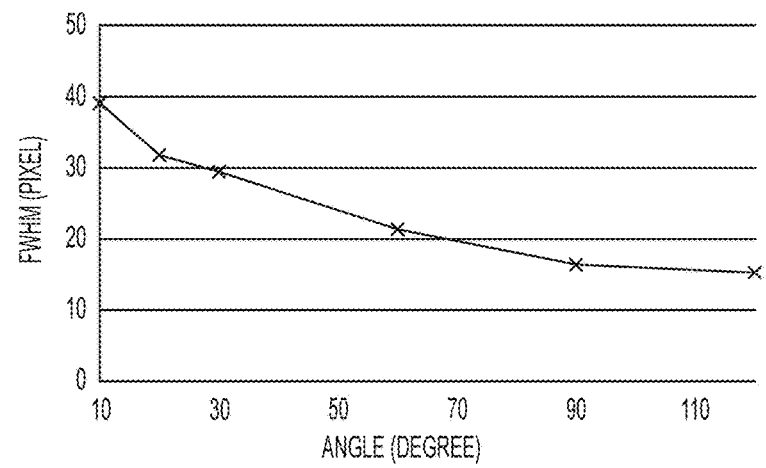
FIG. 61 is a plot of the full width at half maximum (FWHM) of the center sphere target.

In FIG. 60, the zoomed sphere point targets with different rotation angles are shown. As the rotation between two poses increases, the target shape got close to the round shape. When the angle over the 60 degree, the artifact in axial direction started to be appeared. The axial resolution also became worse compared to the 10 degree case. This effect increased more as the rotation angle between two poses increased. This is because that the rotation angle between two poses became too large that the aperture in between two poses was lacking. The artifact will be disappeared if consecutive apertures between two poses were kept. The lateral resolution of the target was evaluated as full with at half maximum (FWHM) (FIG. 61). One pixel represents 0.2 mm, the FWHM gradually got close to the target diameter 2 mm corresponding to the increase of rotational angle.

Figure 62:
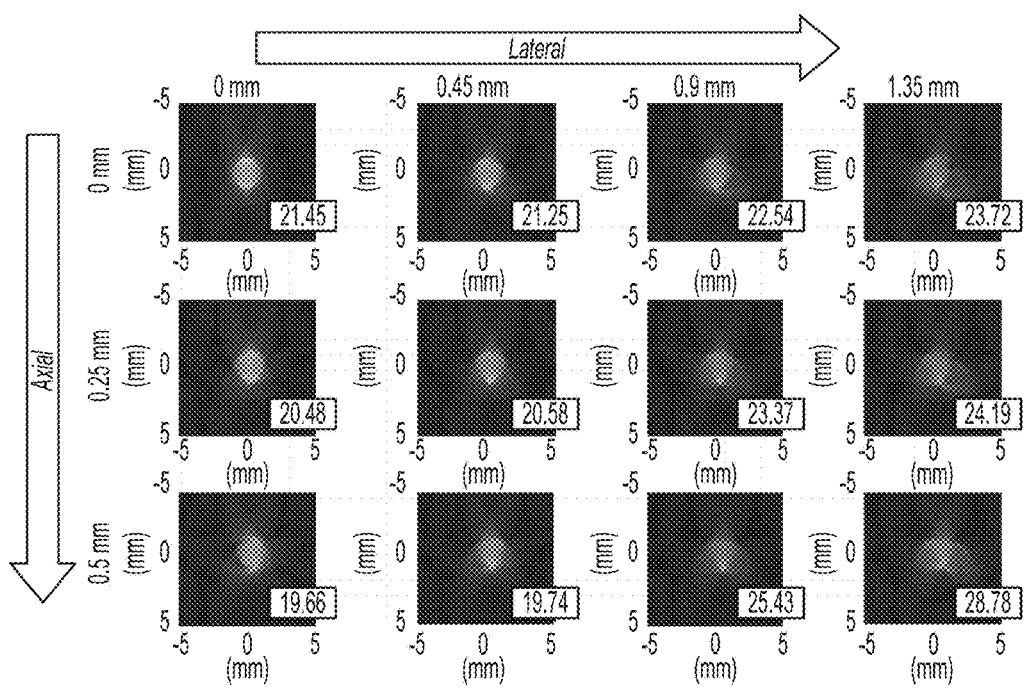
FIG. 62 shows the effect of error in lateral and axial direction, with the measured FWHM shown in the right bottom corner.

The reconstructed result with tracking error is shown in FIG. 62. The left top image is the ground truth, and it shows the result without applying any uncertainty. When the error is applied, one of the two pose is applied a translational error in lateral and axial direction with the designated amount. The reconstructed target in the result with tracking uncertainty was corrupted compared to the ground truth, and the effect increased corresponding to the magnitude of error. When the error in lateral direction is focused, the round shape was still kept until 0.45 mm error, but in 0.9 mm, it is hard to tell this is a round shape. In axial direction, the result with 0.5 mm error caused artifacts on the top and bottom of the target. From the result, the error in axial direction was more significant than that in lateral direction when the similar amount of error was applied. This is attributed to the fact that the axial direction is the direction that RF signal transfers. When the full directional scan is considered, the effect should be equivalent in lateral and axial. Therefore, it can be expected that when the rotation angle between multiple poses are huge, the effect in lateral and axial will be closer. The number shown in the corner of the image is the FWHM. The FWHM increased as the error increased.

We conducted an experiment to validate the proposed approach. A schematic illustration of the setup according to some embodiments of the invention is shown in FIG. 63. A UR5 robot (Universal Robot) is used as the robot arm, and a 6 cm linear array transducer was attached on the robot arm. The transducer has 128 elements with 0.47 mm pitch. 532 nm YAG laser was irradiated through an optical fiber to a black plastisol phantom, and the photoacoustic signal was generated from the irradiated spot. The probe was rotated in plane rotation with remote center of motion with 80 mm radius. The raw channel data was collected by DAQ device, and beamforming and consecutive data processing were operated in PC. As preoperative ultrasound calibration, a point based algorithm utilizing active-echo phantom was used [6,7]. The reconstruction precision of the calibration was 1.5 mm.

The experimental result is shown in FIGS. 64A and 64B. In FIG. 64A, the result of the single pose is shown on the left and the three poses with 20 degree as total rotation angle is shown on the right. The beamforming artifact appeared in the single pose result is reduced in the three poses result. The error existed between three poses was 3.7 mm, and it was manually compensated. The cause of error could be the inaccuracy of ultrasound calibration. The lateral profile of the target is shown in FIG. 64B. The CNR improvement of 8% was confirmed. In the single pose result, the side lobe was visible because of limited aperture, but that is reduced for multiple poses result due to compounding. No lateral resolution improvement was seen, because that when the light was shined into the phantom, the spot was not small enough, so that the original target shape was extended laterally. And the rotation angle was also not large enough to make the lateral resolution improvement be clearly seen.

We described herein a robotic approach to enable photoacoustic computed tomography. Simulation studies were conducted to validate the method, and a lateral resolution of the image could be seen. The tracking error of robot and ultrasound calibration degraded the shape of the target and FWHM. An experiment was conducted to demonstrate the feasibility of the system. The result indicates that the ultrasound calibration is required to the system, and the robotically tracked PACT has a huge potential to be a new scanning strategy.

FWHM is the matrix expected to evaluate the image quality, and the number becomes large when the error is large. However, it is not necessarily in agreement with the visual effect of the target. For instance, in FIG. 62, the left bottom image with 0.5 mm axial error shows the best FWHM, but the image was distorted around the boundary of the round shape. This indicates that other matrix such as pixel count with certain amplitude threshold should be considered as alternative parameter to judge the image quality.

REFERENCES

[1] Marmarelis, V. Z., Kim, T. S., and Shehada, R. EN, "High-resolution ultrasound transmission tomography," Proc. SPIE 5035, Medical Imaging: Ultrasonic Imaging and Signal Processing (2003).
[2] Khoei, Shadi. "Quantitative ultrasound computed tomography imaging of PAGAT radiation dosimetry gel." PhD Thesis, Queensland University of Technology (2013).
[3] Taylor R., Jensen P., Whitcomb L., Barnes A., Stoianovici D., Gupta P., Wang Z., de Juan E., and Kavoussi L., 1999, "A Steady-Hand robotic system for microsurgical augmentation," The International Journal of Robotics Research, 18(12), pp. 1201-1210.
[4] Abolmaesumi, P., et al., "Image-guided control of a robot for medical ultrasound." Robotics and Automation, IEEE Transactions on 18.1, 11-23 (2013).
[5] Najafi, F., Sepehri, N., "A robotic wrist for remote ultrasound imaging," Mechanism and Machine Theory, 46(8), 1153-1170 (2011).
[6] Mercier, L., et. al., "A review of calibration techniques for freehand 3-D ultrasound systems." Ultrasound in medicine & biology 31, no. 2, 143-165 (2005).
[7] Universal Robots ApS, April 2013, <http://media1.limitless.dk/UR_Tech_Spec/UR5_GB.pdf>, downloaded at Jan. 11, 2014.
[8] Edwards, S., et. al., <http://wiki.ros.org/universal_robot>, reached at Jan. 11, 2014.
[9] Ackerman, M. K., Cheng, A., Boctor, E. M., Chirikjian, G. S., "Online Ultrasound Sensor Calibration Using Gradient Descent on the Euclidean Group," Accepted in IEEE International Conference on Robotics & Automation, ICRA (2014).

References for Example 1

[1] R. W. Prager, U. Z. Ijaz, A. H. Gee, G. M. Treece, "Three-dimensional US imaging," Proc. of the Institution of Mechanical Engineers, Part H: J. of Engineering in Medicine 224(2), 193-223 (2010) [doi:10.1243/09544119JEIM586].
[2] A. Fenster, J. Bax, H. Neshat, N. Kakani, C. Romagnoli, "3D US imaging in image-guided intervention," in Advancements and Breakthroughs in US Imaging, Ch. 1, INTECH (2013) [doi:10.5772/55230].
[3] R. W. Prager, R. N. Rohling, A. H. Gee, L. Berman, "Rapid calibration for 3-D freehand ultrasound," Ultrasound in Medicine & Biology 24 (6), 855-869 (1998) [doi:10.1016/80301-5629(98)00044-1].

[4] J. Jago, A. Collet-Billon, C. Chenal, J. M. Jong, S. Makram-Ebeid, "XRES®: adaptive enhancement of ultrasound images," Medicamundi 46(3), 36-41 (2002).

[5] C. Hansen, N. Huttebrauker, A. Schasse, W. Wilkening, H. Ermert, M. Hollenhorst, L. Heuser, G. Schulte-Altedorneburg, "Ultrasound breast imaging using full angle spatial compounding: in-vivo results," IEEE Ultrasonics Symposium, 54-57 (2008) [doi:10.1109/ULTSYM.2008.0014].

[6] N. Duric, P. Littrup, A. Babkin, D. Chambers, S. Azevedo, A. Kalinin, R. Pevzner, et al., "Development of ultrasound tomography for breast imaging: technical assessment," Medical Physics 32(5), 1375-1386 (2005) [doi:10.1118/1.1897463].

[7] N. Duric, P. Littrup, L. Poulo, A. Babkin, R. Pevzner, E. Holsapple, O. Rama, and C. Glide, "Detection of breast cancer with ultrasound tomography: First results with the Computed Ultrasound Risk Evaluation (CURE) prototype," Medical physics 34(2), 773-785 (2007) [doi: 10.1118/1.2432161].

[8] J. P. Littrup, N. Duric, S. Azevedo, D. Chambers, J. V. Candy, S. Johnson, G. Auner, J. Rather, E. T. Holsapple, "Computerized ultrasound risk evaluation (CURE) system: development of combined transmission and reflection ultrasound with new reconstruction algorithms for breast imaging," Acoustical Imaging, 175-182. (2001).

[9] C. Li, L. Huang, N. Duric, H. Zhang, and C. Rowe, "An improved automatic time-of-flight picker for medical ultrasound tomography," Ultrasonics 49(1), 61-72 (2009) [doi:10.1016/j.ultras.2008.05.005].

[10] C. Li, N. Duric, P. Littrup, L. Huang, "In vivo breast sound-speed Imaging with ultrasound tomography," Ultrasound in medicine & biology 35(10), 1615-1628 (2009) [doi:10.1016/j.ultrasmedbio.2009.05.011].

[11] V. Z. Marmarelis, T. S. Kim, R. E. Shehada, "High-resolution ultrasound transmission tomography," in Medical Imaging, Proc. SPIE 5035, 33-40 (2003) [doi:10.1117/12.479887].

[12] T. S. Kim, S. H. Do, V. Z. Marmarelis, "Multiband tissue differentiation in ultrasonic transmission tomography," in Medical Imaging, Proc. SPIE 5035, 41-48 (2003) [doi:10.1117/12.479887].

[13] M. M. Bronstein, A. M. Bronstein, M. Zibulevsky, H. Azhari, "Reconstruction in diffraction ultrasound tomography using nonuniform FFT," IEEE Transactions on Medical Imaging 21(11), 1395-1401 (2002) [doi:10.1109/TMI.2002.806423].

[14] J. R. Jago, T. A. Whittingham, "Experimental studies in transmission ultrasound computed tomography," Physics in medicine and biology 369(11), 1515 (1991) [doi: 10.1088/0031-9155/36/11/011].

[15] P. Lasaygues, R. Guillermin, J. P. Lefebvre, "Ultrasonic computer tomography," in Bone Quantitative Ultarsound Book, Springer, 441-459 (2011) [doi:10.1007/978-94-007-0017-8_17].

[16] A. C. Kak and M. Slaney, Principles of Computerized Tomographic Imaging, IEEE Press (1988).

[17] R. Stotzka, J. Wuerfel, T. O. Mueller, H. Gemmeke, "Medical imaging by ultrasound computer tomography," in Medical Imaging, Proc. Of SPIE, 4687, 110-119 (2002) [doi:10.1117/12.462144].

[18] S. Khoei, "Quantitative ultrasound computed tomography imaging of PAGAT radiation dosimetry gel," Ph.D. dissertation, School of Chemistry, Physics & Mechanical Eng., Queensland Univ. of Tech., Australia (2013).

[19] J. F. Greenleaf, "Computerized tomography with ultrasound," Proc. of the IEEE 71(3), 330-337 (1983).

[20] "Softvue system," Delphinus Medical technologies, MI, USA, Available online: http://www.delphinusmt.com/our-technology/softvue-system (accessed July 2014)

[21] P. Abolmaesumi, S. E. Salcudean, W. H. Zhu, M. R. Sirouspour, S. P. DiMaio, "Image-guided control of a robot for medical ultrasound," IEEE Transactions on Robotics and Automation 18(1), 11-23 (2002) [doi: 10.1109/70.988970].

[22] E. M. Boctor, G. Fischer, M. A. Choti, G. Fichtinger, R. H. Taylor, "A dual-armed robotic system for intraoperative ultrasound guided hepatic ablative therapy: a prospective study," in Robotics and Automation, Proc. ICRA 3, 2517-2522, (2004) [doi:10.1109/ROBOT.2004.1307440].

[23] H. S. S. Ho, P. Mohan, E. D. Lim, D. L. Li, J. S. P. Yuen, W. S. Ng, W. K. O. Lau, and C. W. S. Cheng, "Robotic ultrasound-guided prostate intervention device: system description and results from phantom studies," The International Journal of Medical Robotics and Computer Assisted Surgery 5(1), 51-58 (2009) [doi:10.1002/rcs.232].

[24] L. Mercier, T. Langø, F. Lindseth, L. D. Collins, "A review of calibration techniques for freehand 3-D ultrasound systems," US in medicine & biology, 31(2), 143-165 (2005).

[25] M. K. Ackerman, A. Cheng, E. M. Boctor, G. S. Chirikjian, "Online ultrasound sensor calibration using gradient descent on the Euclidean group," IEEE International Conference on Robotics & Automation (2014).

[26] F. Aalamifar, R. Khurana, A. Cheng, R. H. Taylor, I. Iordachita, E. M. Boctor. (2014). Enabling technologies for robot assisted US tomography: system setup and calibration. Presented at SPIE Medical Imaging.

[27] "MTC documatation," Claron Technology, Canada, Available online: http://www.clarontech.com/API/index.html (accessed July 2014)

[28] "cisst libraries and Surgical Assistant Workstation (SAW)," Johns Hopkins University, MD, USA, Available online: https://trac.lcsr.jhu.edu/cisst/wiki/WikiStart (accessed July 2014).

[29] "The URScript programming language," Universal Robots, Denmark, Available online: http://www.wmv-robotics.de/home_htm_files/scriptmanual_en_1.5.pdf (accessed July 2014).

[30] X. Guo, A. Cheng, H. K. Zhang, H. Kang, R. Etienne-Cummings, E. M. Boctor, "Active echo: a new paradigm for ultrasound calibration," Medical Imaging Computing & Computer Assisted Interventions Conference (2014).

[31] M. K. Ackerman, A. Cheng, B. Shiffman, E. M. Boctor, G. Chirikjian, "Sensor calibration with unknown correspondence: solving AX=XB using Euclidean-group invariants," in Intelligent Robots and Systems, IEEE/RSJ International Conference, 1308-1313 (2013) [doi: 10.1109/IROS.2013.6696518].

[32] R. W. Prager, A. Gee, L. Berman, "Stradx: real-time acquisition and visualization of freehand three-dimensional ultrasound," Medical Image Analysis 3(2), 129-140 (1999) [doi:10.1016/51361-8415(99)80003-6].

[33] M. J. Gooding, S. H. Kennedy, J. A. Noble, "Temporal calibration of freehand three-dimensional ultrasound using image alignment," Ultrasound in medicine & biology 31(7), 919-927 (2005) [doi: 10.1016/j.ultrasmedbio.2005 0.04.007].

References for Example 2

[1] Randall R. De Martino, Adam W. Beck, Matthew W. Edwards, "Impact of screening versus symptomatic measurement of deep vein thrombosis in a nationalquality improvement registry", Journal of Vascular Surgery, 2012 (10), pp: 1045-1051.

[2] "DVT overview", WebMD, available online: http://www.webmd.com/dvt/ss/slideshow-deep-vein-thrombosis-overview

[3] Akil P Patel, Michael T. Koltz, Charles A. Sansur, "An analysis of deep vein thrombosis in 1277 consecutive neurosurgical patients undergoing routine weekly ultrasonography", Journal of Neurosurg, Vol. 118, March, 2013, pp: 505-509.

[4] "Deep Vein Thrombosis overview", Society of Interventional, available noline: http://www.sirweb.org/patients/deep-vein-thrombosis/

[5] Talbot S, "Use of real-time imaging in identifying deep venous obstruction: a preliminary report", Bruit, 1982, 7, pp: 41-42.

[6] Heather L. Gornik, Aditya M. Sharma, "Duplex ultrasound in the diagnosis of lower-extremity deep venous thrombosis", Circulation, Journal of the American Heart Association, 2014; 129, pp: 917-921.

[7] Vanderpool, H. E., Friis, E. A., Smith, B. S., Harms, K. L., "Prevalence of carpal tunnel syndrome and other work-related musculoskeletal problems in cardiac sonographers", JOEM: Journal of Occupational and Environmental Medicine, Vol. 35, June, 1993, pp: 97-113.

[8] Francois Conti, Jaeheung Park, OussamaKhatib, "Interface design and contral strategies for a robot assisted ultrasonic examination system", Experimental Robotics, Springer Tracts in Advanced Robotics, Vol. 79, 2014, pp: 97-113.

[9] Pierror F., Dombre, E., Dgoulange, E., Urbain, "Hippocrate: a safe robot arm for medical applications with force feedback", Medical Image Analysis, 3(3), 1999, pp: 285-300.

[10] Vilhchis, A., Troccaz, J. Cinquin, P., Masuda, K., Pellissier, F., "A new robot architecture for Tele-Echography", IEEE Transaction on Robotics and Automation, 19(5), 2003, pp: 922-926.

[11] Abolmaesumi, P., Salcudean, S. E., Zhu, W.-H., Sirouspour, "Image-guided control of a robot for percutaneous Cholecystostomy", Phys. Med. Biol. 49(3), 2004, pp: 441-445.

[12] Hong, J., Dohi, T., Hashizume, M., Konishi, K., Hata, N., "An ultrasound driven needle insertion robot for percutaneous cholecystostomy", Phys. Med. Biol. 49(3), 2004, pp: 441-455.

[13] Lessard, S., et al, "Parallel Robot for medical 3D-Ultrasound Imaging", IEEE International Symposium on Industrial Electronics (2006).

[14] Microsoft. Kinect for Windows. Available online: http://www.microsoft.com/en-us/Kinectforwindows/

[15] Walker Burgin, Caroline Pantofaru, William D. Smart, "Using depth information to improve face detection", Proceedings of the 6th International Conference on Human-Robot Interaction, Lausanne, Switzerland, 2011, March, pp. 6-9.

[16] Patrick Benavidez, Mo Jamshidi, "Mobile robot navigation and target tracking system", Proceedings of the 6th International Conference on system of Systems Engineering: SoSE in Cloud Computign, Smart Grid, and Cyber Security, SoSE 2011, Albuquerque, N. Mex., USA, 2011; pp. 299-304.

[17] Bertram Drost, Markus Ulrich, Nassir Navab, Slobodan Ilic, "Model Globally, match locally: efficient and robust 3D object recognition", IEEE Conference on Computer Vision and Pattern Recognition (CVPR), 2010, San Francisco, Calif., USA, 2010, pp: 998-1005.

[18] ShahramIzadi, David Kim, OtmarHilliges, David Molyneaus, Richard Newcombe, etc. "KinectFusion: real-time 3D reconstruction and interaction using a moving depth camera", UIST'11 Proceedings of the 24th Annual ACM Symposium on User Interface Software and Technology, ACM New York, N.Y., USA, 2011, pp: 559-568.

[19] Sebastian Bauer, JakobWasza, Sven Haase, etc. "Multimodal suface registration for markerless initial patient setup in radiation therapy using Microsoft's Kinect sensor", IEEE International Conference on Computer Vision Workshops (ICCV), Barcelona, Spain, 2011, pp: 1175-1181.

[20] Polaris_Rigid_Body_Data_Sheet_(8700339), NDI.

[21] P. J. Besl, N. MacKay, "A method for registration of 3-d shapes", IEEE Transactions on Pattern Analysis and Machine Intelligence, Vol. 14, No. 2, 1992, pp: 239-256.

References for Example 3

[1] Detmer P. R., Bashein G., Hodges T., Beach K. W., Filer E. P., Burns D. H., and Strandness Jr D. E., "3D ultrasonic image feature localization based on magnetic scanhead tracking: in vitro calibration and validation," Ultrasound in Medicine and Biology, 20 (9), 923-936, 1994.

[2] Poon, T., Rohling, R., "Comparison of calibration methods for spatial tracking of a 3-D ultrasoundprobe." Ultrasound in Medicine and Biology, 31(8), 1095-1108, 2005.

[3] Prager, R. W., Rohling, R. N., Gee, A. H., Berman, L., "Automatic Calibration for 3-D Free-Hand Ultrasound," Dep. Eng., Cambridge Univ., 1997.

[4] Melvaer, E. L., Mørken, K., Samset, E., "A motion constrained cross-wire phantom for tracked 2D ultrasound calibration," CARS, 7(4), 611-620, 2012.

[5] Cleary, K., Zhang, H., Glossop, N., Levy, E., Wood, B., Banovac, F., "Electromagnetic Tracking for Image-Guided Abdominal Procedures: Overall System and Technical Issues," IEEE EMBS, 6748-6753, 2005.

[6] Guo, X, Tavakoli B., Kang, H.-J., Kang J. U., Etienne-Cummings R., Boctor E. M., "Photoacoustic Active Ultrasound Element for Catheter Tracking", SPIE Photonics West 2014.

[7] Ackerman M. K., Cheng A., Boctor E., and Chirikjian G. S., "Online Ultrasound Sensor Calibration Using Gradient Descent on the Euclidean Group," Accepted to International Conference on Robotics and Automation, 2014.

[8] Treece G. M., Gee A. H., Prager R. W., Cash C. J. C., and Berman L. H., "High-definition freehand 3-D ultrasound", Ultrasound in Medicine and Biology, 29(4), pp. 529-546, 2003.

[9] Morris, P., et. al, "A Fabry-Pérot fiber-optic ultrasonic hydrophone for the simultaneous measurement of temperature and acoustic pressure", J. Acoust. Soc. Am, Vol. 125, No. 6, page 3611, June 2009

Reference for Example 4

[1] Prager R. W., Rohling R. N., Gee A. H., and Berman L. H., "Rapid Calibration for 3-D freehand Ultrasound," Ultrasound in Medicine and Biology, 24 (6), 855-869, 1998.

[2] Detmer P. R., Bashein G., Hodges T., Beach K. W., Filer E. P., Burns D. H., and Strandness Jr D. E., "3D ultrasonic image feature localization based on magnetic scanhead tracking: in vitro calibration and validation," Ultrasound in Medicine and Biology, 20 (9), 923-936, 1994.

[3] Pagoulatos N., Haynor D. R., and Kim Y., "A Fast Calibration Method for 3-D Tracking of Ultrasound Images using a Spatial Localizer," Ultrasound in Medicine and Biology, 27(9), 1219-1229, 2001.

[4] Boctor, E. M., Viswanathan, A., Choti, M. A., Taylor, R. H., Fichtinger, G., Hager, G. D., "A Novel Closed Form Solution for Ultrasound Calibration," IEEE Int Symp. On Biomedical Imaging, 527-530, 2004.

[5] Guo, X. Y., Cheng, A., Zhang H. C., Etienne-Cummings, R., and Boctor, E. M., "Active Echo: A New Paradigm for Ultrasound Calibration," MICCAI 2014, LNCS Vol. 8674, 397-404, 2014.

[6] Kang, H. J., Guo, X., Azar, R. Z., Cheng, A., and Boctor, E. M., "Software framework for spatially tracked pre-beamformed RF data acquisition with a freehand clinical ultrasound transducer," In SPIE Medical Imaging (pp. 90401W-90401W). International Society for Optics and Photonics. 2014.

References for Example 5

[1] Duric, Nebojsa, Peter Littrup, Lou Poulo, Alex Babkin, Roman Pevzner, Earle Holsapple, Olsi Rama, and Carri Glide. "Detection of breast cancer with ultrasound tomography: First results with the Computed Ultrasound Risk Evaluation (CURE) prototype." Medical physics 34, no. 2 (2007): 773-785.

[2] Delphinus Medical Technologies, "http://www.delphinusmt.com/our-technology/softvue-system." Accessed Jan. 11, 2015.

[3] Duric, Nebojsa, Peter Littrup, Alex Babkin, David Chambers, Stephen Azevedo, Arkady Kalinin, Roman Pevzner, Mikhail Tokarev, and Earle Holsapple. "Development of ultrasound tomography for breast imaging: Technical assessment." Medical Physics 32.5 (2005): 1375-1386.

[4] Li, Cuiping, Nebojsa Duric, Peter Littrup, and Lianjie Huang. "In vivo Breast Sound-Speed Imaging with Ultrasound Tomography." Ultrasound in medicine & biology 35.10 (2009): 1615-1628.

[5] Glide, Carri, Nebojsa Duric, and Peter Littrup. "Novel approach to evaluating breast density utilizing ultrasound tomography." Medical physics 34.2 (2007): 744-753.

[6] Littrup, Peter J., Neb Duric, Stephen Azevedo, David Chambers, James V. Candy, Stephen Johnson, Gregory Auner, John Rather, and Earle T. Holsapple. "Computerized ultrasound risk evaluation (CURE) system: Development of combined transmission and reflection ultrasound with new reconstruction algorithms for breast imaging." Acoustical Imaging. Springer US, 2002. 175-182.

[7] Jago, J. R., and T. A. Whittingham. "Experimental studies in transmission ultrasound computed tomography." Physics in medicine and biology 36.11 (1991): 1515.

[8] Marmarelis, Vasilis Z., Tae-Seong Kim, and Ramez E N Shehada. "High-resolution ultrasound transmission tomography." Medical Imaging 2003. International Society for Optics and Photonics, 2003.

[9] Ashfaq, Mohammad. Measuring and Signal Processing Techniques for Ultrasound Computed Tomography. Diss. PhD thesis. Bochum, Germany: Ruhr University, 2007.

[10] Greenleaf, James F. "Computerized tomography with ultrasound." Proceedings of the IEEE 71.3 (1983): 330-337.

[11] R. L. Siddon. "Fast calculation of the exact radiological path for a three-dimensional CT array." Medical physics 12.2 (1985): 252-255.

[12] Aalamifar, Fereshteh, Rishabh Khurana, Alexis Cheng, Russell H. Taylor, Iulian Iordachita, and Emad M. Boctor. "Enabling technologies for robot assisted ultrasound tomography: system setup and calibration." SPIE Medical Imaging. International Society for Optics and Photonics, 2014.

[13] Guo, Xiaoyu, Alexis Cheng, Haichong K. Zhang, Hyun-Jae Kang, Ralph Etienne-Cummings, and Emad M. Boctor. "Active echo: a new paradigm for ultrasound calibration." Medical Image Computing and Computer Assisted Intervention 2014.

[14] Ackerman, Martin Kendal, Alexis Cheng, Emad Boctor, and Gregory Chirikjian. "Online ultrasound sensor calibration using gradient descent on the Euclidean Group." Robotics and Automation (ICRA), 2014 IEEE International Conference on. IEEE, 2014.

[15] M. Lusting, SparseMRI Toolbox downloaded from http://www.eecs.berkeley.edu/~mlustig/Software.html. Downloaded: Aug. 1, 2014.

Reference for Example 6

[1] Brecht, H. P. et al. Whole-body three-dimensional optoacoustic tomography system for small animals. J Biomed Opt 14, 064007 (2009)

[2] Wang L. V. and Hu S., "Photoacoustic tomography: in vivo imaging from organelles to organs," Science 335, 1458-1462 (2012)

[3] Ma R., Taruttis A., Ntziachristos V., and Razansky D., "Multispectral optoacoustic tomography (MSOT) scanner for whole-body small animal imaging," Opt. Express 17(24), 21414-21426 (2009)

[4] Xu, M. and Wang, L. V., "Universal back-projection algorithm for photoacoustic computed tomography," Phys. Rev. E. 71(1), 016706 (2005)

[5] Wang L., "Photoacoustic Imaging and Spectroscopy," CRC Press (2009)

[6] Guo X., Cheng A, Zhang H. K., Kang H-J, Etienne-Cummings R., and Boctor E. M., "Active Echo: A new Paradigm for Ultrasound Calibration", MICCAI (2014)

[7] Guo X., Kang H-J, Etienne-Cummings R, Boctor E. M., "Active Ultrasound Pattern Injection System (AUSPIS) for Interventional Tool Guidance," PloS one, vol. 9, e104262 (2014)

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A cooperatively controlled robot-assisted ultrasound tomography system, comprising:
a first ultrasound probe;
a robot comprising a manipulator arm having a tool end;
a second ultrasound probe attached to the tool end of the manipulator arm, the first ultrasound probe and the second ultrasound probe configured to communicate signals therebetween;

a tracker to track at least one of a position or pose of the first ultrasound probe,
the tracker including a camera configured to detect a marker associated with the first ultrasound probe,
the camera and the marker being positioned such that the marker is in a line of sight of the camera during an ultrasound scan;

a robot control system in operable communication with the tracker and configured to control at least one of a position or a pose of the second ultrasound probe based on the at least one tracked position or pose of the first ultrasound probe,
the at least one of the position or the pose of the second ultrasound probe to mirror the at least one tracked position or pose of the first ultrasound probe during a simultaneous imaging operation of the second ultrasound probe and the first ultrasound probe; and an ultrasound processing system configured to:
communicate with at least one of the first ultrasound probe or the second ultrasound probe; and
provide, for display, an ultrasound image based on the simultaneous imaging operation of the first ultrasound probe and the second ultrasound probe.

2. The cooperatively controlled robot-assisted ultrasound tomography system according to claim 1, wherein the tracker is adapted to communicate with the robot control system.

3. The cooperatively controlled robot-assisted ultrasound tomography system according to claim 1, wherein the tracker is an optical tracking system comprising:
an optical detection system attached to the manipulator arm.

4. The cooperatively controlled robot-assisted ultrasound tomography system according to claim 1, wherein the tracker comprises an optical marker attached to the first ultrasound probe.

5. The cooperatively controlled robot-assisted ultrasound tomography system according to claim 1, wherein the first ultrasound probe is configured to operate in both a transmit and a receive mode to detect reflected ultrasound signals transmitted from the first ultrasound probe.

6. The cooperatively controlled robot-assisted ultrasound tomography system according to claim 1, wherein the robot control system is configured to align the first ultrasound probe and the second ultrasound probe with a body of interest therebetween, and
wherein the first ultrasound probe and the second ultrasound probe are adapted to operate in a transmit mode.

7. The cooperatively controlled robot-assisted ultrasound tomography system according to claim 6, wherein one of the first ultrasound probe or the second ultrasound probe comprises a dedicated ultrasound transmitter and the other of the first ultrasound probe or the second ultrasound probe comprises a dedicated ultrasound receiver.

8. The cooperatively controlled robot-assisted ultrasound tomography system according to claim 6, wherein at least one of the second ultrasound probe or the manipulator arm comprises a force sensor arranged to detect a force applied by the second ultrasound probe to the body of interest.

9. The cooperatively controlled robot-assisted ultrasound tomography system according to claim 1, wherein the first ultrasound probe is a hand-operable ultrasound probe such that the robot control system controls the at least one of the position or ft the pose of the second ultrasound probe based on motions performed by a user of the first ultrasound probe.

10. The cooperatively controlled robot-assisted ultrasound tomography system according to claim 1, further comprising:
an additional manipulator arm associated with at least one of the robot or an additional robot, wherein the first ultrasound probe is attached to a tool end of the additional manipulator arm.

11. The cooperatively controlled robot-assisted ultrasound tomography system according to claim 10, wherein the robot control system is configured to teleoperatively control the at least one of the position or the pose of the first ultrasound probe based on input from a user.

12. The cooperatively controlled robot-assisted ultrasound tomography system according to claim 10, wherein the manipulator arm and the additional manipulator arm are connected to a harness, and
wherein the tracker is an optical tracking system comprising an optical detection system attached to the harness.

13. The cooperatively controlled robot-assisted ultrasound tomography system according to claim 1, wherein the robot control system is configured to determine a calibration of the first ultrasound probe and the second ultrasound probe based on the signals received by the first ultrasound probe and the second ultrasound probe.

14. The cooperatively controlled robot-assisted ultrasound tomography system according to claim 1, wherein the marker further comprises a first optical marker attached to the first ultrasound probe and a second optical marker attached to the second ultrasound probe.

15. A cooperatively controlled robot-assisted ultrasound tomography system, comprising:
a first ultrasound probe;
a robot comprising a manipulator arm having a tool end;
a second ultrasound probe attached to the tool end of the manipulator arm;
a tracker to track at least one of a position or pose of the first ultrasound probe,
the tracker including a camera configured to detect a marker associated with the first ultrasound probe;
a robot control system in operable communication with the tracker and configured to control at least one of a position or a pose of the second ultrasound probe based on the at least one tracked position or pose of the first ultrasound probe,
the at least one of the position or the pose of the second ultrasound probe to mirror the at least one tracked position or pose of the first ultrasound probe during a simultaneous imaging operation of the second ultrasound probe and the first ultrasound probe; and
an ultrasound processing system configured to:
communicate with the first ultrasound probe and the second ultrasound probe, and
provide, for display, an ultrasound image based on simultaneous imaging operation of the first ultrasound probe and the second ultrasound probe.

16. The cooperatively controlled robot-assisted ultrasound tomography system of claim 15, wherein the robot control system is configured to align the first ultrasound probe and the second ultrasound probe with a body of interest therebetween, and
wherein the first ultrasound probe and the second ultrasound probe are adapted to operate in transmit mode.

17. The cooperatively controlled robot-assisted ultrasound tomography system of claim 15, wherein the tracker is an optical tracking system comprising:
an optical detection system attached to the manipulator arm.

18. The cooperatively controlled robot-assisted ultrasound tomography system of claim 15, wherein one of the first ultrasound probe or the second ultrasound probe comprises a dedicated ultrasound transmitter and the other of the first ultrasound probe or the second ultrasound probe comprises a dedicated ultrasound receiver.

19. The cooperatively controlled robot-assisted ultrasound tomography system of claim 15, wherein the tracker is adapted to communicate with the robot control system.

20. A method, comprising:
tracking, by a tracker of a cooperative robot-assisted ultrasound system, at least one of a position or pose of a first ultrasound probe,
the tracker including a camera configured to detect a marker associated with the first ultrasound probe;
receiving, by the cooperative robot-assisted ultrasound system, information associated with the at least one of the position or pose of the first ultrasound probe;
causing, by the cooperative robot-assisted ultrasound system, a second ultrasound probe, attached to a tool end of a manipulator arm of a robot, to mirror at least one of a position or a pose of the second ultrasound probe based on the at least one of the tracked position or pose of the first ultrasound probe during a simultaneous imaging operation of the second ultrasound probe and the first ultrasound probe;
displaying, by the cooperative robot-assisted ultrasound system, one or more ultrasound images based on the simultaneous imaging operation of the first ultrasound probe and the second ultrasound probe.

21. The method of claim 20, further comprising:
aligning the first ultrasound probe and the second ultrasound probe with a body of interest therebetween; and
wherein the first ultrasound probe and the second ultrasound probe are adapted to operate in transmit mode.

* * * * *

UNITED STATES PATENT AND TRADEMARK OFFICE
CERTIFICATE OF CORRECTION

PATENT NO. : 10,335,116 B2
APPLICATION NO. : 14/690232
DATED : July 2, 2019
INVENTOR(S) : Emad M. Boctor et al.

Page 1 of 1

It is certified that error appears in the above-identified patent and that said Letters Patent is hereby corrected as shown below:

In the Claims

In Claim 9, Column 52, Line 1, "position or ft the pose" should be changed to --position or the pose--.

In Claim 15, Column 52, Lines 58-59, "based on simultaneous imaging operation" should be changed to --based on the simultaneous imaging operation--.

Signed and Sealed this
Ninth Day of June, 2020

Andrei Iancu
*Director of the United States Patent and Trademark Office*